(12) United States Patent
Sayarpour

(10) Patent No.: US 10,190,395 B2
(45) Date of Patent: Jan. 29, 2019

(54) FLOODING ANALYSIS TOOL AND METHOD THEREOF

(71) Applicant: Chevron U.S.A. Inc., San Ramon, CA (US)

(72) Inventor: Morteza Sayarpour, Houston, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 531 days.

(21) Appl. No.: 14/832,792

(22) Filed: Aug. 21, 2015

(65) Prior Publication Data

US 2016/0061020 A1 Mar. 3, 2016

Related U.S. Application Data

(60) Provisional application No. 62/135,016, filed on Mar. 18, 2015, provisional application No. 62/040,909, filed on Aug. 22, 2014.

(51) Int. Cl.
*E21B 41/00* (2006.01)
*E21B 43/14* (2006.01)
(Continued)

(52) U.S. Cl.
CPC .......... *E21B 41/0092* (2013.01); *E21B 43/14* (2013.01); *E21B 43/16* (2013.01);
(Continued)

(58) Field of Classification Search
CPC .................................................. E21B 41/0092
See application file for complete search history.

(56) References Cited

U.S. PATENT DOCUMENTS

| 4,181,176 A | 1/1980 | Frazier |
| 5,924,048 A | 7/1999 | McCormack et al. |

(Continued)

OTHER PUBLICATIONS

Dietrich, J.K., et al.; "A Method for Determining Reservoir Fluid Saturations Using Field Production Data"; (1972), SPE-AIME 47th Annual Fall Meeting, pp. 477-486.
(Continued)

*Primary Examiner* — Manuel L Barbee
*Assistant Examiner* — Raymond L Nimox
(74) *Attorney, Agent, or Firm* — Ana C. Jaquez

(57) ABSTRACT

Described herein are various embodiments of computer-implemented methods, computing systems, and program products for analyzing a flood operation on a hydrocarbon reservoir. For example, an embodiment of a computer implemented method of determining a value of injected fluid includes, for a first injection well of the hydrocarbon reservoir: receiving injection rate data for the first injection well and production rate data for at least one production well communicating with the injection well, running capacitance resistance modeling using the received data to generate an interwell connectivity for each injection well and production well pair, determining a value of injected fluid for each injection well and production well pair using the generated interwell connectivity for the well pair and an oil-cut value for the production well of the pair, and aggregating the generated values of injected fluid per pair to determine a value of injected fluid for the first injection well.

20 Claims, 75 Drawing Sheets

(51) Int. Cl.
*E21B 43/16* (2006.01)
*E21B 43/20* (2006.01)
*E21B 47/00* (2012.01)
*E21B 49/00* (2006.01)
*G01N 27/22* (2006.01)
*G01V 99/00* (2009.01)

(52) U.S. Cl.
CPC .............. *E21B 43/20* (2013.01); *E21B 47/00* (2013.01); *E21B 47/0003* (2013.01); *E21B 49/00* (2013.01); *G01N 27/22* (2013.01); *G01V 99/005* (2013.01)

(56) References Cited

U.S. PATENT DOCUMENTS

| | | | |
|---|---|---|---|
| 7,963,327 B1 | 6/2011 | Saleri et al. | |
| 8,428,924 B2 | 4/2013 | Shook et al. | |
| 2006/0224369 A1 | 10/2006 | Yang et al. | |
| 2009/0107669 A1* | 4/2009 | Elphick | E21B 43/16 166/254.1 |
| 2009/0194274 A1* | 8/2009 | Del Castillo | E21B 43/00 166/250.01 |
| 2010/0051280 A1* | 3/2010 | Akram | E21B 43/2406 166/303 |
| 2011/0320128 A1* | 12/2011 | Shook | E21B 43/162 702/13 |
| 2012/0173220 A1 | 7/2012 | Li et al. | |
| 2012/0191432 A1 | 7/2012 | Khataniar et al. | |
| 2012/0290211 A1* | 11/2012 | Murphy | E21B 43/00 702/13 |
| 2013/0116998 A1* | 5/2013 | Shirzadi | E21B 43/20 703/10 |
| 2013/0245952 A1 | 9/2013 | Lin et al. | |
| 2014/0288909 A1 | 9/2014 | Prestwood et al. | |
| 2015/0006083 A1 | 1/2015 | McAuliffe et al. | |
| 2015/0032377 A1 | 1/2015 | McAuliffe et al. | |
| 2016/0063150 A1* | 3/2016 | Safonov | E21B 43/16 703/10 |
| 2016/0177679 A1 | 6/2016 | Zhang et al. | |
| 2016/0177687 A1 | 6/2016 | Sayarpour | |
| 2016/0177688 A1 | 6/2016 | Sayarpour et al. | |
| 2016/0177689 A1 | 6/2016 | Zhang et al. | |
| 2016/0177690 A1 | 6/2016 | Sayapour et al. | |
| 2016/0178799 A1 | 6/2016 | Sayarpour et al. | |

OTHER PUBLICATIONS

Expended European Search Report, dated May 17, 2016, during the prosecution of European Application No. 15182090.9.
Kim, Jong S., et al.; "Integrated Capacitance-Resistance Model for Characterizing Waterflooded Reservoirs"; (2012), Proceedings of the IFAC Workshop on Automatic Control in Offshore Oil and Gas Production, pp. 19-24.
Mamghaderi, Azadeh, et al.; "Optimization of Waterflooding Performance in a Layered Reservoir Using a Combination of Capacitance-Resistive Model and Genetic Algorithm Method"; (2012), Journal of Energy Resources Technology, vol. 135, pp. 1-9.
Mohaghegh, Shahab D et al.; "Development of Surrogate Reservoir Model (SRM) for Fast Track Analyses of a Complex Reservoir"; (2009), International Journal of Oil, Gas and Coal Technology, vol. 2, No. 1, pp. 2-23.
Moreno, Gustavo, et al.; "On the Uncertainty of Interwell Connectivity Estimations from the Capacitance-Resistance Model"; (2014), Petroleum Science, vol. 11, No. 2, pp. 265-271.
Nguyen, Anh P., et al.; "Integrated Capacitance Resistive Model for Reservoir Characterization in Primary and Secondary Recovery"; SPE 147344, (2011), pp. 1-20.
Sayarpour, Morteza; "Development and Application of Capacitance-Resistive Models to Water/$CO_2$ Floods"; Dissertation, (2008), Title and Dedication pages, pp. v-xviii, and pp. 1-41.
Sayarpour, Morteza; "Development and Application of Capacitance-Resistive Models to Water/$CO_2$ Floods"; Dissertation, (2008), pp. 42-101.
Sayarpour, Morteza; "Development and Application of Capacitance-Resistive Models to Water/$CO_2$ Floods"; Dissertation, (2008), pp. 102-161.
Sayarpour, Morteza; "Development and Application of Capacitance-Resistive Models to Water/$CO_2$ Floods"; Dissertation, (2008), pp. 162-218.
Sayarpour, M., et al.; "Field Applications of Capacitance-Resistive Models in Waterfloods"; SPE 114983-MS, (2008), pp. 1-15.
Sayarpour, M., et al.; "Field Applications of Capacitance-Resistive Models in Waterfloods"; SPE 114983-PA, (2009), pp. 853-864.
Sayarpour, M., et al.; "Probabilistic History Matching with the Capacitance-Resistance Model in WaterFloods: A Precursor to Numerical Modeling"; SPE 129604, (2010), pp. 1-15.
Sayarpour, M., et al.; "The Use of Capacitance-Resistive Models for Rapid Estimation of Waterflood Performance and Optimization"; SPE 110081, (2007), pp. 1-13.
Weber, Daniel, et al.; "Improvements in Capacitance-Resistive Modeling and Optimization of Large Scale Reservoirs"; SPE 121299, (2009), pp. 1-17.
Yousef, A.A., et al.; "A Capacitance Model to Infer Interwell Connectivity from Production and Injection Rate Fluctuations"; SPE 95322, (2005), pp. 1-19.
Yousef, A.A., et al.; "A Capacitance Model to Infer Interwell Connectivity from Production and Injection Rate Fluctuations"; (2006), SPE Reservoir Evaluation & Engineering, pp. 630-646.
Extended European Search Report, dated Jul. 10, 2018, during the prosecution of European Application No. 18158876.5.
Moghadam, J. Naseryan, et al.; "Evaluation of Waterflooding Performance in Heavy Oil Reservoirs Applying Capacitance-Resistive Model"; Petroleum Science and Technology, (2011), vol. 29, Issue 17, pp. 1811-1824.
Moreno, Gustavo, et al.; "On the Uncertainty of Interwell Connectivity Estimations from the Capacitance-Resistance Model"; (2014), vol. 11, pp. 265-271.

* cited by examiner for a first entity (e.g., the first entity is at a field level, a reservoir level, a well level, a zone level, or any combination thereof). 1800 solving an injection entity index to generate an injection entity index value, where the injection entity index includes injection efficiency, value of injected fluid, and pore volume injected for a period of time 1802 solving a production entity index to generate a production entity index value, where the production entity index includes estimate of remaining moveable oil in place 1804 evaluating an operation entity index that represents operation status to generate an operation entity index value 1806 combining the injection entity index value, the production entity index value, and the operation entity index value to generate a conformance problem index value for the first entity 1808 comparing the generated conformance problem index value for the first entity and a threshold to determine if the first entity is a conformance candidate 1810 generating a conformance problem index value for at least one other entity 1812 ranking the first entity and the at least one other entity by based on the generated conformance problem index value of the entity (e.g., a higher generated conformance problem index value indicates a higher likelihood of a conformance problem) 1814 where the first entity has the highest generated conformance problem index value, and where the first entity is at a field level, further comprising generating a conformance problem index value at a reservoir level, well level, a zone level, or any combination thereof 1816 where the first entity has the highest generated conformance problem index value, and where the first entity is at a reservoir level, further comprising generating a conformance problem index value at a well level, a zone level, or any combination thereof 1818 where the first entity has the highest generated conformance problem index value, and where the first entity is at a well level, further comprising generating a conformance problem index value at a zone level 1820

FIG. 18  (optional) Go to FIGS. 19A and/or 19B

↓

| First Flood Heterogeneity measure | | | | Injector 1 | |
|---|---|---|---|---|---|
| Vp | fij | F/Vp | Phi | F | |
|  |  |  | 0 | 0 | 0 |
| 95,238 | 0.2000000000 | 2.10 | 0.08473 | 0.2 | 0.00847 |
| 153,846 | 0.3000000000 | 1.95 | 0.2216 | 0.5 | 0.05638 |
| 106,667 | 0.2000000000 | 1.88 | 0.3165 | 0.7 | 0.11332 |
| 111,111 | 0.1000000000 | 0.90 | 0.41535 | 0.8 | 0.18745 |
| 246,914 | 0.1000000000 | 0.41 | 0.63501 | 0.9 | 0.37417 |
| 410,256 | 0.1000000000 | 0.24 | 1 | 1 | 0.72091 |
|  |  |  |  | Lc | 0.44182 |

FIG. 21A

| Second Flood Heterogeneity measure | | | | Injector 1 | |
|---|---|---|---|---|---|
| Vp | fij | F/Vp | Phi | F | |
|  |  |  | 0 | 0 | 0 |
| 194444 | 0.22 | 1.13143 | 0.16213 | 0.22 | 0.01783 |
| 208333 | 0.2 | 0.96 | 0.33584 | 0.42 | 0.07342 |
| 133333 | 0.12 | 0.9 | 0.44701 | 0.54 | 0.12678 |
| 122549 | 0.1 | 0.816 | 0.5492 | 0.64 | 0.18707 |
| 134409 | 0.1 | 0.744 | 0.66127 | 0.74 | 0.2644 |
| 406250 | 0.26 | 0.64 | 1 | 1 | 0.5591 |
|  |  |  |  | Lc | 0.1182 |

FIG. 21B

| | | 36 months | | | |
|---|---|---|---|---|---|
| Injection well Inj2 and production wells $P_1.P_6$ - first flood operation | | | | | |
| | Response time ($\tau$) | $f_{ij}$ – intewell connectctivity (steady state) | Equation results with steady state $F_{ij}$ | $f^*_{ij}$ – intewell connectctivity (max duration of the flood) | Equation results with transient $f^*_{ij}$ |
| Producers | Response time Proxy | | Swept Pore Volume Proxy (steady state) | | Swept Pore Volume Proxy (max duration of the flood) |
| $P_1$ | 10 | 0.24 | 173,913 | 0.24 | 173,913 |
| $P_2$ | 50 | 0.12 | 454,545 | 0.11 | 429,030 |
| $P_3$ | 70 | 0.12 | 560,000 | 0.10 | 488,422 |
| $P_4$ | 25 | 0.12 | 208,333 | 0.12 | 207,677 |
| $P_5$ | 15 | 0.20 | 238,095 | 0.20 | 238,079 |
| $P_6$ | 20 | 0.20 | 289,855 | 0.20 | 289,639 |
| | | | 1,924,742 | | 1,826,759 |

FIG. 22A

| | | | 36 months | | |
|---|---|---|---|---|---|
| Injection well Inj2 and production wells $P_1,P_6$ - second flood operation | | | | | |
| | Response time ($\tau$) | fij –intewell connectetivity (steady state) | Equation results with steady state Fij | f*ij –intewell connectetivity (max duration of the flood) | Equation results with transient f*ij |
| Producers | Response time Proxy | | Swept Pore Volume Proxy (steady state) | | Swept Pore Volume Proxy (max duration of the flood) |
| $P_1$ | 45 | 0.14 | 245,000 | 0.13 | 235,013 |
| $P_2$ | 50 | 0.17 | 341,954 | 0.16 | 322,759 |
| $P_3$ | 60 | 0.23 | 503,125 | 0.21 | 457,483 |
| $P_4$ | 50 | 0.15 | 282,258 | 0.14 | 266,414 |
| $P_5$ | 60 | 0.13 | 325,000 | 0.12 | 295,517 |
| $P_6$ | 50 | 0.18 | 350,000 | 0.17 | 330,353 |
| | | | 2,047,337 | | 1,907,537 |

| | | | |
|---|---|---|---|
| Positive change in volumetric sweep (steady state) | 6% | Positive change in volumetric sweep (max duration of the flood) | 4% |

FIG. 22B

First Flood Operation

| Duration | 5 years |
|---|---|
| Compressibility, ct, 1/psi | 0.000006 |

| Producers | P1 | P2 | P3 | P4 | P5 | P6 |
|---|---|---|---|---|---|---|
| Flowing Pressure, psi | 200 | 250 | 100 | 150 | 300 | 200 |

| Injectors | I1 | I2 |
|---|---|---|
| Injection rate, BBls/day | 400 | 500 |
| Flowing Pressure, psi | 1500 | 1350 |

| | Injectors | I1 | I2 |
|---|---|---|---|
| | Well pair pressure drop, psi | $DP_{1j}$ | $DP_{2j}$ |
| Producers | P1 | 1300 | 1150 |
| | P2 | 1250 | 1100 |
| | P3 | 1400 | 1250 |
| | P4 | 1350 | 1200 |
| | P5 | 1200 | 1050 |
| | P6 | 1300 | 1150 |

FIG. 23A

| Injectors | I1 | I2 |
|---|---|---|
| Interwell Connectivities | $f_{1j}$ | $f_{2j}$ |
| P1 | 0.30 | 0.24 |
| P2 | 0.20 | 0.12 |
| P3 | 0.20 | 0.12 |
| P4 | 0.10 | 0.12 |
| P5 | 0.10 | 0.20 |
| P6 | 0.10 | 0.20 |
| Sum of Connectivities | 1 | 1 |

Producers

| Injectors | I1 | I2 |
|---|---|---|
| Interwell time constants | Tau, $t_{1j}$ | Tau, $t_{2j}$ |
| P1 | 10 | 10 |
| P2 | 10 | 50 |
| P3 | 10 | 70 |
| P4 | 50 | 25 |
| P5 | 20 | 15 |
| P6 | 80 | 20 |
|  | 180 | 190 |

Producers

FIG. 23B

| Injectors | I1 | I2 | | Pore Volume associated with the producer |
|---|---|---|---|---|
| Swept pore volume estimate for the first flood, BBls | $Vp_{1j}$ | $Vp_{2j}$ | | |
| P1 | 153,846 | 173,913 | | 327,759 |
| P2 | 106,667 | 454,545 | | 561,212 |
| P3 | 95,238 | 560,000 | | 655,238 |
| P4 | 246,914 | 208,333 | | 455,247 |
| P5 | 111,111 | 238,095 | | 349,206 |
| P6 | 410,256 | 289,855 | | 700,111 |
| Pore Volume associated with the Injector | 1,124,032 | 1,924,742 | | 3,048,774 |
| | | | | Reservoir Pore Volume, BBls |

Producers

FIG. 23C

Second Flood Operation

| Duration | 5 years |
|---|---|
| Compressibility, ct, 1/psi | 0.000006 |

| Producers | P1 | P2 | P3 | P4 | P5 | P6 |
|---|---|---|---|---|---|---|
| Flowing Pressure, psi | 200 | 250 | 100 | 150 | 300 | 200 |

| Injectors | I1 | I2 |
|---|---|---|
| Injection rate, BBls/day | 250 | 350 |
| Flowing Pressure, psi | 1800 | 1700 |

| Injectors | I1 | I2 |
|---|---|---|
| Well pair pressure drop, psi | $DP_{1j}$ | $DP_{2j}$ |
| P1 | 1600 | 1500 |
| P2 | 1550 | 1450 |
| P3 | 1700 | 1600 |
| P4 | 1650 | 1550 |
| P5 | 1500 | 1400 |
| P6 | 1600 | 1500 |

FIG. 23D

| | Injectors | I1 | I2 |
|---|---|---|---|
| Producers | Interwell Connectivities | $f_{1j}$ | $f_{2j}$ |
| | P1 | 0.20 | 0.14 |
| | P2 | 0.10 | 0.17 |
| | P3 | 0.10 | 0.23 |
| | P4 | 0.22 | 0.15 |
| | P5 | 0.12 | 0.13 |
| | P6 | 0.26 | 0.18 |
| Sum of Connectivities | | 1 | 1 |

| | Injectors | I1 | I2 |
|---|---|---|---|
| | Interwell time constants | Tau, $t_{1j}$ | Tau, $t_{2j}$ |
| Producers | P1 | 40 | 45 |
| | P2 | 50 | 50 |
| | P3 | 50 | 60 |
| | P4 | 35 | 50 |
| | P5 | 40 | 60 |
| | P6 | 60 | 50 |
| | | 275 | 315 |

FIG. 23E

| Injectors | I1 | I2 |
|---|---|---|
| Swept pore volume estimate for second flood, BBls | $Vp_{1j}$ | $Vp_{2j}$ |
| P1 | 208,333 | 245,000 |
| P2 | 134,409 | 341,954 |
| P3 | 122,549 | 503,125 |
| P4 | 194,444 | 282,258 |
| P5 | 133,333 | 325,000 |
| P6 | 406,250 | 350,000 |
| Pore Volume associated with the Injector | 1,199,319 | 2,047,337 |

| Pore Volume associated with the producer |
|---|
| 453,333 |
| 476,363 |
| 625,674 |
| 476,703 |
| 458,333 |
| 756,250 |

| 3,246,656 |
|---|
| Reservoir Pore Volume, BBls |

FIG. 23F

| Percentage based on response times | 53% | 66% |
|---|---|---|

| Injectors | I1 | I2 |
|---|---|---|
| percentage change in swept pore volume estimate | $Vp_{1j}$ | $Vp_{2j}$ |
| P1 | 35% | 41% |
| P2 | 26% | -25% |
| P3 | 29% | -10% |
| P4 | -21% | 35% |
| P5 | 20% | 37% |
| P6 | -1% | 21% |

Producers

| Pore Volume associated with the Injector | 7% | 6% |
|---|---|---|

| Pore Volume associated with the producer |
|---|
| 38% |
| -15% |
| -5% |
| 5% |
| 31% |
| 8% |

| 6% |
|---|
| Reservoir Pore Volume, BBls |

FIG. 23G

First Flood Operation

| Duration | 5 years |
|---|---|
| Compressibility, ct, 1/psi | 0.000006 |

| Producers | P1 | P2 | P3 | P4 | P5 | P6 |
|---|---|---|---|---|---|---|
| Flowing Pressure, psi | 200 | 250 | 100 | 150 | 300 | 200 |

| Injectors | I1 | I2 | I3 - zone 1 | I3 - zone 2 |
|---|---|---|---|---|
| Injection rate, Bbls/day | 400 | 500 | 700 | 400 |
| Flowing Pressure, psi | 1500 | 1350 | 1200 | 1400 |

| Injectors | I1 | I2 | I3 - zone 1 | I3 - zone 2 |
|---|---|---|---|---|
| Well pair pressure drop, psi | $DP_{1j}$ | $DP_{2j}$ | $DP_{3j}$ | $DP_{4j}$ |
| P1 | 1300 | 1150 | 1000 | 1200 |
| P2 | 1250 | 1100 | 950 | 1150 |
| P3 | 1400 | 1250 | 1100 | 1300 |
| P4 | 1350 | 1200 | 1050 | 1250 |
| P5 | 1200 | 1050 | 900 | 1100 |
| P6 | 1300 | 1150 | 1000 | 1200 |

(Producers)

FIG. 24A

| Injectors | I1 | I2 | I3 - zone 1 | I3 - zone 2 |
|---|---|---|---|---|
| Interwell Connectivities | $f_{1j}$ | $f_{2j}$ | $f_{3j}$ | $f_{4j}$ |
| P1 | 0.30 | 0.19 | 0.10 | 0.33 |
| P2 | 0.20 | 0.12 | 0.11 | 0.16 |
| P3 | 0.20 | 0.12 | 0.16 | 0.14 |
| P4 | 0.10 | 0.17 | 0.17 | 0.12 |
| P5 | 0.10 | 0.20 | 0.23 | 0.09 |
| P6 | 0.10 | 0.20 | 0.23 | 0.16 |
| Sum of Connectivities | 1 | 1 | 1 | 1 |

(Producers)

| Injectors | I1 | I2 | I3 - zone 1 | I3 - zone 2 |
|---|---|---|---|---|
| Interwell time constants | Tau, $\tau_{1j}$ | Tau, $\tau_{2j}$ | Tau, $\tau_{3j}$ | Tau, $\tau_{4j}$ |
| P1 | 10 | 10 | 43 | 28 |
| P2 | 10 | 31 | 10 | 30 |
| P3 | 10 | 31 | 42 | 32 |
| P4 | 50 | 29 | 22 | 16 |
| P5 | 20 | 49 | 18 | 28 |
| P6 | 80 | 17 | 31 | 50 |

FIG. 24B

| Injectors | I1 | I2 | I3 - zone 1 | I3 - zone 2 | Pore Volume associated with the producer |
|---|---|---|---|---|---|
| Swept pore volume estimate for the first flood, BBls | $Vp_{1j}$ | $Vp_{2j}$ | $Vp_{3j}$ | $Vp_{4j}$ | |
| P1 | 153,846 | 135,745 | 508,731 | 505,698 | 1,304,021 |
| P2 | 106,667 | 292,546 | 132,460 | 279,163 | 810,836 |
| P3 | 95,238 | 255,340 | 716,283 | 231,655 | 1,298,515 |
| P4 | 246,914 | 335,462 | 413,539 | 101,342 | 1,097,256 |
| P5 | 111,111 | 772,644 | 527,531 | 156,102 | 1,567,388 |
| P6 | 410,256 | 245,512 | 848,736 | 451,322 | 1,955,827 |
| Pore Volume associated with the Injector | 1,124,032 | 2,037,249 | 3,147,280 | 1,725,282 | 8,033,843 Reservoir Pore Volume, BBls |

FIG. 24C

Second Flood Operation

| Duration | 5 years |
|---|---|
| Compressibility, ct, 1/psi | 0.000006 |

| Producers | P1 | P2 | P3 | P4 | P5 | P6 |
|---|---|---|---|---|---|---|
| Flowing Pressure, psi | 200 | 250 | 100 | 150 | 300 | 200 |

| Injectors | I1 | I2 | I3 - zone 1 | I3 - zone 2 |
|---|---|---|---|---|
| Injection rate, BBls/day | 350 | 500 | 700 | 400 |
| Flowing Pressure, psi | 1800 | 1350 | 1200 | 1400 |

| | Injectors | I1 | I2 | I3 - zone 1 | I3 - zone 2 |
|---|---|---|---|---|---|
| | Well pair pressure drop, psi | $DP_{1j}$ | $DP_{2j}$ | $DP_{3j}$ | $DP_{4j}$ |
| Producers | P1 | 1600 | 1150 | 1000 | 1200 |
| | P2 | 1550 | 1100 | 950 | 1150 |
| | P3 | 1700 | 1250 | 1100 | 1300 |
| | P4 | 1650 | 1200 | 1050 | 1250 |
| | P5 | 1500 | 1050 | 900 | 1100 |
| | P6 | 1600 | 1150 | 1000 | 1200 |

FIG. 24D

| Injectors | I1 | I2 | I3 - zone 1 | I3 - zone 2 |
|---|---|---|---|---|
| Interwell Connectivities | $f_{1j}$ | $f_{2j}$ | $f_{3j}$ | $f_{4j}$ |
| P1 | 0.25 | 0.19 | 0.10 | 0.33 |
| P2 | 0.15 | 0.12 | 0.11 | 0.16 |
| P3 | 0.15 | 0.12 | 0.16 | 0.14 |
| P4 | 0.18 | 0.17 | 0.17 | 0.12 |
| P5 | 0.12 | 0.20 | 0.23 | 0.09 |
| P6 | 0.15 | 0.20 | 0.23 | 0.16 |
| Sum of Connectivities | 1 | 1 | 1 | 1 |

(Producers)

| Injectors | I1 | I2 | I3 - zone 1 | I3 - zone 2 |
|---|---|---|---|---|
| Interwell time constants | Tau, $\tau_{1j}$ | Tau, $\tau_{2j}$ | Tau, $\tau_{3j}$ | Tau, $\tau_{4j}$ |
| P1 | 30 | 10 | 43 | 28 |
| P2 | 30 | 31 | 10 | 30 |
| P3 | 30 | 31 | 42 | 32 |
| P4 | 20 | 29 | 22 | 16 |
| P5 | 30 | 49 | 18 | 28 |
| P6 | 60 | 17 | 31 | 50 |

(Producers)

FIG. 24E

| Injectors | | I1 | I2 | I3 - zone 1 | I3 - zone 2 | | Pore Volume associated with the producer |
|---|---|---|---|---|---|---|---|
| | Swept pore volume estimate for second flood, BBls | $Vp_{1j}$ | $Vp_{2j}$ | $Vp_{3j}$ | $Vp_{4j}$ | | |
| Producers | P1 | 273,438 | 135,745 | 508,731 | 505,698 | | 1,423,613 |
| | P2 | 169,355 | 292,546 | 132,460 | 279,163 | | 873,524 |
| | P3 | 154,412 | 255,340 | 716,283 | 231,655 | | 1,357,689 |
| | P4 | 127,273 | 335,462 | 413,539 | 101,342 | | 977,615 |
| | P5 | 140,000 | 772,644 | 527,531 | 156,102 | | 1,596,277 |
| | P6 | 328,125 | 245,512 | 848,736 | 451,322 | | 1,873,695 |
| Pore Volume associated with the Injector | | 1,192,602 | 2,037,249 | 3,147,280 | 1,725,282 | | 8,102,413 |
| | | | | | | | Reservoir Pore Volume, BBls |

FIG. 24F

2700 receiving production data for the at least one production well and injection data for the at least one injection well for the polymer flood operation 2702 running capacitance resistance modeling using the received production data and the received injection data for the polymer flood operation to generate a response time and an interwell connectivity per injection well and production well pair for the polymer flood operation, wherein running capacitance resistance modeling includes accounting for rheology of the polymer used in the polymer flood operation in the running of the capacitance resistance modeling (optionally – allowed connections) 2704 where accounting for the rheology in running capacitance resistance modeling includes separating each injection well and production well pair of the polymer flood operation into at least three tanks, wherein the three tanks include a near injection well tank, a near production well tank, and a middle tank between the near injection well tank and the near production well tank 2706 where the production data includes production rate and flowing pressure data as a function of time, and wherein the injection data includes injection rate and flowing pressure data as a function of time, and where accounting for the rheology in running capacitance resistance modeling includes using (i) material balance equations for each of the tanks, (ii) the injection and production rates, (iii) the injection and production flowing pressure data, and (iv) a polymer rheology 2708 where accounting for the rheology in running capacitance resistance modeling includes using a capacitance resistance modeling polymer formulation 2710

FIG. 27

(i) loading or receiving well locations, reservoir boundary, and injection and production rate histories (ii) creating producer-centered (e.g., Voronoi) polygons based on the producer locations and the reservoir boundary (or any fault, etc.)

(iii) calculating the area ($A_i$) (e.g., drainage area, pore volume, proxy of OOIP, etc.) covered by each polygon associated with each producer based on geometry (or the geological boundary) of the polygon (iv) for each producer, calculating cumulative oil production ($Q_i$) and rank producers from largest Q to smallest Q (v) for each producer, calculating cumulative oil production ($Q_i$) and a ratio between $Q_i$ and $A_i$ (vi) ranking the producers from the smallest to largest Q/A ratio (vii) calculating a norm area (or Pore volume) and norm cumulative oil production in that reservoir (viii) calculating an index of uneven sweep (IUS) of the reservoir (viii) repeating (i)-(viii) for another reservoir, and ranking the reservoir for infill drilling opportunity with the largest IUS

(i) loading or receiving well locations, and injection and production rate histories for all wells (ii) creating polygons (e.g., streamgrid polygons) based on the well locations (iii) calculating allocation factors for injector and producers based on any available allocation method (e.g., injection angle, producer angle)

(iv) calculating the allocated water injection and water production within each polygon (e.g., streamgrid polygon) (between connected injector-producer pair)

(v) calculating water cycling between connected injector-producer pair for each polygon (e.g., streamgrid polygon)

(vi) defining a threshold for water cycling based on a distribution (vii) identifying at least one polygon (e.g., streamgrid polygon) that have water cycling above the threshold and convert the producer in that polygon (e.g., streamgrid polygon) for pattern realignment

FIG. 30A

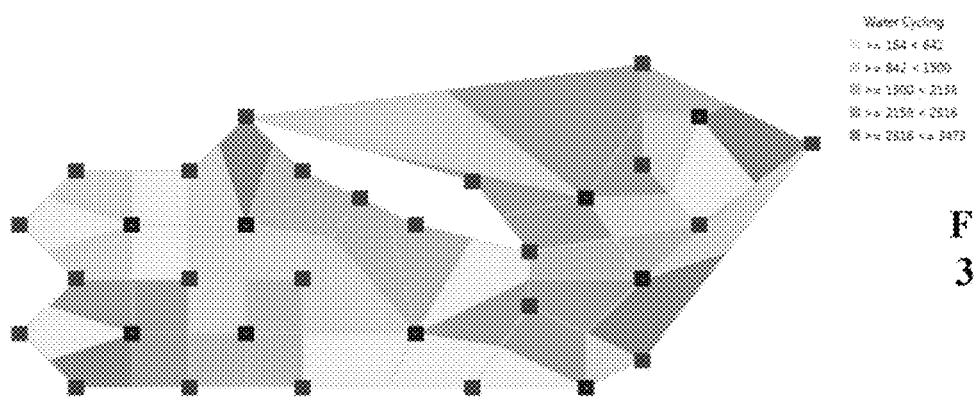

FIG. 30B

|  |  |  |  |  | Threshold | 3000 |  |
|---|---|---|---|---|---|---|---|
| Streamgrid | AF - Injector Angle | AF - Producer Angle | Water Inj (bbl/d) | Water Prod (bbl/d) | Water Cycling |  | Producer to be converted |
| E01->A08 | 0.25 | 0.25 | 1859 | 377 | 2236 |  |  |
| E01->A07 | 0.2 | 0.5 | 1478 | 694 | 2172 |  |  |
| E01->A02 | 0.2 | 1 | 1478 | 1965 | 3443 | X | A02 |
| J06->B10ST1 | 0.16 | 0.27 | 195 | 181 | 376 |  |  |
| J06->B09 | 0.22 | 0.8 | 263 | 2863 | 3127 | X | B09 |
| J06->B07 | 0.42 | 0.44 | 509 | 1218 | 1727 |  |  |
| E09->A12ST1-LAT1 | 0.25 | 0.4 | 449 | 287 | 737 |  |  |
| E09->A08 | 0.25 | 0.25 | 449 | 377 | 826 |  |  |
| J01->B04 | 0.09 | 0.32 | 155 | 556 | 711 |  |  |
| J01->B03 | 0.12 | 1 | 195 | 1953 | 2148 |  |  |
| J01->A09 | 0.14 | 0.41 | 228 | 717 | 945 |  |  |
| J06->B11 | 0.21 | 0.38 | 250 | 861 | 1110 |  |  |
| J01->A05 | 0.18 | 0.5 | 293 | 467 | 760 |  |  |
| J03->B10ST1 | 0.23 | 0.58 | 1468 | 394 | 1862 |  |  |
| J03->B08 | 0.43 | 0.65 | 2730 | 615 | 3346 | X | B08 |
| J02->B07 | 0.23 | 0.56 | 1187 | 1573 | 2760 |  |  |
| J02->B05 | 0.07 | 1 | 364 | 2251 | 2615 |  |  |
| J02->B04 | 0.31 | 0.37 | 1559 | 631 | 2190 |  |  |
| J02->B10ST1 | 0.16 | 0.16 | 821 | 109 | 930 |  |  |
| J03->B04 | 0.16 | 0.31 | 1002 | 531 | 1533 |  |  |
| J01->B06 | 0.1 | 0.41 | 166 | 2244 | 2410 |  |  |
| J03->B06 | 0.12 | 0.32 | 801 | 1788 | 2589 |  |  |
| J04->B08 | 0.41 | 0.35 | 1091 | 326 | 1417 |  |  |
| J04->B06 | 0.41 | 0.27 | 1091 | 1490 | 2580 |  |  |
| J02->B11 | 0.15 | 0.62 | 779 | 1389 | 2168 |  |  |
| E09->A11 | 0.2 | 1 | 357 | 539 | 897 |  |  |
| E09->A06 | 0.1 | 1 | 184 | 0 | 184 |  |  |
| E02->A05 | 0.25 | 0.5 | 1112 | 467 | 1579 |  |  |
| E02->A03 | 0.25 | 0.5 | 1112 | 823 | 1934 |  |  |
| E01->A03 | 0.25 | 0.5 | 1859 | 823 | 2682 |  |  |
| E09->A07 | 0.2 | 0.5 | 357 | 694 | 1051 |  |  |
| E04->A13 | 0.12 | 1 | 460 | 1188 | 1648 |  |  |
| E04->A12ST1-LAT1 | 0.2 | 0.6 | 732 | 431 | 1163 |  |  |
| E04->A08 | 0.25 | 0.25 | 920 | 377 | 1297 |  |  |
| E04->A09 | 0.22 | 0.34 | 823 | 606 | 1430 |  |  |
| J01->B12D | 0.3 | 0.69 | 494 | 0 | 494 |  |  |
| J04->B12D | 0.17 | 0.31 | 457 | 0 | 457 |  |  |
| E02->A09 | 0.25 | 0.25 | 1112 | 441 | 1553 |  |  |
| E02->A08 | 0.25 | 0.25 | 1112 | 377 | 1488 |  |  |
| E01->A04 | 0.1 | 1 | 762 | 0 | 762 |  |  |
| J03->B09 | 0.06 | 0.2 | 405 | 734 | 1139 |  |  |
| J02->B01 | 0.07 | 0.22 | 366 | 854 | 1221 |  |  |
| E04->B01 | 0.1 | 0.78 | 377 | 3097 | 3473 | X | B01 |
| J01->B02 | 0.08 | 0.54 | 129 | 1593 | 1722 |  |  |
| E04->B02 | 0.1 | 0.46 | 368 | 1359 | 1727 |  |  |

FIG. 30C

| Streamgrid | AF - Injector Angle | AF - Number of Producers | AF - Injector Area |
|---|---|---|---|
| E01->A08 | 0.25 | 0.2 | 0.2 |
| E01->A07 | 0.2 | 0.2 | 0.2 |
| E01->A02 | 0.2 | 0.2 | 0.2 |
| J06->B10ST3 | 0.16 | 0.25 | 0.32 |
| J06->B09 | 0.22 | 0.25 | 0.29 |
| J06->B07 | 0.42 | 0.25 | 0.18 |
| E09->A12ST | 0.25 | 0.2 | 0.2 |
| E09->A08 | 0.25 | 0.2 | 0.2 |
| J01->B04 | 0.09 | 0.14 | 0.14 |
| J01->B03 | 0.12 | 0.14 | 0.14 |
| J01->A09 | 0.14 | 0.14 | 0.19 |
| J06->B11 | 0.21 | 0.25 | 0.21 |
| J01->A05 | 0.18 | 0.14 | 0.16 |
| J03->B10ST3 | 0.23 | 0.2 | 0.12 |
| J03->B08 | 0.43 | 0.2 | 0.3 |
| J02->B07 | 0.23 | 0.17 | 0.35 |
| J02->B05 | 0.07 | 0.17 | 0.07 |
| J02->B04 | 0.31 | 0.17 | 0.09 |
| J02->B10ST3 | 0.16 | 0.17 | 0.08 |
| J03->B04 | 0.16 | 0.2 | 0.18 |
| J01->B06 | 0.1 | 0.14 | 0.1 |
| J03->B06 | 0.12 | 0.2 | 0.2 |
| J04->B08 | 0.41 | 0.33 | 0.2 |
| J04->B06 | 0.41 | 0.33 | 0.5 |
| J02->B11 | 0.15 | 0.17 | 0.07 |
| E09->A11 | 0.2 | 0.2 | 0.2 |
| E09->A06 | 0.1 | 0.2 | 0.2 |
| E02->A05 | 0.25 | 0.25 | 0.25 |
| E02->A03 | 0.25 | 0.25 | 0.25 |
| E01->A03 | 0.25 | 0.2 | 0.2 |
| E09->A07 | 0.2 | 0.2 | 0.2 |
| E04->A13 | 0.12 | 0.17 | 0.15 |
| E04->A12ST | 0.2 | 0.17 | 0.17 |
| E04->A08 | 0.25 | 0.17 | 0.17 |
| E04->A09 | 0.22 | 0.17 | 0.19 |
| J01->B12D | 0.3 | 0.14 | 0.13 |
| J04->B12D | 0.17 | 0.33 | 0.3 |
| E02->A09 | 0.25 | 0.25 | 0.25 |
| E02->A08 | 0.25 | 0.25 | 0.25 |
| E01->A04 | 0.1 | 0.2 | 0.2 |
| J03->B09 | 0.06 | 0.2 | 0.2 |
| J02->B01 | 0.07 | 0.17 | 0.34 |
| E04->B01 | 0.1 | 0.17 | 0.17 |
| J01->B02 | 0.08 | 0.14 | 0.14 |
| E04->B02 | 0.1 | 0.17 | 0.17 |

(i) for any given zone of a reservoir, getting a reservoir boundary in that zone and calculating its total area (St)

(ii) getting contact point of all wells that penetrate and are perforated in that zone (iii) creating streamgrid with the well-zone contact locations (iv) calculating the total area (S) covered by populated streamgrids (v) estimating maximal areal sweep efficiency in that zone, which equals S/St repeating (i)-(v) for all zones in a reservoir and getting the S and St for each zone, calculate the ratio between summation of S from all zones and summation of St from all zones to get the maximum areal sweep efficiency for the reservoir

FIG. 32A

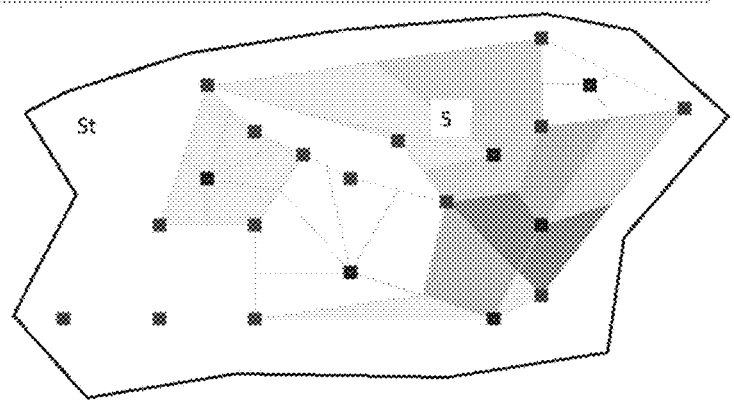

FIG. 32B

| Streamgrid | Zone 1 Area (acres) | Zone2 | Zone 3 | Zone 4 | |
|---|---|---|---|---|---|
| J02->B05 | 54 | | | | |
| J02->B04 | 74 | | | | |
| J02->B11 | 62 | | | | |
| J02->B07 | 284 | | | | |
| J03->B08 | 93 | | | | |
| J04->B08 | 23 | | | | |
| J03->B09 | 167 | | | | |
| J03->B11 | 130 | | | | |
| J03->B04 | 108 | | | | |
| J04->B04 | 170 | | | | |
| E04->B01 | 62 | | | | |
| E04->A13 | 54 | | | | |
| E04->A08 | 62 | | | | |
| E04->A09 | 69 | | | | |
| J01->B03 | 93 | | | | |
| J01->A09 | 124 | | | | |
| J01->B04 | 162 | | | | |
| J01->A05 | 139 | | | | |
| J04->A05 | 77 | | | | |
| J06->B11 | 65 | | | | |
| J06->B09 | 59 | | | | |
| J06->B07 | 53 | | | | |
| J02->B01 | 273 | | | | |
| E04->B02 | 62 | | | | |
| J01->B02 | 93 | | | | |
| | | | | | |
| Sum (S) | 2612 | 343 | 1324 | 3542 | |
| St | 4965 | 902 | 3029 | 6980 | |
| Max Area Sweep by zone | 0.53 | | | | |
| Max Areal Sweep for Reservoir | | | | | 0.49 |

FIG. 32C for a first injection well  3300

```
┌─────────────────────────────────────────────────────────────────────────┐
│ receiving injection rate data for the first injection well and          │
│ production rate data for at least one production well communicating     │
│ with the injection well 3302                                            │
└─────────────────────────────────────────────────────────────────────────┘
                                    ↓
┌─────────────────────────────────────────────────────────────────────────┐
│ running capacitance resistance modeling using the received data to      │
│ generate an interwell connectivity for each injection well and          │
│ production well pair 3304                                               │
└─────────────────────────────────────────────────────────────────────────┘
                                    ↓
┌─────────────────────────────────────────────────────────────────────────┐
│ receiving injection rate data for the first injection well and          │
│ production rate data for at least one production well communicating     │
│ with the injection well 3306                                            │
└─────────────────────────────────────────────────────────────────────────┘
                                    ↓
┌─────────────────────────────────────────────────────────────────────────┐
│ determining a value of injected fluid for each injection well and       │
│ production well pair using the generated interwell connectivity for     │
│ the well pair and an oil-cut value for the production well of the       │
│ pair 3308                                                               │
└─────────────────────────────────────────────────────────────────────────┘
                                    ↓
┌─────────────────────────────────────────────────────────────────────────┐
│ aggregating the generated values of injected fluid per pair to          │
│ determine a value of injected fluid for the first injection well 3310   │
└─────────────────────────────────────────────────────────────────────────┘
                                    ↓
┌─────────────────────────────────────────────────────────────────────────┐
│ ranking the first injection well and the at least one other injection   │
│ well based on the values of injected fluid 3312                         │
└─────────────────────────────────────────────────────────────────────────┘
                                    ↓
┌─────────────────────────────────────────────────────────────────────────┐
│ generating a net value of injected fluid for the first injection well   │
│ and the at least one other injection well 3314                          │
└─────────────────────────────────────────────────────────────────────────┘
                                    ↓
┌─────────────────────────────────────────────────────────────────────────┐
│ reranking the first injection well and the at least one other           │
│ injection well based the net values of injected fluid 3316              │
└─────────────────────────────────────────────────────────────────────────┘
                                    ↓
┌─────────────────────────────────────────────────────────────────────────┐
│ generating a recommendation 3318                                        │
└─────────────────────────────────────────────────────────────────────────┘
```

FIG. 33

3400 receiving injection profile data (ILT) and injection rates using the received injection profile data and injection rates to split each injection well into multiple zonal level injectors running capacitance resistance modeling treating each zonal level injector as a single injector, wherein running capacitance resistance modeling includes generating interwell connectivities at the zonal level determining if there is crossflow between at least two zones.

generating at least one PLT.

generating continuous production profile (PLT)

interpolating for PLT, ILT, or both

FIG. 34

| Date | Injection Rate I1 | Injection Profile | | Zonal Injection Rate | | Production Rate History | |
|---|---|---|---|---|---|---|---|
| | | ILT I1-Z1 | ILT I1-Z2 | Injection - I1Z1 | Injection - I1Z2 | Producer P2 | Producer P3 |
| 1/1/2000 | 4490 | 41 | 59 | 1840.9 | 2649.1 | 1428 | 3062 |
| 2/1/2000 | 1090 | 45 | 55 | 490.5 | 599.5 | 338 | 752 |
| 3/1/2000 | 2530 | 20 | 80 | 506 | 2024 | 911 | 1619 |
| 4/1/2000 | 2950 | 92 | 8 | 2714 | 236 | 636 | 2313 |
| 5/1/2000 | 2050 | 51 | 49 | 1045.5 | 1004.5 | 611 | 1439 |
| 6/1/2000 | 4040 | 91 | 9 | 3676.4 | 363.6 | 880 | 3159 |
| 7/1/2000 | 3010 | 32 | 68 | 963.2 | 2046.8 | 1011 | 1999 |
| 8/1/2000 | 3640 | 2 | 98 | 72.8 | 3567.2 | 1441 | 2199 |
| 9/1/2000 | 2960 | 67 | 33 | 1983.2 | 976.8 | 787 | 2173 |
| 10/1/2000 | 3230 | 73 | 27 | 2357.9 | 872.1 | 820 | 2410 |
| 11/1/2000 | 4420 | 53 | 47 | 2342.6 | 2077.4 | 1299 | 3121 |
| 12/1/2000 | 2290 | 44 | 56 | 1007.6 | 1282.4 | 714 | 1576 |
| 1/1/2001 | 4080 | 4 | 96 | 163.2 | 3916.8 | 1599 | 2481 |
| 2/1/2001 | 4880 | 56 | 44 | 2732.8 | 2147.2 | 1405 | 3475 |
| 3/1/2001 | 2280 | 33 | 67 | 752.4 | 1527.6 | 761 | 1518 |
| 4/1/2001 | 1980 | 61 | 39 | 1207.8 | 772.2 | 550 | 1430 |
| 5/1/2001 | 4710 | 6 | 94 | 282.6 | 4427.4 | 1827 | 2883 |
| 6/1/2001 | 4530 | 75 | 25 | 3397.5 | 1132.5 | 1132 | 3398 |

FIG. 35A

| | | No Primary, No PLT dat | CRM Connectivity - fij | | | |
|---|---|---|---|---|---|---|
| | | 1 injector | I1Z1-P2 | I1Z2-P2 | I1Z1-P3 | I1Z2-P3 |
| | | 2 producers | 0.2 | 0.4 | 0.8 | 0.6 |
| | | 2 zones | | | | |
| CRM Production Rate Estimates after history matching and obtaining connectivities at zonal level | | | Secondary flux at zone level (qij = Injection rate by zone multiplied by connectivity @ zone 1 and 2) | | | |
| CRM P2 | CRM P3 | | I1Z1-P2 | I1Z2-P2 | I1Z1-P3 | I1Z2-P3 |
| 1514 | 3342 | | 368 | 1060 | 1473 | 1589 |
| 345 | 808 | | 98 | 240 | 392 | 360 |
| 937 | 1780 | | 101 | 810 | 405 | 1214 |
| 677 | 2512 | | 542 | 94 | 2171 | 142 |
| 624 | 1537 | | 209 | 402 | 836 | 603 |
| 928 | 3190 | | 735 | 145 | 2941 | 218 |
| 1079 | 2107 | | 192 | 819 | 771 | 1228 |
| 1489 | 2414 | | 14 | 1427 | 58 | 2140 |
| 848 | 2348 | | 396 | 391 | 1587 | 586 |
| 852 | 2429 | | 471 | 349 | 1886 | 523 |
| 1374 | 3367 | | 468 | 831 | 1874 | 1246 |
| 751 | 1727 | | 201 | 513 | 806 | 769 |
| 1642 | 2599 | | 32 | 1567 | 131 | 2350 |
| 1469 | 3741 | | 546 | 859 | 2186 | 1288 |
| 762 | 1555 | | 150 | 611 | 602 | 917 |
| 600 | 1536 | | 241 | 309 | 966 | 463 |
| 1860 | 3123 | FIG. 35B | 56 | 1771 | 226 | 2656 |
| 1244 | 3686 | | 679 | 453 | 2718 | 680 |

| Initial Production | 0 | 0 | | | |
|---|---|---|---|---|---|
| Decline | 0.3 | 0.2 | | | |

| Zonal CRM Generated Continous PLT Estimates | | | | | |
|---|---|---|---|---|---|
| Z1-P2 | Z2-P2 | check = 1 | Z1-P3 | Z2-P3 | Check =1 |
| 0.26 | 0.74 | 1.00 | 0.48 | 0.52 | 1.00 |
| 0.29 | 0.71 | 1.00 | 0.52 | 0.48 | 1.00 |
| 0.11 | 0.89 | 1.00 | 0.25 | 0.75 | 1.00 |
| 0.85 | 0.15 | 1.00 | 0.94 | 0.06 | 1.00 |
| 0.34 | 0.66 | 1.00 | 0.58 | 0.42 | 1.00 |
| 0.83 | 0.17 | 1.00 | 0.93 | 0.07 | 1.00 |
| 0.19 | 0.81 | 1.00 | 0.39 | 0.61 | 1.00 |
| 0.01 | 0.99 | 1.00 | 0.03 | 0.97 | 1.00 |
| 0.50 | 0.50 | 1.00 | 0.73 | 0.27 | 1.00 |
| 0.57 | 0.43 | 1.00 | 0.78 | 0.22 | 1.00 |
| 0.36 | 0.64 | 1.00 | 0.60 | 0.40 | 1.00 |
| 0.28 | 0.72 | 1.00 | 0.51 | 0.49 | 1.00 |
| 0.02 | 0.98 | 1.00 | 0.05 | 0.95 | 1.00 |
| 0.39 | 0.61 | 1.00 | 0.63 | 0.37 | 1.00 |
| 0.20 | 0.80 | 1.00 | 0.40 | 0.60 | 1.00 |
| 0.44 | 0.56 | 1.00 | 0.68 | 0.32 | 1.00 |
| 0.03 | 0.97 | 1.00 | 0.08 | 0.92 | 1.00 |
| 0.60 | 0.40 | 1.00 | 0.80 | 0.20 | 1.00 |

FIG. 35C

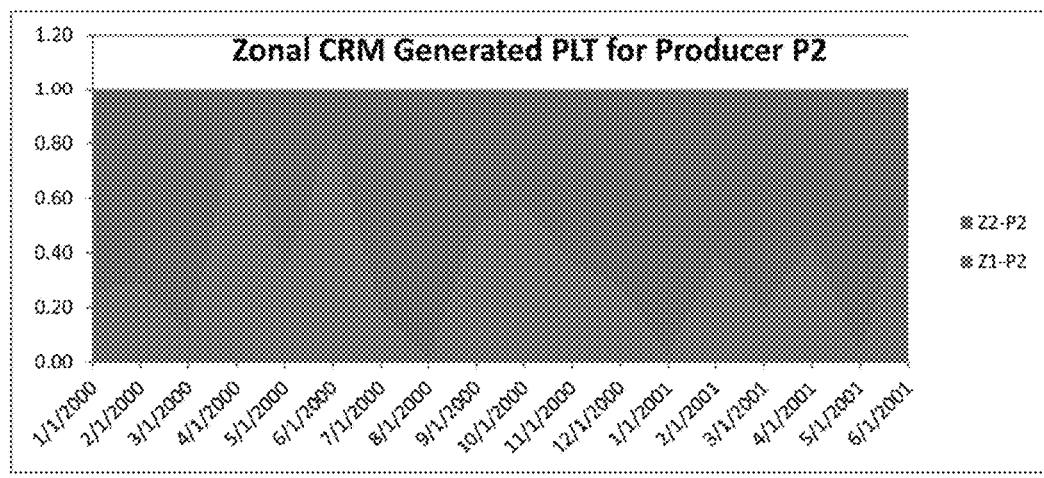
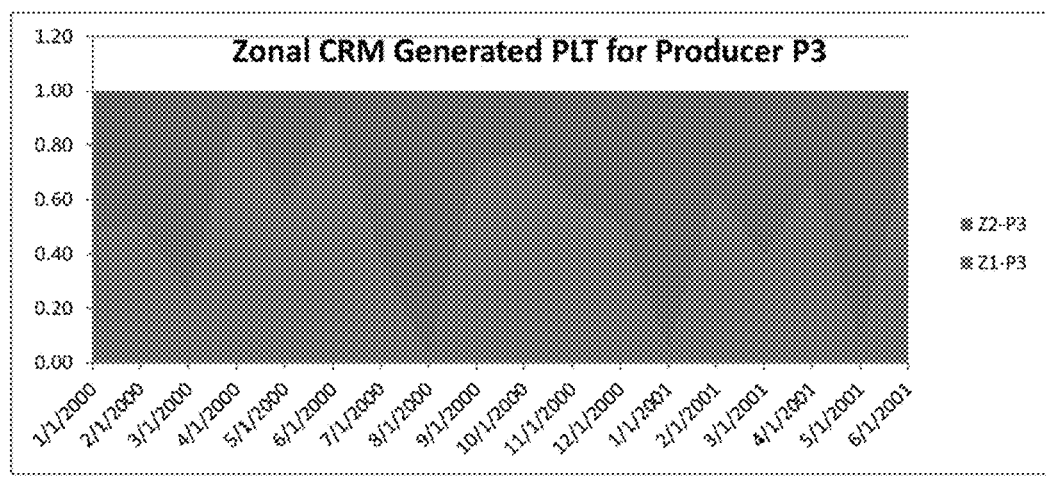
FIG. 35E

|    | Date      | Injection Rate I1 | Injection Profile ILT I1-Z1 | ILT I1-Z2 | Zonal Injection Rate Injection - I1Z1 | Injection - I1Z2 | Production Rate History Producer P2 | Producer P3 |
|----|-----------|-------------------|------------------------------|-----------|----------------------------------------|------------------|--------------------------------------|-------------|
| 1  | 1/1/2000  | 4490              | 41                           | 59        | 1840.9                                 | 2649.1           | 2168                                 | 3717        |
| 2  | 2/1/2000  | 1090              | 45                           | 55        | 490.5                                  | 599.5            | 887                                  | 1288        |
| 3  | 3/1/2000  | 2530              | 20                           | 80        | 506                                    | 2024             | 1317                                 | 2058        |
| 4  | 4/1/2000  | 2950              | 92                           | 8         | 2714                                   | 236              | 938                                  | 2672        |
| 5  | 5/1/2000  | 2050              | 51                           | 49        | 1045.5                                 | 1004.5           | 834                                  | 1733        |
| 6  | 6/1/2000  | 4040              | 91                           | 9         | 3676.4                                 | 363.6            | 1046                                 | 3400        |
| 7  | 7/1/2000  | 3010              | 32                           | 68        | 963.2                                  | 2046.8           | 1133                                 | 2196        |
| 8  | 8/1/2000  | 3640              | 2                            | 98        | 72.8                                   | 3567.2           | 1532                                 | 2360        |
| 9  | 9/1/2000  | 2960              | 67                           | 33        | 1983.2                                 | 976.8            | 854                                  | 2305        |
| 10 | 10/1/2000 | 3230              | 73                           | 27        | 2357.9                                 | 872.1            | 870                                  | 2518        |
| 11 | 11/1/2000 | 4420              | 53                           | 47        | 2342.6                                 | 2077.4           | 1336                                 | 3209        |
| 12 | 12/1/2000 | 2290              | 44                           | 56        | 1007.6                                 | 1282.4           | 741                                  | 1648        |
| 13 | 1/1/2001  | 4080              | 4                            | 96        | 163.2                                  | 3916.8           | 1619                                 | 2540        |
| 14 | 2/1/2001  | 4880              | 56                           | 44        | 2732.8                                 | 2147.2           | 1420                                 | 3523        |
| 15 | 3/1/2001  | 2280              | 33                           | 67        | 752.4                                  | 1527.6           | 772                                  | 1558        |
| 16 | 4/1/2001  | 1980              | 61                           | 39        | 1207.8                                 | 772.2            | 558                                  | 1462        |
| 17 | 5/1/2001  | 4710              | 6                            | 94        | 282.6                                  | 4427.4           | 1833                                 | 2909        |
| 18 | 6/1/2001  | 4530              | 75                           | 25        | 3397.5                                 | 1132.5           | 1137                                 | 3419        |

FIG. 36A

| CRM Production Rate Estimates after history matching and obtaining connectivities at zonal level | | Secondary flux at zone level (qij = Injection rate by zone multiplied by connectivity @ zone 1 and 2) | | | | CRM Estimates of Primary Produ | |
|---|---|---|---|---|---|---|---|
| CRM P2 | CRM P3 | I1Z1-P2 | I1Z2-P2 | I1Z1-P3 | I1Z2-P3 | CRM P2 | CRM P3 |
| 2233 | 3962 | 368 | 1060 | 1473 | 1589 | 805 | 900 |
| 928 | 1304 | 98 | 240 | 392 | 360 | 590 | 552 |
| 1405 | 2181 | 101 | 810 | 405 | 1214 | 494 | 562 |
| 969 | 2735 | 542 | 94 | 2171 | 142 | 332 | 422 |
| 868 | 1815 | 209 | 402 | 836 | 603 | 257 | 376 |
| 1145 | 3426 | 735 | 145 | 2941 | 218 | 264 | 267 |
| 1148 | 2283 | 192 | 819 | 771 | 1228 | 138 | 284 |
| 1619 | 2396 | 14 | 1427 | 58 | 2140 | 179 | 197 |
| 871 | 2525 | 396 | 391 | 1587 | 586 | 84 | 353 |
| 915 | 2641 | 471 | 349 | 1886 | 523 | 95 | 231 |
| 1368 | 3219 | 468 | 831 | 1874 | 1246 | 69 | 98 |
| 782 | 1700 | 201 | 513 | 806 | 769 | 68 | 125 |
| 1758 | 2700 | 32 | 1567 | 131 | 2350 | 160 | 219 |
| 1505 | 3594 | 546 | 859 | 2186 | 1288 | 100 | 120 |
| 808 | 1640 | 150 | 611 | 602 | 917 | 47 | 122 |
| 591 | 1585 | 241 | 309 | 966 | 463 | 41 | 156 |
| 1843 | 3106 | 56 | 1771 | 226 | 2656 | 16 | 224 |
| 1173 | 3593 | 679 | 453 | 2718 | 680 | 41 | 196 |

FIG. 36B

| Primary | | | | Secondary recovery portion | | | | | |
|---|---|---|---|---|---|---|---|---|---|
| Zonal CRM Generated Continous PLT Estimates | | | | Zonal CRM Generated Continous PLT Estimates | | | | | |
| Z1-P2 | Z2-P2 | Z1-P3 | Z2-P3 | Z1-P2 | Z2-P2 | check = 1 | Z1-P3 | Z2-P3 | Check =1 |
| 309 | 496 | 170 | 729 | 0.26 | 0.74 | 1.00 | 0.48 | 0.52 | 1.00 |
| 227 | 363 | 104 | 448 | 0.29 | 0.71 | 1.00 | 0.52 | 0.48 | 1.00 |
| 190 | 304 | 106 | 456 | 0.11 | 0.89 | 1.00 | 0.25 | 0.75 | 1.00 |
| 128 | 205 | 80 | 342 | 0.85 | 0.15 | 1.00 | 0.94 | 0.06 | 1.00 |
| 99 | 158 | 71 | 305 | 0.34 | 0.66 | 1.00 | 0.58 | 0.42 | 1.00 |
| 102 | 163 | 51 | 216 | 0.83 | 0.17 | 1.00 | 0.93 | 0.07 | 1.00 |
| 53 | 85 | 54 | 231 | 0.19 | 0.81 | 1.00 | 0.39 | 0.61 | 1.00 |
| 69 | 110 | 37 | 160 | 0.01 | 0.99 | 1.00 | 0.03 | 0.97 | 1.00 |
| 32 | 52 | 67 | 286 | 0.50 | 0.50 | 1.00 | 0.73 | 0.27 | 1.00 |
| 37 | 59 | 44 | 187 | 0.57 | 0.43 | 1.00 | 0.78 | 0.22 | 1.00 |
| 26 | 42 | 19 | 79 | 0.36 | 0.64 | 1.00 | 0.60 | 0.40 | 1.00 |
| 26 | 42 | 24 | 101 | 0.28 | 0.72 | 1.00 | 0.51 | 0.49 | 1.00 |
| 61 | 98 | 41 | 178 | 0.02 | 0.98 | 1.00 | 0.05 | 0.95 | 1.00 |
| 38 | 61 | 23 | 97 | 0.39 | 0.61 | 1.00 | 0.63 | 0.37 | 1.00 |
| 18 | 29 | 23 | 99 | 0.20 | 0.80 | 1.00 | 0.40 | 0.60 | 1.00 |
| 16 | 25 | 30 | 126 | 0.44 | 0.56 | 1.00 | 0.68 | 0.32 | 1.00 |
| 6 | 10 | 42 | 181 | 0.03 | 0.97 | 1.00 | 0.08 | 0.92 | 1.00 |
| 16 | 25 | 37 | 159 | 0.60 | 0.40 | 1.00 | 0.80 | 0.20 | 1.00 |

FIG. 36C

| Time | CRM PLT Estimates (Primary + Secondary) | | | | | |
|---|---|---|---|---|---|---|
| | Z1-P2 | Z2-P2 | check = 1 | Z1-P3 | Z2-P3 | Check =1 |
| 1/1/2000 | 0.30 | 0.70 | | 0.41 | 0.59 | |
| 2/1/2000 | 0.35 | 0.65 | | 0.38 | 0.62 | |
| 3/1/2000 | 0.21 | 0.79 | | 0.23 | 0.77 | |
| 4/1/2000 | 0.69 | 0.31 | | 0.82 | 0.18 | |
| 5/1/2000 | 0.35 | 0.65 | | 0.50 | 0.50 | |
| 6/1/2000 | 0.73 | 0.27 | | 0.87 | 0.13 | |
| 7/1/2000 | 0.21 | 0.79 | | 0.36 | 0.64 | |
| 8/1/2000 | 0.05 | 0.95 | | 0.04 | 0.96 | |
| 9/1/2000 | 0.49 | 0.51 | | 0.65 | 0.35 | |
| 10/1/2000 | 0.55 | 0.45 | | 0.73 | 0.27 | |
| 11/1/2000 | 0.36 | 0.64 | | 0.59 | 0.41 | |
| 12/1/2000 | 0.29 | 0.71 | | 0.49 | 0.51 | |
| 1/1/2001 | 0.05 | 0.95 | | 0.06 | 0.94 | |
| 2/1/2001 | 0.39 | 0.61 | | 0.61 | 0.39 | |
| 3/1/2001 | 0.21 | 0.79 | | 0.38 | 0.62 | |
| 4/1/2001 | 0.43 | 0.57 | | 0.63 | 0.37 | |
| 5/1/2001 | 0.03 | 0.97 | | 0.09 | 0.91 | |
| 6/1/2001 | 0.59 | 0.41 | | 0.77 | 0.23 | |

FIG. 36D

| With Primary | | CRM Connectivity - fij | | | |
|---|---|---|---|---|---|
| 1 injector | | I1Z1-P2 | I1Z2-P2 | I1Z1-P3 | I1Z2-P3 |
| 2 producers | | 0.2 | 0.4 | 0.8 | 0.6 |
| 2 zones | | | | | |

| Producer P2 PLT actual measurment on Feb 2000 | | | Producer P3 PLT actual measurment on May 2000 | | |
|---|---|---|---|---|---|
| Production | P2-Z1 | P2-Z2 | Production | P3-Z1 | P3-Z2 |
| Measured PLT | 0.35 | 0.65 | Measured PLT | 0.5 | 0.5 |
| Primary + Secondary | 329 | 612 | Primary + Secondary | 926 | 926 |
| Primary | 231 | 372 | Primary | 90 | 323 |
| PLT Primary | 0.38 | 0.62 | PLT Primary | 0.22 | 0.78 |

FIG. 36E

| | | |
|---|---:|---:|
| Initial Production | 1000 | 800 |
| Decline | 0.3 | 0.2 |
| | | |
| | | |
| | | |
| | | |
| | | |
| | | |
| | | |
| | | |
| | P2 | P3 |
| | 1000 | 800 |
| | 740.8182 | 654.9846 |
| | 548.8116 | 536.256 |
| | 406.5697 | 439.0493 |
| | 301.1942 | 359.4632 |
| | 223.1302 | 294.3036 |
| | 165.2989 | 240.9554 |
| | 122.4564 | 197.2776 |
| | 90.71795 | 161.5172 |
| | 67.20551 | 132.2391 |
| | 49.78707 | 108.2682 |
| | 36.88317 | 88.64253 |
| | 27.32372 | 72.57436 |
| | 20.24191 | 59.41886 |
| | 14.99558 | 48.64805 |
| | 11.109 | 39.82965 |
| | 8.229747 | 32.60976 |
| | 6.096747 | 26.69862 |
| | 4.516581 | 21.85898 |

FIG. 36F

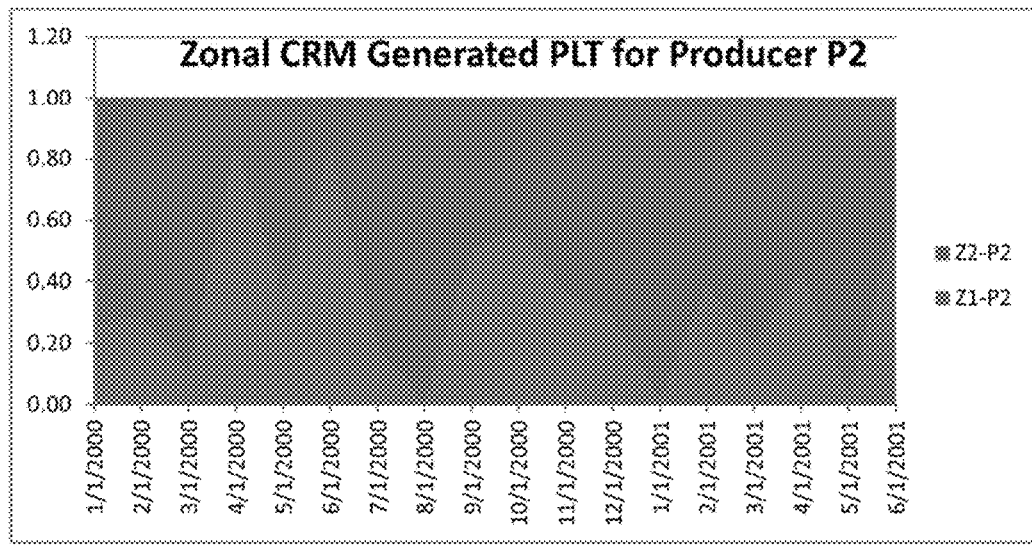
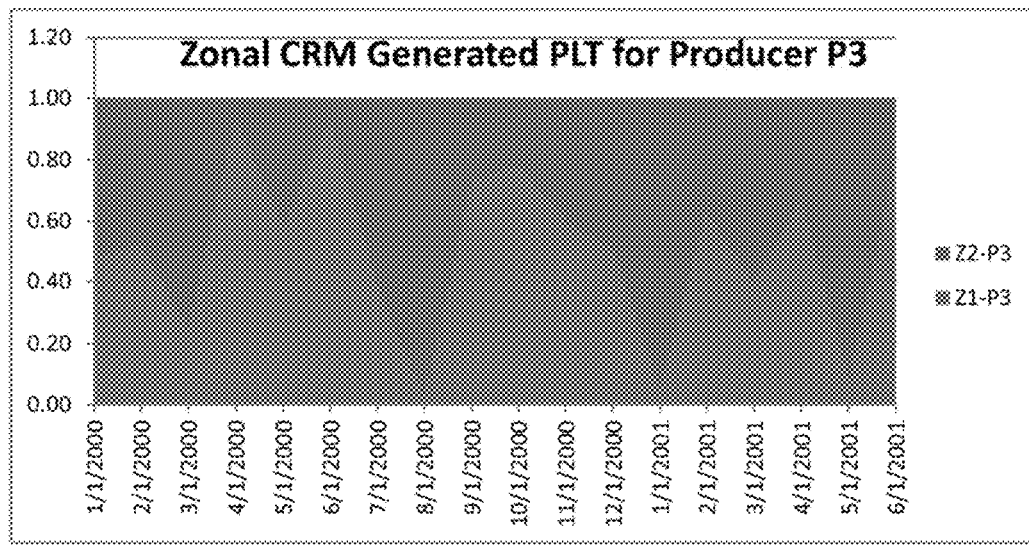
FIG. 36H

| Date | | Injection Rate I1 | Injection Rate I2 | Injection Profile | | | |
|---|---|---|---|---|---|---|---|
| | | | | ILT I1-Z1 | ILT I1-Z2 | ILT I2-Z1 | ILT I2-Z2 |
| 1 | 1/1/2000 | 4490 | 2840 | 41 | 59 | 51 | 49 |
| 2 | 2/1/2000 | 1090 | 2480 | 45 | 55 | 46 | 54 |
| 3 | 3/1/2000 | 2530 | 1770 | 20 | 80 | 95 | 5 |
| 4 | 4/1/2000 | 2950 | 3730 | 92 | 8 | 2 | 98 |
| 5 | 5/1/2000 | 2050 | 3470 | 51 | 49 | 38 | 62 |
| 6 | 6/1/2000 | 4040 | 3940 | 91 | 9 | 9 | 91 |
| 7 | 7/1/2000 | 3010 | 3930 | 32 | 68 | 53 | 47 |
| 8 | 8/1/2000 | 3640 | 2680 | 2 | 98 | 51 | 49 |
| 9 | 9/1/2000 | 2960 | 2040 | 67 | 33 | 5 | 95 |
| 10 | 10/1/2000 | 3230 | 4180 | 73 | 27 | 97 | 3 |
| 11 | 11/1/2000 | 4420 | 3810 | 53 | 47 | 55 | 45 |
| 12 | 12/1/2000 | 2290 | 4030 | 44 | 56 | 57 | 43 |
| 13 | 1/1/2001 | 4080 | 3750 | 4 | 96 | 79 | 21 |
| 14 | 2/1/2001 | 4880 | 2850 | 56 | 44 | 76 | 24 |
| 15 | 3/1/2001 | 2280 | 3080 | 33 | 67 | 4 | 96 |
| 16 | 4/1/2001 | 1980 | 2730 | 61 | 39 | 50 | 50 |
| 17 | 5/1/2001 | 4710 | 3300 | 6 | 94 | 69 | 31 |
| 18 | 6/1/2001 | 4530 | 2730 | 75 | 25 | 53 | 47 |

FIG. 37A

| Zonal Injection Rate | | Zonal Injection Rate | | Production Rate History | |
|---|---|---|---|---|---|
| Injection - I1Z1 | Injection - I1Z2 | Injection - I2Z1 | Injection - I2Z2 | Producer P2 | Producer P3 |
| 1841 | 2649 | 1448 | 1392 | 3994 | 2647 |
| 491 | 600 | 1141 | 1339 | 2568 | 2251 |
| 506 | 2024 | 1682 | 89 | 1910 | 1837 |
| 2714 | 236 | 75 | 3655 | 4615 | 2611 |
| 1046 | 1005 | 1319 | 2151 | 3380 | 2638 |
| 3676 | 364 | 355 | 3585 | 4736 | 2675 |
| 963 | 2047 | 2083 | 1847 | 3604 | 2971 |
| 73 | 3567 | 1367 | 1313 | 3255 | 2042 |
| 1983 | 977 | 102 | 1938 | 2822 | 1375 |
| 2358 | 872 | 4055 | 125 | 2211 | 3426 |
| 2343 | 2077 | 2096 | 1715 | 3679 | 2793 |
| 1008 | 1282 | 2297 | 1733 | 3162 | 2949 |
| 163 | 3917 | 2963 | 788 | 3295 | 2901 |
| 2733 | 2147 | 2166 | 684 | 2753 | 2191 |
| 752 | 1528 | 123 | 2957 | 3765 | 1912 |
| 1208 | 772 | 1365 | 1365 | 2332 | 1944 |
| 283 | 4427 | 2277 | 1023 | 3538 | 2461 |
| 3398 | 1133 | 1447 | 1283 | 2854 | 1948 |

FIG. 37B

CRM Connectivity - fij

| | I1Z1-P2 | I1Z2-P2 | I1Z1-P3 | I1Z2-P3 |
|---|---|---|---|---|
| Injector I1 | 0.2 | 0.4 | 0.8 | 0.6 |

| | I2Z1-P2 | I2Z2-P2 | I2Z1-P3 | I2Z2-P3 |
|---|---|---|---|---|
| Injector I2 | 0.3 | 1 | 0.7 | 0 |

FIG. 37C

| CRM Production Rate Estimates after history matching and obtaining connectivities at zonal level | | Secondary flux at zone level (qij = injection rate by zone multiplied by connectivity @ zone 1 and 2) | | | | CRM Estimates of Primary Production | |
|---|---|---|---|---|---|---|---|
| CRM P2 | CRM P3 | Z1-P2 | Z2-P2 | Z1-P3 | Z2-P3 | CRM P2 | CRM P3 |
| 4079 | 2686 | 802 | 2451 | 1158 | 834 | 826 | 694 |
| 2644 | 2432 | 440 | 1579 | 912 | 803 | 625 | 717 |
| 1975 | 1868 | 605 | 898 | 1345 | 53 | 472 | 470 |
| 4617 | 2758 | 565 | 3749 | 59 | 2193 | 303 | 506 |
| 3477 | 2753 | 604 | 2553 | 1054 | 1290 | 320 | 409 |
| 5112 | 2797 | 841 | 3730 | 283 | 2151 | 541 | 363 |
| 3911 | 3039 | 817 | 2665 | 1666 | 1108 | 429 | 265 |
| 3404 | 2061 | 424 | 2740 | 1093 | 787 | 240 | 181 |
| 2956 | 1432 | 427 | 2328 | 81 | 1162 | 201 | 189 |
| 2360 | 3622 | 1687 | 474 | 3243 | 75 | 199 | 304 |
| 3912 | 2988 | 1097 | 2545 | 1676 | 1028 | 270 | 284 |
| 3253 | 3040 | 890 | 2245 | 1837 | 1039 | 118 | 164 |
| 3458 | 3127 | 921 | 2354 | 2370 | 472 | 183 | 285 |
| 2777 | 2314 | 1196 | 1542 | 1732 | 410 | 39 | 172 |
| 3820 | 1922 | 187 | 3567 | 98 | 1774 | 66 | 50 |
| 2402 | 2115 | 651 | 1673 | 1092 | 819 | 78 | 204 |
| 3848 | 2612 | 739 | 2793 | 1821 | 613 | 316 | 178 |
| 2978 | 2066 | 1113 | 1736 | 1157 | 769 | 129 | 140 |

With Primary
2 injector
2 producers
2 zones

| Primary | | | | | Secondary recovery portion | | | | | |
|---|---|---|---|---|---|---|---|---|---|---|
| Zonal CRM Generated Continous PLT Estimates | | | | | Zonal CRM Generated Continous PLT Estimates | | | | | |
| Z1-P2 | Z2-P2 | Z1-P3 | Z2-P3 | | Z1-P2 | Z2-P2 | check = 1 | Z1-P3 | Z2-P3 | Check =1 |
| 642 | 184 | 547 | 147 | | 0.25 | 0.75 | 1.00 | 0.58 | 0.42 | 1.00 |
| 485 | 139 | 565 | 152 | | 0.22 | 0.78 | 1.00 | 0.53 | 0.47 | 1.00 |
| 367 | 105 | 370 | 99 | | 0.40 | 0.60 | 1.00 | 0.96 | 0.04 | 1.00 |
| 235 | 68 | 399 | 107 | | 0.13 | 0.87 | 1.00 | 0.03 | 0.97 | 1.00 |
| 248 | 71 | 323 | 87 | | 0.19 | 0.81 | 1.00 | 0.45 | 0.55 | 1.00 |
| 420 | 121 | 286 | 77 | | 0.18 | 0.82 | 1.00 | 0.12 | 0.88 | 1.00 |
| 333 | 96 | 209 | 56 | | 0.23 | 0.77 | 1.00 | 0.60 | 0.40 | 1.00 |
| 186 | 54 | 143 | 38 | | 0.13 | 0.87 | 1.00 | 0.58 | 0.42 | 1.00 |
| 156 | 45 | 149 | 40 | | 0.15 | 0.85 | 1.00 | 0.07 | 0.93 | 1.00 |
| 155 | 45 | 240 | 64 | | 0.78 | 0.22 | 1.00 | 0.98 | 0.02 | 1.00 |
| 210 | 60 | 224 | 60 | | 0.30 | 0.70 | 1.00 | 0.62 | 0.38 | 1.00 |
| 92 | 26 | 129 | 35 | | 0.28 | 0.72 | 1.00 | 0.64 | 0.36 | 1.00 |
| 142 | 41 | 225 | 60 | | 0.28 | 0.72 | 1.00 | 0.83 | 0.17 | 1.00 |
| 30 | 9 | 135 | 36 | | 0.44 | 0.56 | 1.00 | 0.81 | 0.19 | 1.00 |
| 51 | 15 | 39 | 11 | | 0.05 | 0.95 | 1.00 | 0.05 | 0.95 | 1.00 |
| 60 | 17 | 161 | 43 | | 0.28 | 0.72 | 1.00 | 0.57 | 0.43 | 1.00 |
| 245 | 70 | 140 | 38 | | 0.21 | 0.79 | 1.00 | 0.75 | 0.25 | 1.00 |
| 100 | 29 | 110 | 30 | | 0.39 | 0.61 | 1.00 | 0.60 | 0.40 | 1.00 |

FIG. 37D

Producer P2 PLT actual measurment on Feb 2000

| | Production P2-Z1 | P2-Z2 |
|---|---|---|
| Measured PLT | 0.35 | 0.65 |
| Primary + Secondary | 903 | 1677 |
| Priamry | 463 | 98 |
| PLT Primary | 0.82 | 0.18 |

Producer P3 PLT actual measurment on May 2000

| | Production P3-Z1 | P3-Z2 |
|---|---|---|
| Measured PLT | 0.5 | 0.5 |
| Primary + Secondary | 1346 | 1346 |
| Priamry | 292 | 56 |
| PLT Primary | 0.84 | 0.16 |

| Time | CRM PLT Estimates (Primary + Secondary) | | | | | |
|---|---|---|---|---|---|---|
| | Z1-P2 | Z2-P2 | check = 1 | Z1-P3 | Z2-P3 | Check =1 |
| 1/1/2000 | 0.37 | 0.63 | | 0.65 | 0.35 | |
| 2/1/2000 | 0.35 | 0.65 | | 0.61 | 0.39 | |
| 3/1/2000 | 0.51 | 0.49 | | 0.92 | 0.08 | |
| 4/1/2000 | 0.18 | 0.82 | | 0.14 | 0.86 | |
| 5/1/2000 | 0.25 | 0.75 | | 0.50 | 0.50 | |
| 6/1/2000 | 0.21 | 0.79 | | 0.18 | 0.82 | |
| 7/1/2000 | 0.26 | 0.74 | | 0.62 | 0.38 | |
| 8/1/2000 | 0.17 | 0.83 | | 0.62 | 0.38 | |
| 9/1/2000 | 0.20 | 0.80 | | 0.16 | 0.84 | |
| 10/1/2000 | 0.78 | 0.22 | | 0.96 | 0.04 | |
| 11/1/2000 | 0.31 | 0.69 | | 0.64 | 0.36 | |
| 12/1/2000 | 0.30 | 0.70 | | 0.65 | 0.35 | |
| 1/1/2001 | 0.33 | 0.67 | | 0.83 | 0.17 | |
| 2/1/2001 | 0.46 | 0.54 | | 0.81 | 0.19 | |
| 3/1/2001 | 0.11 | 0.89 | | 0.11 | 0.89 | |
| 4/1/2001 | 0.30 | 0.70 | | 0.59 | 0.41 | |
| 5/1/2001 | 0.25 | 0.75 | | 0.75 | 0.25 | |
| 6/1/2001 | 0.39 | 0.61 | | 0.62 | 0.38 | |

FIG. 37E

| | | |
|---|---:|---:|
| Initial Productio | 1000 | 800 |
| Decline | 0.3 | 0.2 |

| P2 | P3 |
|---:|---:|
| 1000 | 800 |
| 740.8182 | 654.9846 |
| 548.8116 | 536.256 |
| 406.5697 | 439.0493 |
| 301.1942 | 359.4632 |
| 223.1302 | 294.3036 |
| 165.2989 | 240.9554 |
| 122.4564 | 197.2776 |
| 90.71795 | 161.5172 |
| 67.20551 | 132.2391 |
| 49.78707 | 108.2682 |
| 36.88317 | 88.64253 |
| 27.32372 | 72.57436 |
| 20.24191 | 59.41886 |
| 14.99558 | 48.64805 |
| 11.109 | 39.82965 |
| 8.229747 | 32.60976 |
| 6.096747 | 26.69862 |
| 4.516581 | 21.85898 |

FIG. 37F

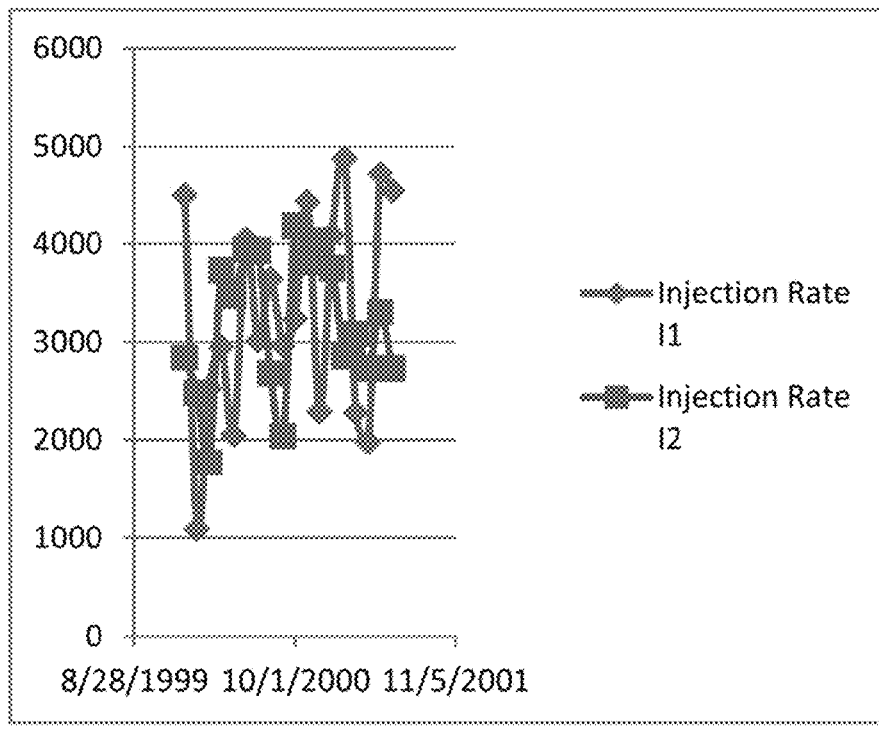
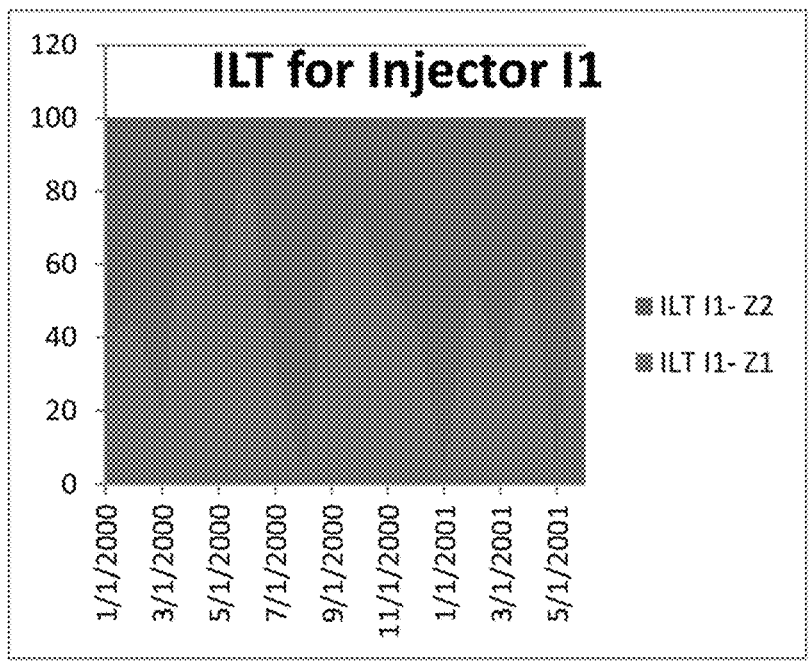
FIG. 37G

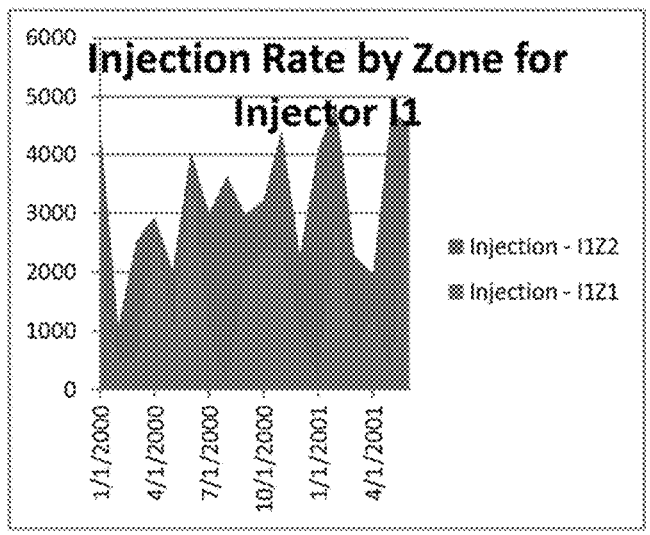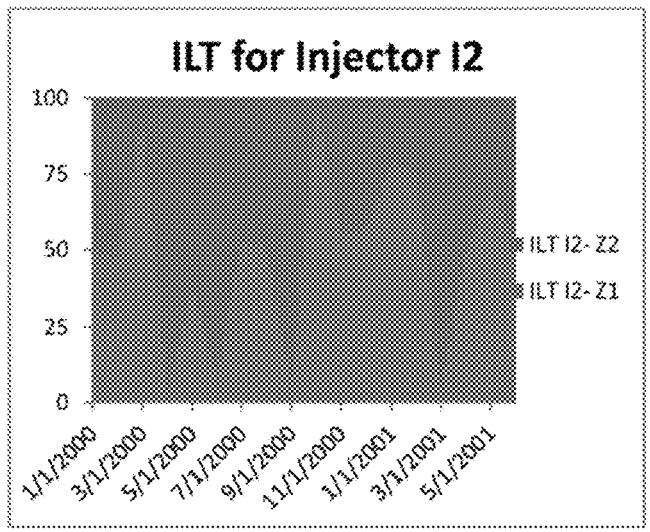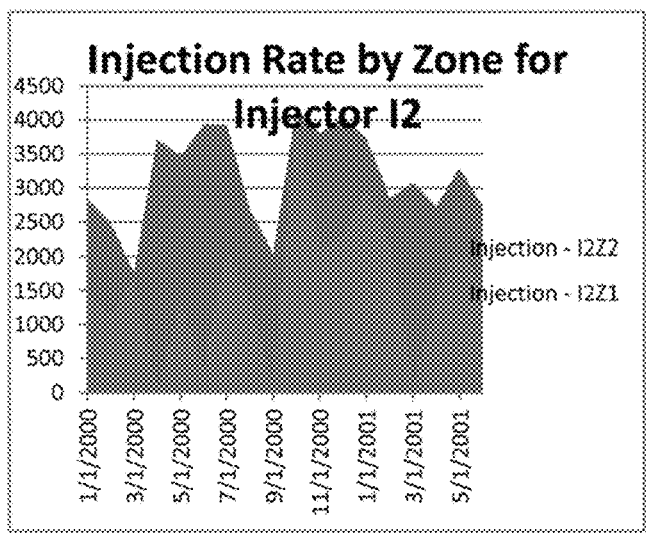
FIG. 37H

FLOODING ANALYSIS TOOL AND METHOD THEREOF

CROSS REFERENCE TO RELATED APPLICATIONS

This application claims benefit under 35 USC 119 of U.S. Provisional Patent Application No. 62/040,909 with a filing date of Aug. 22, 2014. This application also claims benefit under 35 USC 119 of U.S. Provisional Patent Application No. 62/135,016 with a filing date of Mar. 18, 2015. This application claims priority to and benefits from the foregoing, the disclosures of which are incorporated herein by reference.

This application is one of multiple non-provisional patent applications filed on Aug. 21, 2015 with the title of FLOODING ANALYSIS TOOL AND METHOD THEREOF. Ser. Nos. 14/832,637, 14/832,630, 14/832,792, 14/832,799, 14/832,805, 14/832,826, 14/832,841. All of these non-provisional patent applications are related, and all of their disclosures are incorporated herein by reference.

TECHNICAL FIELD

The present disclosure relates generally to producing hydrocarbons from a subterranean reservoir using a flood operation, and more specifically, this disclosure relates to analyzing the flood operation.

BACKGROUND

Different mechanisms are typically utilized to produce hydrocarbons, such as oil and gas, from a subterranean reservoir. Initially, hydrocarbons are driven from the reservoir to the surface by the natural differential pressure between the reservoir and the bottomhole pressure within a wellbore. After the pressure stage, an artificial lift system such as a sucker rod pump and an electrical submersible pump can be utilized to drive hydrocarbons to the surface. After the artificial lift stage, a flood operation can be utilized to drive hydrocarbons to the surface. In a flooding or flood operation, displacing fluid such as water, gas, surfactants, polymers, etc. is injected into the reservoir via one or more injection wells, and the displacing fluid displaces or physically sweeps the hydrocarbons towards one or more producing wells to the surface.

Analysis of a flood operation is oftentimes a difficult task. For example, the subterranean reservoir can include various geological features such as faults, naturally occurring fractures, different rock types, etc., and these geological features affect how the injection wells and the production wells are linked in the subterranean reservoir. Indeed, a typical field can have hundreds of wells, and the wells can be linked in all sorts of ways, further complicating analysis of the flood operation. Therefore, the industry is always searching for improvements in analyzing a flood operation.

SUMMARY

Described herein are various embodiments of computer-implemented methods, computing systems, and program products for analyzing a flood operation on a hydrocarbon reservoir.

In one aspect, a computer implemented method of determining a value of injected fluid for a flood operation on a hydrocarbon reservoir is provided. The method includes, for a first injection well of the hydrocarbon reservoir: receiving injection rate data for the first injection well and production rate data for at least one production well communicating with the injection well, running capacitance resistance modeling using the received data to generate an interwell connectivity for each injection well and production well pair, determining a value of injected fluid for each injection well and production well pair using the generated interwell connectivity for the well pair and an oil-cut value for the production well of the pair, and aggregating the generated values of injected fluid per pair to determine a value of injected fluid for the first injection well.

In yet another aspect, a computing system for determining a value of injected fluid for a flood operation on a hydrocarbon reservoir is provided. The system includes at least one processor and at least one memory containing computer executable instructions, that when executed by the at least one processor, cause the computing system to perform a method. The method includes, for a first injection well of the hydrocarbon reservoir: receiving injection rate data for the first injection well and production rate data for at least one production well communicating with the injection well, running capacitance resistance modeling using the received data to generate an interwell connectivity for each injection well and production well pair, determining a value of injected fluid for each injection well and production well pair using the generated interwell connectivity for the well pair and an oil-cut value for the production well of the pair, and aggregating the generated values of injected fluid per pair to determine a value of injected fluid for the first injection well.

In yet another aspect, a computer-readable storage medium includes computer-executable instructions which, when executed by a computing system, cause the computing system to perform a method of determining a value of injected fluid for a flood operation on a hydrocarbon reservoir. The method includes, for a first injection well of the hydrocarbon reservoir: receiving injection rate data for the first injection well and production rate data for at least one production well communicating with the injection well, running capacitance resistance modeling using the received data to generate an interwell connectivity for each injection well and production well pair, determining a value of injected fluid for each injection well and production well pair using the generated interwell connectivity for the well pair and an oil-cut value for the production well of the pair, and aggregating the generated values of injected fluid per pair to determine a value of injected fluid for the first injection well.

The above summary section is provided to introduce a selection of concepts in a simplified form that are further described below in the detailed description section. The summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

These and other features of the present disclosure will become better understood with regard to the following description, claims and accompanying drawings where:

FIG. 18 illustrates one embodiment of a computer implemented method of identifying at least one conformance candidate.

FIGS. 21A-21C, 22A-22B, 23A-23G, 24A-24F illustrate examples consistent with the embodiment of FIG. 20.

FIG. 27 illustrates one embodiment of a computer implemented method of analyzing a polymer flood operation on a hydrocarbon reservoir having at least one injection well and at least one production well

FIGS. 29A, 29B, 29C illustrate one embodiment of a computer implemented method for using polygons to choose between two infill candidates in two different reservoirs and examples thereof.

FIGS. 30A, 30B, 30C illustrate one embodiment of a computer implemented method for using polygons (e.g., streamgrids) for pattern realignment and examples thereof.

FIGS. 31A, 31B, 31C illustrate one embodiment of a computer implemented method for using polygons (e.g., streamgrid) allocation factors to initiate CRM interwell connectivity and examples thereof.

FIG. 32A, 32B, 32C illustrate one embodiment of a computer implemented method for estimating maximal areal sweep by zone and by reservoir with the populated polygons (e.g., streamgrids) and examples thereof.

FIG. 33 illustrates one embodiment of a computer implemented method of determining a value of injected fluid for a flood operation on a hydrocarbon reservoir having at least one injection well and at least one production well.

FIGS. 34, 35A-35E, 36A-36H, 37A-37I illustrate one embodiment of a method for analyzing a flood operation for a hydrocarbon reservoir having a plurality of zones and examples thereof.

DETAILED DESCRIPTION

The various embodiments of computer implemented methods described herein may be used to analyze a flood operation on a subterranean reservoir. Furthermore, the various methods described herein may be used in combination or individually. For example, the methods involving determining allowed well connections may be used in conjunction with determining the value of injected fluid (VOIF). As another example, the methods involving determining allowed well connections may be used in conjunction with CRM zonal. As another example, the methods involving determining allowed well connections may be used in conjunction with analyzing a first flood operation and a second flood operation.

Furthermore, there may be a corresponding apparatus (e.g., computing systems) and/or program product for each computer implemented method. Indeed, those of ordinary skill in the art will understand that the invention is not limited to the disclosed embodiments, and for example, computer implemented methods, apparatuses, and/or program products, as well as claim language for the same, are in the scope of this disclosure.

For ease of understanding, various running examples will be utilized throughout this disclosure. Also, for ease of understanding, terminology such as A, B, C, or any combination thereof may include (i) A only. The terminology A, B, C, or any combination thereof may include (ii) B only. The terminology A, B, C, or any combination thereof may include (iii) C only. The terminology A, B, C, or any combination thereof may include (iv) A and B. The terminology A, B, C, or any combination thereof may include (v) A and C. The terminology A, B, C, or any combination thereof may include (vi) B and C. The terminology A, B, C, or any combination thereof may include (vii) A, B, and C.

Furthermore, some terms are used interchangeably herein, such as producer and production well, injector and injection well, zone level and zonal level, etc.

Flood Operation

Figure 1:
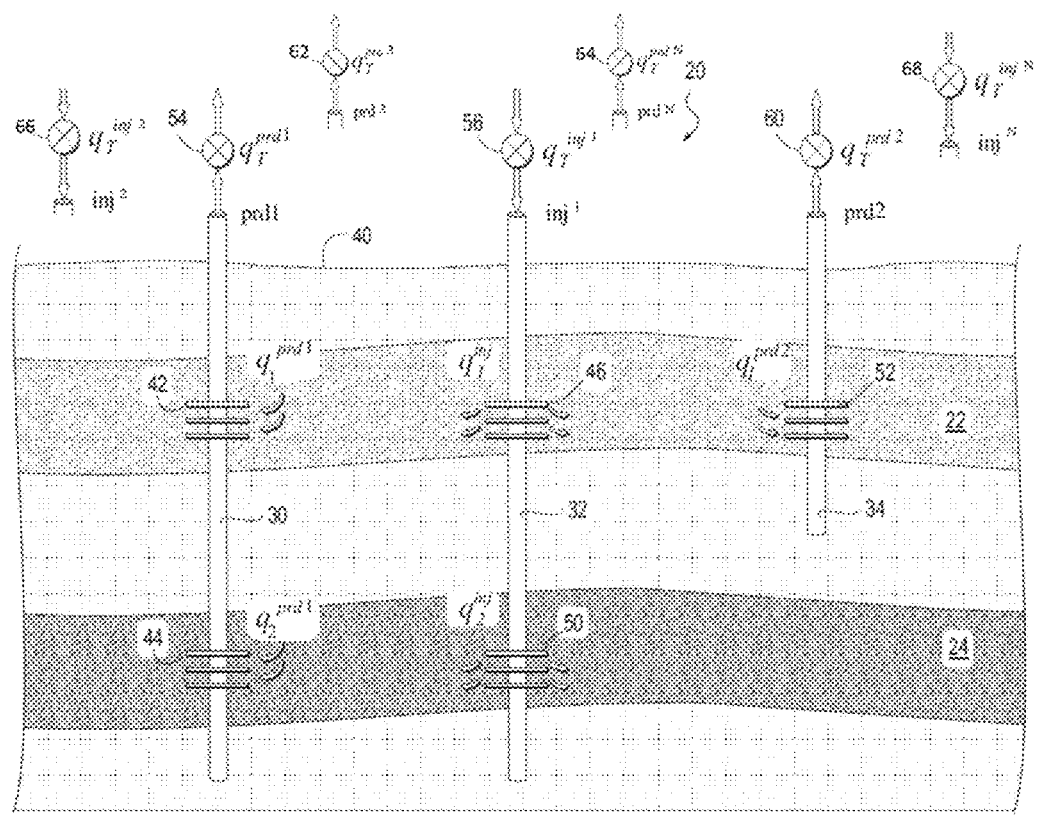
FIG. 1 illustrates an embodiment of a hydrocarbon reservoir with a plurality of injection wells and a plurality of production wells for a flood operation.

FIG. 1 schematically illustrates an embodiment of a hydrocarbon reservoir 20 with a plurality of injection wells (or injectors) and a plurality of production wells (or producers) for a flood operation. The reservoir 20 can be practically any type of subterranean or subsurface formation in which hydrocarbons are stored, such as limestone, dolomite, oil shale, sandstone, any combination thereof, or other subsurface formation. The reservoir 20 can be located onshore, offshore, deepwater, or at another location.

The flood operation can inject practically any displacing fluid such as water, brine or salt water, water alternating gas referred to as WAG, gas (e.g., carbon dioxide), steam, surfactant, polymer, any combination thereof (e.g., combination of polymer and surfactant), or other material. The flood operation may be performed on the reservoir 20 over a few years or decades. More than one flood operation may also be performed on the reservoir 20. For example, a first flood operation during a first time period may inject water into the reservoir 20 and a subsequent second flood operation during a second time period may inject polymer (or combination of polymer and surfactant) in the reservoir 20, as described further herein.

The injection wells and the production wells may be placed at practically any location that may facilitate hydrocarbon production from the reservoir 20. For example, some of the wells may be placed in locations that form a pattern. The pattern may be practically any pattern that can be used in a flood operation, such as a two spot pattern, a three spot pattern, a four spot pattern, a skewed four spot pattern, a five spot pattern, a seven spot pattern, an inverted seven spot pattern, a nine spot pattern, an inverted nine spot pattern, a direct line drive pattern, a staggered line drive pattern, a peripheral flood pattern, an irregular pattern (e.g., an irregular five spot pattern), any combination thereof, etc. The reservoir 20 may also include different patterns and no-pattern well configurations.

At the well level, the production wells 30, 34 and the injection well 32 are drilled and completed in the reservoir 20. The production wells or injection wells can be completed in any manner (e.g., an openhole completion, a cemented casing and/or liner completion, a gravel-packed completion, etc.) As illustrated in FIG. 1, completions 42, 44, 46, 50, 52 provide fluid communication (e.g., via perforations) between the injection well 32, the reservoir 20, and the production wells 30, 34. The production wells 30, 34 and the injection well 32 fluidly connect the reservoir 20 to surface 40 of the subterranean reservoir 20. The surface 40 can be a ground surface as depicted in FIG. 1, a platform surface in an offshore environment, etc.

Chokes or well control devices 54, 56, 60 are used to control the flow of fluid into and out of respective production wells 30, 34 and injection well 32. The well control devices 54, 56, 60 also control the pressure profiles in the production wells 30, 34 and the injection well 32. Although not shown, the production wells 30, 34 and the injection well 32 can fluidly connect with surface facilities (e.g., separators such as oil/gas/water separators, gas compressors, storage tanks, pumps, gauges, pipelines, etc.) at the surface 40. The rate of flow of fluids through the production wells 30, 34 and the injection well 32 can depend on the fluid handling capacities of the surface facilities at the surface 40. The control devices 54, 56, 60 can be above surface and/or positioned downhole.

During the flood operation, the displacing fluid injected by the injection well 32 can drive the hydrocarbons of the reservoir 20 to the production well 30, the production well 34, or both depending on how the wells 30, 32, 34 are linked in the reservoir 20. The displacing fluid injected by the injection well 32 can additionally drive the hydrocarbons of the reservoir 20 to a production well 62, a production well 64, or both depending on how the wells 30, 32, 34, 62, 64 are linked in the reservoir 20 and the completions. Similarly, the fluid injected by an injection well 66 can drive the hydrocarbons of the reservoir 20 to one or more of the production wells 30, 34, 62, 64 depending on how the wells are linked in the reservoir 20, and so on for an injection well 68. At the zone or zonal level, the reservoir 20 can include a plurality of rock layers including hydrocarbon bearing stratas or zones 22, 24. This zonal level discussion will focus on wells 30, 32, 34, but the discussion equally applies to wells 62, 64, 66, 68. Also, the reservoir 20 can include more zones than those illustrated in FIG. 1.

The production wells 30, 34 and the injection well 32 extend into one or more of the hydrocarbon bearing zones 22, 24 of the reservoir 20 such that the production wells 30, 34 and injection well 32 are in fluid communication with the hydrocarbon bearing zones 22, 24. The completions 42, 44, 46, 50, 52 provide fluid communication (e.g., via perforations) between the injection well 32, the hydrocarbon bearing zones 22, 24, and the production wells 30, 34. The production wells 30, 34 can receive displacing fluids (e.g., gas, oil, water, etc.) from the hydrocarbon bearing zones 22, 24 and the injection well 32 can inject fluid into the hydrocarbon bearing zones 22, 24. Also, the displacing fluid injected into one zone may flow into one or more different zones referred to as crossflow. The production wells 30, 34 and the injection well 32 fluidly connect hydrocarbon bearing zones 22, 24 to the surface 40 of the subterranean reservoir 20.

During the flood operation, the fluid injected by the injection well 32 at the zone 22 can drive the hydrocarbons of the zone 22 of the reservoir 20 to the production well 30 at zone 22, the production well 34 at zone 22, or both depending on how the wells 30, 32, 34 are linked in the reservoir 20 at the zonal level. The fluid injected by the injection well 32 at the zone 22 can additionally drive the hydrocarbons of the zone 22 of the reservoir 20 to the production well 62 at zone 22 (not shown), production well 64 at zone 22 (not shown), or both depending on how the wells 30, 32, 34, 62, 64 are linked in the reservoir 20 at the zonal level and the completions at the zonal level. Similarly, the fluid injected by the injection well 32 at zone 24 can drive the hydrocarbons of the reservoir 20 to one or more of the production wells 30, 34, 62, 64 depending on how the wells are linked in the reservoir 20 at the zonal level and the completions at the zonal level. For example, the production well 34 is not completed at zone 24 and therefore hydrocarbons that flow along zone 24 towards the production well 34 may not be able to enter the production well 34 at zone 24. Similarly, the fluid injected by the injection well 66 at zone 24 (not shown) can drive the hydrocarbons of the reservoir 20 to one or more of the production wells 30, 34, 62, 64 depending on how the wells are linked in the reservoir 20 at the zonal level and the completions at the zonal level, and so on for the injection well 68.

Those of ordinary skill in the art will appreciate that FIG. 1 is provided for context and various modifications are possible. For example, some embodiments can have fewer or more than the quantity of wells illustrated in FIG. 1, as well as different patterns or well locations. The production wells or the injection wells can also deviate from the illustrated vertical position such that in some embodiments, one or more wells can be a directional well, a horizontal well, or a multilateral well.

Hardware and Software

Figure 2A:
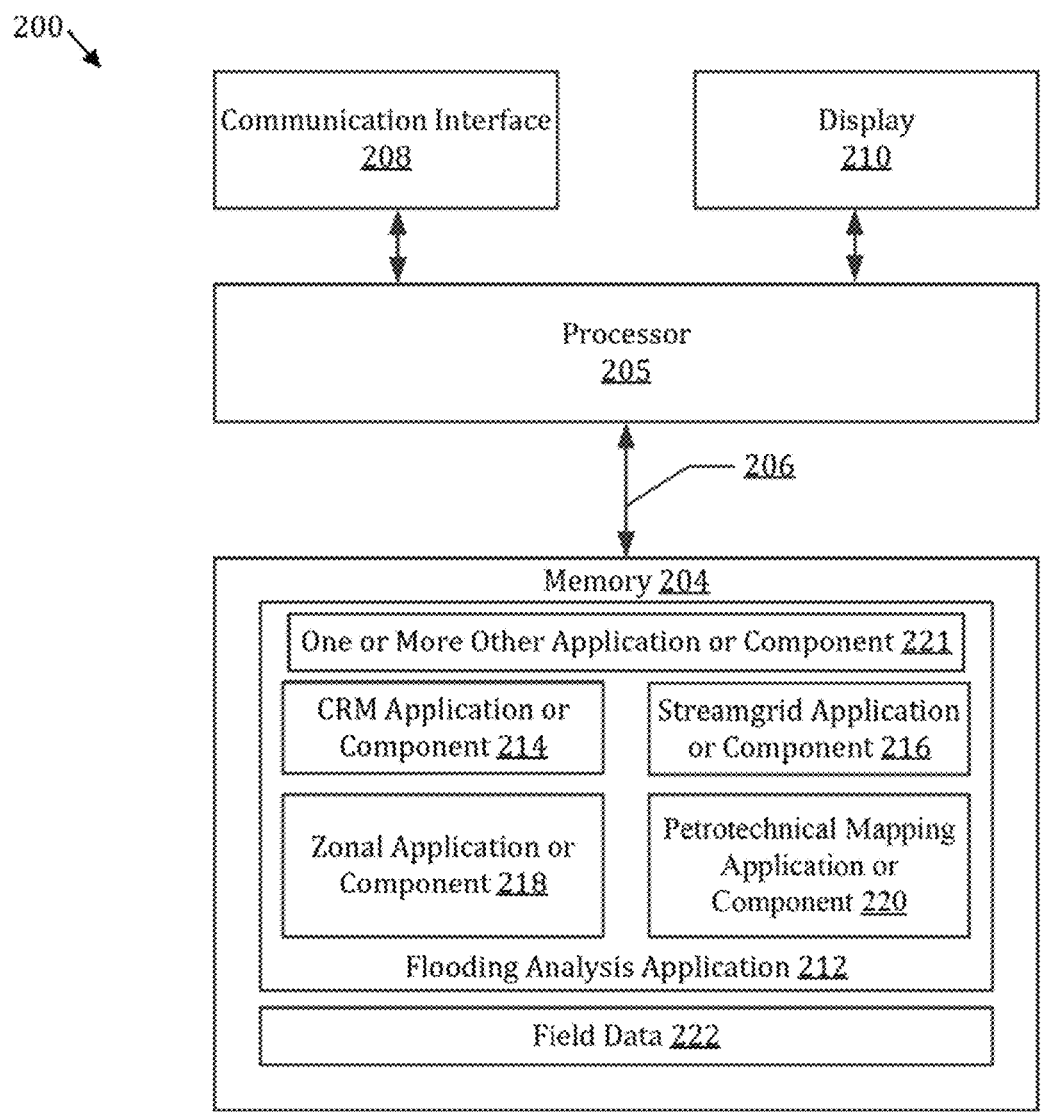
FIG. 2A illustrates a computing system useable to analyze a flood operation on a hydrocarbon reservoir.

FIG. 2A illustrates a computing system 200 useable to analyze a flood operation on a subterranean reservoir. The computing system 200 can, in example embodiments, be communicatively connected to systems providing data such as field data 222 and/or systems for further processing or interpreting the field data 222 as described herein. The field data 222 can include practically any data related to a field or components thereof. Examples of the field data 222 are discussed in connection with FIGS. 4-5. In some embodiments, the field data 222 can include non-field data, such as manufacturer data about a displacing fluid or material thereof (e.g., manufacturer data about a polymer), manufacturer data about a conformance agent, manufacturer data on equipment tolerances, etc. In general, the computing system 200 includes at least one processor 205 communicatively connected to at least one memory 204 via at least one data bus 206. The processor 205 can be any of a variety of types of programmable circuits capable of executing computer-readable instructions to perform various tasks, such as mathematical and communication tasks.

The memory 204 can include any of a variety of memory devices, such as using various types of computer-readable or computer storage media. A computer storage medium or computer-readable medium may be any medium that can contain or store the program for use by or in connection with the instruction execution system, apparatus, or device. By way of example, computer storage media may include dynamic random access memory (DRAM) or variants thereof, solid state memory, read-only memory (ROM), electrically-erasable programmable ROM, optical discs (e.g., CD-ROMs, DVDs, etc.), magnetic disks (e.g., hard disks, floppy disks, etc.), magnetic tapes, and other types of devices and/or articles of manufacture that store data. Computer storage media generally includes at least one or more tangible media or devices. Computer storage media can, in some embodiments, include embodiments including entirely non-transitory components. In the embodiment shown, the memory 204 may store a flooding analysis application 212, discussed in further detail below. The computing system 200 can also include a communication interface 208 configured to receive and transmit data, for example, the field data 222. Additionally, a display 210 can be used for presenting a graphical display of the flooding analysis application 212 or applications or components thereof, for displaying maps (e.g., saturation and pressure maps such as from a petrotechnical mapping application or component 220), for displaying user interfaces, for displaying curves, for displaying graphs, for displaying plots, for displaying tables, etc.

In various embodiments, the flooding analysis application 212 includes a capacitance resistance modeling or CRM application or component 214, a polygon application or component 216, a zonal application or component 218, the petrotechnical mapping application or component 220. The polygon application 216 may be a streamgrid application or component 216. CRM will be discussed further in the context of FIG. 3. In some embodiments, for example, the flooding analysis application 212 (or applications or components 214, 216, 218, 220 thereof) can include one or more other application or component 221 and/or receive data from the one or more other application or component 221. The one or more other application or component 221 can be a vendor product, a petrotechnical application such as a petrotechnical 4D seismic processing application or component, etc. In some embodiments, the CRM application 214, the polygon application 216, the zonal application 218, the petrotechnical mapping application 220, and/or the one or more other application 221 can be standalone and separate from the flooding analysis application 212.

Figure 2B:
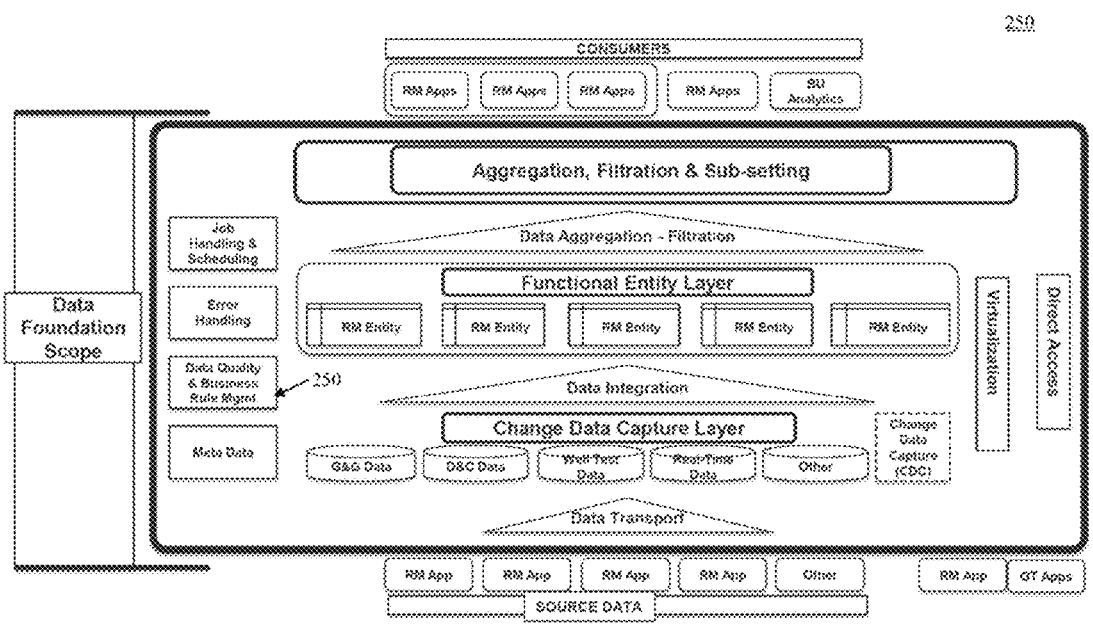
FIG. 2B illustrates an embodiment of a data management system.
Figure 2C:
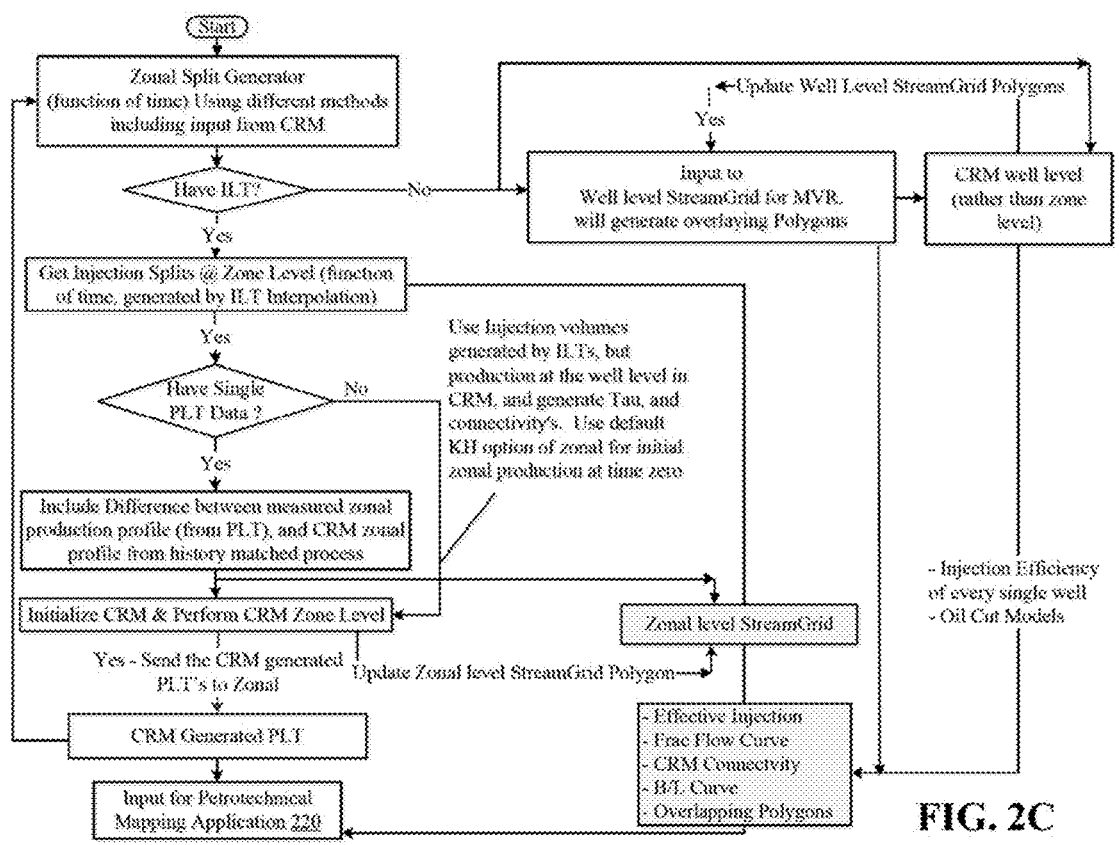
FIG. 2C illustrates an embodiment of an interactivity workflow that may be executed by the computing system of FIG. 2A.

Moreover, some or all the applications 214, 216, 218, 220, 221 can interact with each other (e.g., as illustrated in FIGS. 2A, 2C). For example, some or all of the applications 214, 216, 218, 220, 221 can interact by sharing data directly or providing data to a repository (e.g., operational data store (ODS)) that is accessible to the other applications.

In one embodiment, the flooding analysis application 212 may be associated with a solution, such as a flood or waterflood surveillance, analysis, & optimization solution. The flood surveillance, analysis, & optimization solution may be one of many solutions I-Field® program solutions, such as (i) a real time reservoir management solution, (ii) a well reliability & optimization decision support center solution, (iii) an integrated operations center solution, (iv) a drilling & completions decision support center solution, (v) a logistics decision support solution, (vi) a machinery & power support center solution, and (vii) a real time facilities optimization solution. An Upstream Workflow Transformation (UWT) effort or other effort can be utilized to accelerate the adoption and deployment of the solutions globally. Each of the solutions may interact with each other. Each of these solutions may be associated with at least one application (e.g., the other application 221) just like the flood surveillance, analysis, & optimization solution is associated with the flooding analysis application 212.

Each of these solutions may receive data from and/or send data to a data management system referred to as data foundation or UWT data foundation. For example, the data management system may provide at least some of the field data 222 for the flooding analysis application 212. Thus, in some embodiments, the field data 222 may represent the data management system. The data management system may be centralized, and business units have access to all data for all business units or limited access to the data based on permission. Alternatively, each business unit may have its own local data management system with data that is of interest to that business unit.

The data management system may help business units to source data for quicker, more efficient deployment of the solutions of interest. For example, some of the solutions may depend on a complex set of data from disparate IT systems across the business units, often with histories spanning decades. Many business units may also have existing legacy technology standards and IT systems in place with existing dependencies on service providers or vendors to support and maintain. Furthermore, some of the solutions may depend on an abundance of homeless data that may need to be collected, reviewed, and organized, and much of this data is decentralized across assets. Some of the solutions may also depend on unstructured data residing in non-traditional IT systems. The business units may differ widely in geographical locations, asset classes, business models, regulatory requirements, partnerships, and legal agreements that impact the ability to deploy solutions, especially where dependencies on complex data types exist.

The data management system provides a standardized architecture to improve efficiency in deployments of the solutions. For example, the data management system provides a standardized architecture (e.g., based on UWT target architecture and upstream data objectives), implements consistent data standards, implements data models based on internal and industry standards, manages all forms of data, provides mature data governance, provides data accountability, and implements managed integration to reuse data and enables business workflows. The target architecture describes the preferred model for sourcing data from business unit system of records, performing transformations to the data to support workflows, and moving this data into a format suitable for access by the appropriate solution. The data management system also increases organizational capability to improve data quality for better decision making and decreased risk, for example, improving the quality of the high value data in daily operations and making available high quality data to support growth rates in functions and business units. The data management system may also improve the ability to actively monitor every barrel from business unit assets and may increase the ability to proliferate business unit led innovations across other business units.

FIG. 2B illustrates an embodiment of a data management system 250. In FIG. 2B, "RM" stands for reservoir management, "D&C" stands for drilling and completions, "BU" stands for business unit, and "G&G" stands for geology and geophysics. Of note, the data management system 250 includes a box 252 for data quality and business rule management, which may represent business rules to improve data quality. For example, the business rules can be applied to ensure certain data is not zero, certain data is numeric, certain data is text, certain data is alphanumeric, certain data is within a particular range, certain data is in the correct location, certain data is in the correct unit of measurement, certain data is transformed, etc. The business rules can also be based on correlations within data, such as existence of one rule dependent on existence of other data or range of other data. Also, business rules can search for heuristic trends within the data or boundary conditions such as date intervals between well tests. As another example, the business rules may ensure that wells are tested based on predetermined assumptions or may apply practically any logic test The result of a business rule can be a monitoring condition or an action applied programmatically. For example, the result of a business rule may be a report or alert of failures, transposition of data based on logical conditions, etc. The business rules may be generated based on feedback from business units, based on requirements of the computing system or applications, any combination thereof, etc.

To create the data management system 250, existing business unit local data foundation designs can be leveraged. Alternatively, existing business local data foundation designs (e.g., functionally, technically, or by adding assets) can be extended. Alternatively, the system can be built by partnering with an interested business unit when there is no existing local data foundation capability to leverage prior designs.

The embodiment illustrated in FIG. 2C can be executed by the computing system 200 of FIG. 2A. FIG. 2C is discussed further in U.S. Provisional Patent Application No. 62/040,909, filed Aug. 22, 2014, title FLOODING ANALYSIS TOOL AND METHOD THEREOF, which is incorporated by reference in its entirety.

Those of ordinary skill in the art will appreciate that although certain terminology is used herein, such as the terms solution, application, component, etc., the invention is not limited to the exact embodiments disclosed herein. For example, embodiments consistent with this disclosure can be performed using computer executable instructions, computer executable code, modules, data structures, graphs, plots, maps, etc., and the embodiments are not limited to any specific arrangement in this disclosure.

Referring generally to the systems and methods herein, and referring to in particular computing systems embodying the methods and systems of the present disclosure, it is noted that various computing systems can be used to perform the processes disclosed herein. For example, embodiments of the disclosure may be practiced in various types of electrical circuits comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, aspects of the methods described herein can be practiced within a general purpose computer or in any other circuits or systems.

Embodiments of the present disclosure can be implemented as a computer process (method), a computing system, or as an article of manufacture, such as a computer program product or computer readable media. The term computer readable media as used herein may include computer storage media. Computer storage media may include volatile and nonvolatile, removable and non-removable media implemented in any method or technology for storage of information, such as computer readable instructions, data structures, routines, code, applications, programs, or program modules. Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing system 200, above. Computer storage media does not include a carrier wave or other propagated or modulated data signal. In some embodiments, the computer storage media includes at least some tangible features; in many embodiments, the computer storage media includes entirely non-transitory components.

Embodiments of the present disclosure can be implemented in hardware only, software only, or a combination of hardware and software. Furthermore, embodiments of the present disclosure can include at least one server, at least on client device, a workstation, a distributed setup, a mobile device, etc. depending on the implementation.

Embodiments of the present disclosure, for example, are described herein with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved. Embodiments may include fewer than or more than the functionality/acts provided herein.

Capacitance Resistance Modeling (CRM)

Typically, CRM is run using only historical injection rates and production rates. CRM is built based on material balance and rooted in signal processing for nonlinear multivariate regression. With a rate variation in an injector, CRM can capture interactions among production wells and injection wells by matching the response in the production rates. Typically, running CRM results in two sets of parameters, namely, interwell connectivity ($F_{ij}$) and response time (Tau or $\tau$) per injection well and production well pair. The interwell connectivity quantifies the support from one injection well to one production well, and the response time estimates the time a production well takes to response to a variation in the injection rate. Those parameters can be determined via history matching the production rates of all production wells. CRM can have three forms: CRMT to represent the drainage volume of the entire field, CRMP to represent the drainage volume of each production well, and CRMIP to represent the drainage volume of each production well and injection well pair.

Injection rates and production rates are typically used as input to CRM, as discussed in Weber, et al. "Improvements in Capacitance-Resistive Modeling and Optimization of Large Scale Reservoirs," SPE 121299, 2009 SPE Western Regional Meeting held in San Jose, Calif., USA, 24-26 Mar. 2009, which is incorporated by reference in its entirety. The following documents also discuss CRM, and each of these documents is incorporated by reference in its entirety: (i) Sayarpour, et al. "The Use of Capacitance-Resistive Models for Rapid Estimation of Waterflood Performance and Optimization", SPE 110081, 2007 SPE Annual Technical Conference and Exhibition held in Anaheim, Calif., USA, 11-14 Nov. 2007, (ii) Sayarpour, et al., "Field Applications of Capacitance Resistive Models in Waterfloods", SPE 114983-MS, 2008 SPE Annual Technical Conference and Exhibition held in Denver, Colo., USA, 21-24 Sep. 2008, (iii) Sayarpour, et al., "Field Applications of Capacitance Resistive Models in Waterfloods", SPE 114983-PA, December 2009 SPE Reservoir Evaluation & Engineering, (iv) Sayarpour, et al., "Probabilistic History Matching With the Capacitance-Resistance Model in Waterfloods: A Precursor to Numerical Modeling", SPE 129604, 2010 SPE Improved Oil Recovery Symposium held in Tulsa, Okla., USA, 24-28 Apr. 2010, and (v) Sayarpour, M., "Development and Application of Capacitance-Resistive Models to Water/$CO_2$ Floods", pages 1-236, available at http://repositories.lib.utexas.edu/handle/2152/15357?show=full, which are all incorporated by reference in their entireties.

Allowed Well Connections

FIGS. 3-12 illustrate embodiments of computer implemented methods of analyzing a flood operation on a hydrocarbon reservoir having at least one production well and at least one injection well, and more particularly, embodiments that include determining allowed connections that may be used as input to CRM. The embodiments illustrated in FIGS. 3-12 can be executed by a computing system, such as the computing system 200 of FIG. 2A or the CRM application 214 thereof. The allowed well connections may affect history matching and generation of the interwell connectivities when CRM is run, which may lead to more accurate output from CRM, such as more accurate response times and interwell connectivities. The output from CRM and/or other data available after executing the embodiments may be used as input to update or integrate with the polygon application 216, the zonal application 218, the petrotechnical mapping application 220, the one or more other application 221, the flooding analysis application 212, and/or other item (e.g., as illustrated in FIGS. 2A, 2C).

Referring to FIGS. 1-13, FIG. 3 illustrates one embodiment of a method 300 that can be executed by a computing system, such as the computing system 200, to analyze a flood operation on the reservoir 20 or the like. For simplicity, the discussion will first focus on the well level, and then turn to the zonal level.

At 302, field data is received. Receiving field data can include acquiring, capturing, obtaining, requesting, providing, etc. For example, the field data 222 can be received from the wells 30, 32, 34, 62, 64, 66, 68 of the reservoir 20, the well control devices 54, 56, 60, sensors, meters, transmitters, and other equipment (e.g., hydrophones, gauges, etc.), databases, ODS, the data management system 250 of FIG. 2B, analysis at the surface 40 (e.g., laboratory analysis), data streams, users, any combination thereof, etc. The field data 222 can be received in a raw state or in a non-raw state (e.g., errors are removed from the raw data). The field data 222 may include text, values, measurements, signals, etc. The field data 222 can be static or dynamic. The field data 222 can be real-time data, but does not have to be real-time data. The field data 222 can be numeric, text, alphanumeric, etc. The field data 222 can be actual data from actual hydrocarbon production, or in some embodiments, the field data 222 can include simulation data, synthetic data, estimates, forecasts, predictions, etc. The field data 222 may be streaming or non-streaming.

Figure 4:
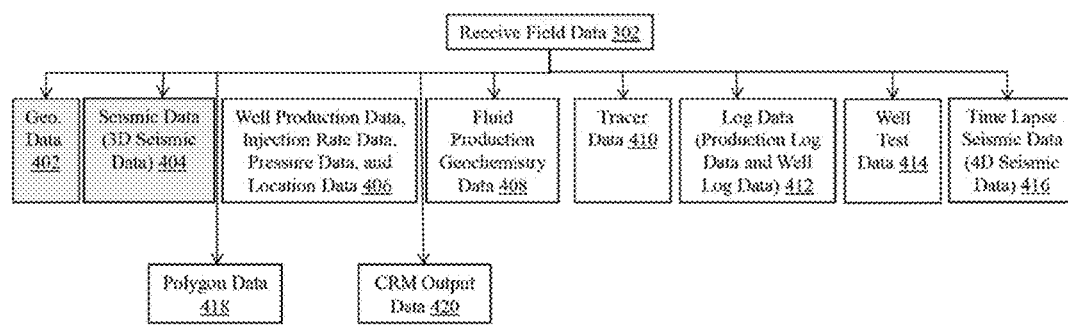
Figure 5:
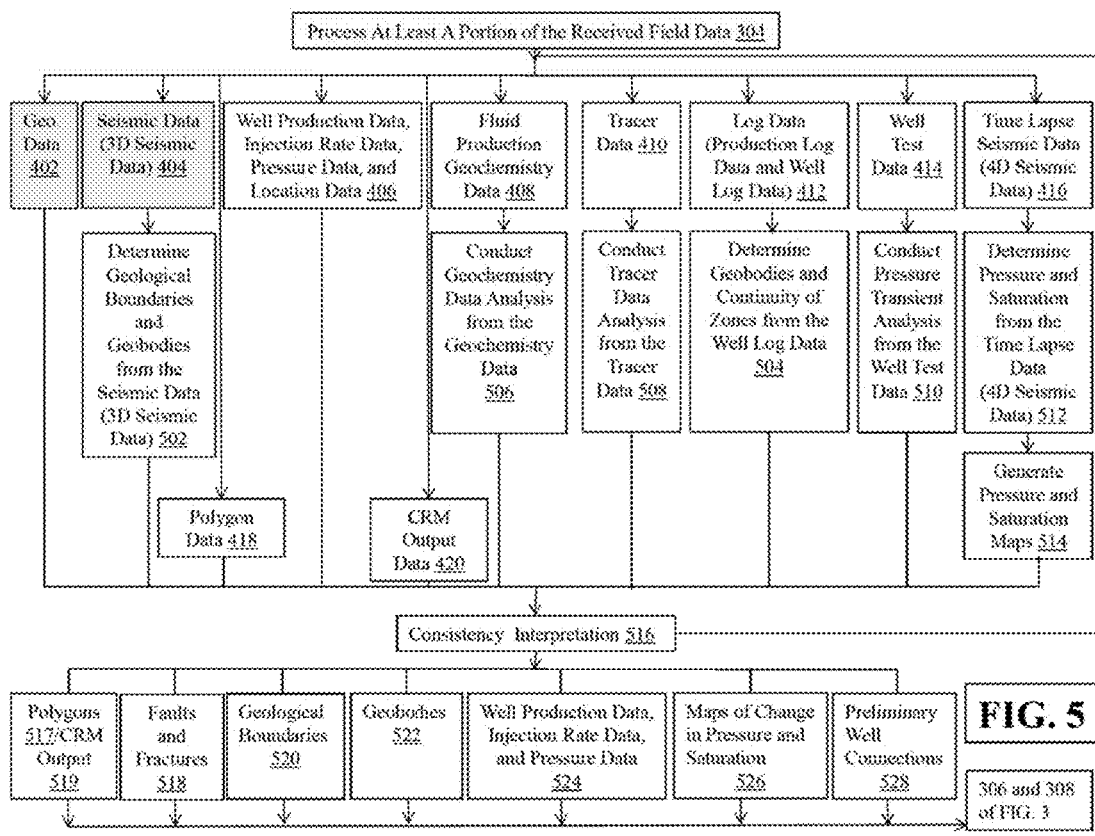

FIG. 4 elaborates on the field data 222 that can be received, with the static data illustrated in gray shading and the dynamic data illustrated with no shading. Examples of field data 222 are illustrated as 402-420, however, the particular field data received for a particular reservoir also depends on the particular field data that is actually gathered for that particular reservoir. For example, if there is both tracer data and 4D seismic data for the particular reservoir, then both of these can be received and used consistent with this disclosure. However, if there is 4D seismic data, but not tracer data, for the particular reservoir, then the 4D seismic data can be received and used consistent with this disclosure. As such, FIG. 4 as well as FIG. 5 illustrate examples of received field data and processing of the received field data, and should not be considered a minimum and not be considered a maximum.

The field data 222 can include static geological data 402 such as porosity, permeability, fracture data (e.g., fracture architecture, fracture locations, etc.), fault data (e.g., fault architecture, fault locations), rock information, etc. The geological data 402 can be determined by users (e.g., by examining core samples, outcrops, etc.), from models, from simulations, any combination thereof, etc.

The field data 222 can include static seismic data such as three dimensional (3D) seismic data 404. The 3D seismic data 404 can be practically any geophysical data measured remotely. For example, the 3D seismic data 404 can be recorded through the use of active seismic sources (e.g., air guns or vibrator units) and receivers (e.g., hydrophones or geophones). The sources and receivers may be arranged in many configurations, and a seismic survey is designed to optimize the source and receiver configurations. Therefore, the 3D seismic data 404 can include seismic surveys, can be recorded by sensors or receivers at the surface 40, can be recorded by sensors or receivers in boreholes, any combination thereof, etc.

The field data 222 can include dynamic well production data (e.g., hydrocarbon volumes produced data or production rate data), injection rate data (or simply injection data), pressure data, and location data 406. For example, the well production data can be received from flow meters (e.g., multiphase flow meters) at the production wells 30, 34, 62, 64, whereas the injection rate data can be received from flow meters at injections wells 32, 66, 68. The pressure data can be received from pressure sensors, as well as other downhole or surface equipment. The location data can include x, y, and z coordinates, and can be received from sensors, GPS equipment, any combination thereof, etc. Of note, the well production data, the injection rate data, the pressure data, and the location data (or depth data) can be at the zonal level, for example, from the zonal application 218 depending on the embodiment.

The field data 222 can include dynamic fluid production geochemistry data 408. For example, the geochemistry data 408 of the produced fluids from the production wells 30, 34, 62, 64 can provide the composition of the produced fluids, such as a listing of the different items in the produced fluid as well as quantity measurements for the different items in the produced fluid. The geochemistry data 408 can be received from equipment, from analysis at the surface 40, from laboratory analysis, any combination thereof, etc.

The field data 222 can include dynamic tracer data 410. A tracer is a material that can be injected with water or other flooding material into the injection well 32 during the flood operation, and the tracer can be detected after a period of time at one or more of the production wells 30, 34, 62, 64 depending on how the wells are linked in the reservoir 20.

The tracer data 410 measures movement of the tracer as it travels through the reservoir 20. The tracer data 410 can be received from equipment, from analysis at the surface 40, from laboratory analysis, any combination thereof, etc.

The field data 222 can include dynamic log data 412, such as well log data and production log data. The field data 222 can also include dynamic well test data 414. For example, well test data can include a production logging test (PLT), an injection logging test (ILT), etc.

The field data 222 can be dynamic seismic data, such as time lapse seismic data, also referred to as four dimensional (4D) seismic data 416. For 4D seismic data 416, a baseline seismic survey is performed to obtain a baseline seismic dataset and subsequent monitoring seismic surveys are performed to obtain one or more monitor seismic dataset(s). Differences between the baseline and the monitor seismic dataset(s) can be analyzed to determine changes in the subsurface reservoir 20 affected by the production and/or injection. The 3D seismic data 404 can be used to determine the 4D seismic data 416.

The field data 222 can be polygon data 418. For example, the polygon data 418 may include polygons indicating geo-bodies, geological boundaries or structural boundaries such as fault or fractures from 3D seismic and/or 4D seismic data, well patterns, etc. The polygons may be overlapping, overlaying, etc. The polygon data 418 may be received from the polygon application or component 216.

The field data 222 can also include CRM output data 420. For example, CRM may be run a plurality of times and the CRM output can be the CRM output data 420.

Those of ordinary skill in the art will appreciate that the listing of field data 222 illustrated in FIG. 4 is not exhaustive. More field data or different field data can be received in some embodiments. For example, as will be discussed hereinbelow, this disclosure expressly contemplates receiving field data at the zonal level (e.g., field data such as production data and injection data at the zonal level from the zonal application 218).

Returning to FIG. 3, at 304, at least a portion of the received field data 222 can be processed. For example, some of the field data 222 received at 302 can be utilized as-is, but at least a portion of the received field data 222 can be processed by a computer executed method only, a user only, or both a computer executed method and a user. Processing the received field data 222 can include analyzing, interpreting, generating additional data, generating maps, generating curves, generating tables, laboratory experiments, etc. Thus, at 304, the received field data 222 can be processed using computer algorithms, manual methodologies, interpretation (e.g., user interpretation), procedures, tests, equipment, etc. For example, the received field data 22 can be processed in a manner known to those of ordinary skill in the art.

FIG. 5 elaborates on the processing of the received field data. At 502, geological boundaries and/or geobodies of the reservoir 20 can be determined from the seismic data (3D seismic data) 404. For example, a petrotechnical application 221 executing on the computing system 200 of FIG. 2A can compute the geological boundaries and/or geobodies of the reservoir 20 from the 3D seismic data 404. The petrotechnical application 221 can be separate from the flooding application 212 or part of the flooding application 221 depending on the embodiment. Furthermore, the geobodies can be determined from the well log data at 504 by the same petrotechnical application 221 or another application (e.g., another pertrotechnical application). At the zonal level, continuity of zones can also be determined from the well log data at 504.

At 506, the geochemistry data analysis can be conducted on the geochemistry data 408. For example, the geochemistry data can be analyzed to determine salinity of produced fluids, determine the amount of water in the produced fluids, determine the various components of the produced fluids (e.g., fingerprinting the oil or produced fluids), etc. The geochemistry data analysis can be conducted at 506 by the same petrotechnical application 221 or another application (e.g., another pertrotechnical application).

At 508, tracer data analysis can be conducted on the tracer data 410. For example, the tracer data from the production wells 30, 34, 62, 64 can be analyzed to determine how fluid flows through the reservoir 20 and for estimating remaining hydrocarbons in the reservoir 20. The tracer data analysis can be conducted at 508 by the same petrotechnical application 221 or another application (e.g., another pertrotechnical application).

At 510, pressure transient analysis can be conducted on the well test data 414. For example, one or more pulse tests can be part of the pressure transient analysis. The tracer data analysis can be conducted at 510 by the petrotechnical application 221 or another application (e.g., another pertrotechnical application).

At 512, pressure and saturation can be determined from the time lapse data (4D seismic data) 416. The pressure and saturation can be computed at 514 by the petrotechnical application 221 or another application (e.g., another pertrotechnical application). Furthermore, at 514, maps can be generated and/or displayed using the determined pressure and saturation by the petrotechnical mapping application 220 or another application (e.g., another pertrotechnical application). The petrotechnical mapping application 220 can be separate from the flooding application 212, separate from the petrotechnical application 221, a part of the petrotechnical application 221, or a part of the flooding analysis application 212 depending on the particular embodiment. The petrotechnical mapping application 220 can be a remaining resource application or component of the flooding analysis application 212, for example, as in U.S. Non-Provisional patent application Ser. No. 13/952,783, filed Jul. 29, 2013, title System and method for remaining resource mapping, which is incorporated by reference in its entirety. Each of the following papers is also incorporated by reference in its entirety: (i) Dietrich, et al, "A Method for Determining Reservoir Fluid Saturations Using Field Production Data", SPE 3961, SPE-AIME 47$^{th}$ Annual Fall Meeting held in San Antonio, Tex. on Oct. 8-11, 1972, and (ii) Gruy, H. J., "Graphing facilitates tracking water and gas influx", Oil & Gas Journal, Mar. 26, 1990, which are both incorporated by reference in their entireties.

For example, maps of estimated change in pressure and water, oil, and/or gas saturation of the reservoir 20 can be generated using data driven approaches that combine observed 4D seismic data or signal with well pressure and production/injection rate as explained further in U.S. Provisional Patent Application No. 62/081,968, filed Nov. 19, 2014, title SYSTEM AND METHOD FOR PRESSURE AND SATURATION ESTIMATION FROM TIME-LAPSE SEISMIC DATA, which is incorporated by reference in its entirety. A copy of the U.S. Provisional Patent Application No. 62/081,968 was included in U.S. Provisional Patent Application No. 62/135,016, which is incorporated herein by reference in its entirety. Alternatively, or additionally, maps of estimated change in pressure and water, oil, and/or gas saturation of the reservoir 20 can be generated using model driven approaches that use physics modeling to estimate changes of pressure and saturation from 4D seismic data or signal. Alternatively, or additionally, maps of seismic attributes can be computed from 4D seismic data or signal.

Indeed, the pressure and saturation, and maps thereof, can include qualitative visualization of cross sections and map views of 4D seismic amplitudes (e.g., by a computer executed method only, a user only, or both a computer executed method and a user) and/or qualitative visualization of cross sections and map views of seismic impedances from inversion of seismic data (e.g., by a computer executed method only, a user only, or both a computer executed method and a user). Of note, although maps can be generated and displayed to a user, in some embodiments, maps do not need to be generated and displayed to a user.

The various items 502-514 and 402-420 can be checked for consistency at 516. For example, at least a portion of the various items 502-514 and 402-420 can be reviewed for accuracy, contradictions, and overall consistency by a computer executed method only, a user only, or both a computer executed method and a user. The consistency interpretation at 516 can be performed by computerized methods only, users only, or both computerized methods and users depending on the embodiment. If any inconsistencies are found, control can pass to 304 to continue to re-process as appropriate and as many times as appropriate. The loop and iterations can continue until a sufficient level of consistency is reached.

The various items 502-514 and 402-416, after the consistency check, can lead to results 518-528. For example, the results 518-528 can include (i) the faults and the fractures (518) from the geological data (402), (ii) the geological boundaries (520) from the 3D seismic data (502, 404), (iii) the geobodies (522) from the 3D seismic data (502, 404) and/or the well log data (504, 412), (iv) the well production data, injection rate data, and the pressure date (524) from 406, (v) maps of change in pressure and saturation (526) from the 4D seismic data and/or the pressure and saturation maps (514, 512, 416), (vi) polygons 517 from the polygon data 418, and/or (vii) interwell connectivities and response times from the CRM output data 420. Moreover, the results include preliminary well connections (528) or evidence thereof, for example, from the tracer data analysis (508, 410) and/or the pressure transient analysis (510, 414). This listing of results is not exhaustive and other results can also be included.

Figure 3:
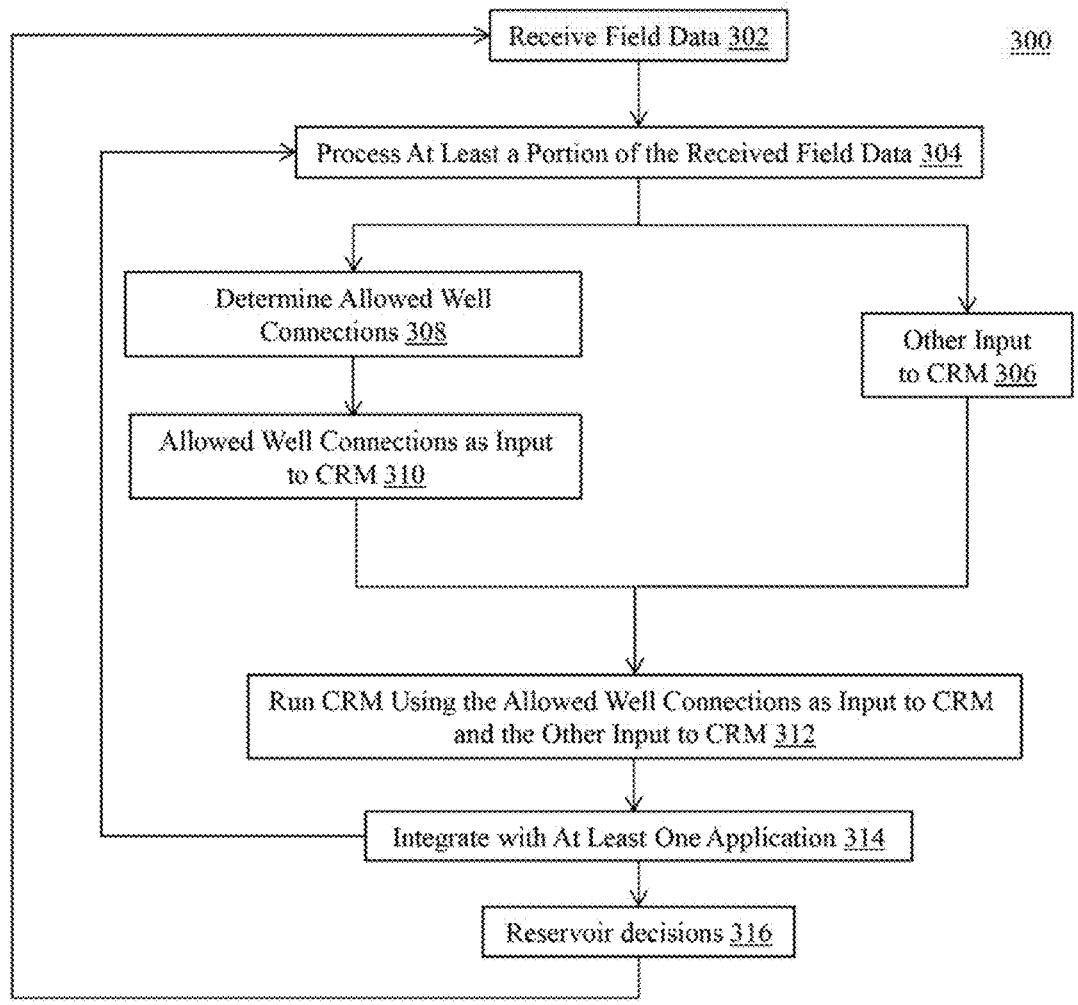
FIGS. 3-5 illustrate one embodiment of a computer implemented method to analyze a flood operation.

Returning to 306, 308, 310 of FIG. 3, practically any available data at this point (e.g., the received field data 402-416 and the processed field data (or interpreted field data) 502-514 and 518-528), can be used for input to CRM and/or to determine allowed well connections at 308, 310 and the allowed well connections are input to CRM. For example, injection rates and production rates can be used as input to CRM. Therefore, the well production data and the injection rate data 406 can be used as input to CRM at 306.

However, consistent with this disclosure, input to CRM will also include allowed well connections, not just the well production data and the injected rate data 406. In a particular example, some but not all of the preliminary well connections 528 will be allowed well connections depending on the determination. The allowed well connections can be determined at 308 from at least a portion of available data at this point (e.g., the received field data 402-416 and the processed field data (or interpreted field data) 502-514 and 518-528 illustrated in FIG. 5). For example, in some embodiments, time lapse seismic data (4D seismic data), including interpreted time lapse seismic data (interpreted 4D seismic data) and any of 416, 512, 514, can be used as an input to CRM and/or to determine allowed well connections and the allowed well connection are input to CRM. Interpreted time lapse seismic data (interpreted 4D seismic data) can be generated by, for example, at least one of:

(a) maps of estimated change in pressure and water, oil, and/or gas saturation of the reservoir generated using data driven approaches that combine observed 4D seismic data or signal with well pressure and production/injection rate as explained further in U.S. Provisional Patent Application No. 62/081,968, filed Nov. 19, 2014, title SYSTEM AND METHOD FOR PRESSURE AND SATURATION ESTIMATION FROM TIME-LAPSE SEISMIC DATA, which is incorporated by reference in its entirety—a copy of the U.S. Provisional Patent Application No. 62/081,968 was included in U.S. Provisional Patent Application No. 62/135,016, which is incorporated herein by reference in its entirety, (b) maps of estimated change in pressure and water, oil, and/or gas saturation of the reservoir generated using model driven approaches that use physics modeling to estimate changes of pressure and saturation from 4D seismic data or signal, (c) maps of seismic attributes computed from 4D seismic data or signal, (d) qualitative visualization of cross sections and map views of 4D seismic amplitudes (e.g., by computerized methods, interpretation by a user, or both computerized methods and interpretation by a user), and/or (e) qualitative visualization of cross sections and map views of seismic impedances from inversion of seismic data (e.g., by computerized methods, interpretation by a user, or both computerized methods and interpretation by a user).

Although maps can be generated and displayed to a user, in some embodiments, maps do not need to be generated and displayed to a user. Therefore, interpreted time lapse seismic data can be generated by the data behind the maps via computerized methods, interpretation by a user, or both computerized methods and interpretation by a user. Nonetheless, the allowed well connections can be determined at 308 from at least a portion of available data at this point (e.g., the received field data 402-416 and the processed field data (or interpreted field data) 502-514 and 518-528 illustrated in FIG. 5). Moreover, any of this available data can be used for input to CRM and/or to determine allowed well connections at 308, 310 and the allowed well connections are the input to CRM. For example, in some embodiments, time lapse seismic data (4D seismic data), including interpreted time lapse seismic data (interpreted 4D seismic data) and any of 416, 512, 514, can be used as an input to CRM and/or to determine allowed well connections and the allowed well connection are input to CRM. Moreover, in some embodiments, time lapse seismic data (4D seismic data), including interpreted time lapse seismic data (interpreted 4D seismic data) and any of 416, 512, 514, along with other data (e.g., tracer data) can be used as an input to CRM and/or to determine allowed well connections and the allowed well connection are input to CRM. In short, practically any of the data available at this point can be used as input to CRM (e.g., constraints to CRM) and/or to determined allowed well connections that will be input to CRM (e.g., constraints to CRM).

Figure 6:
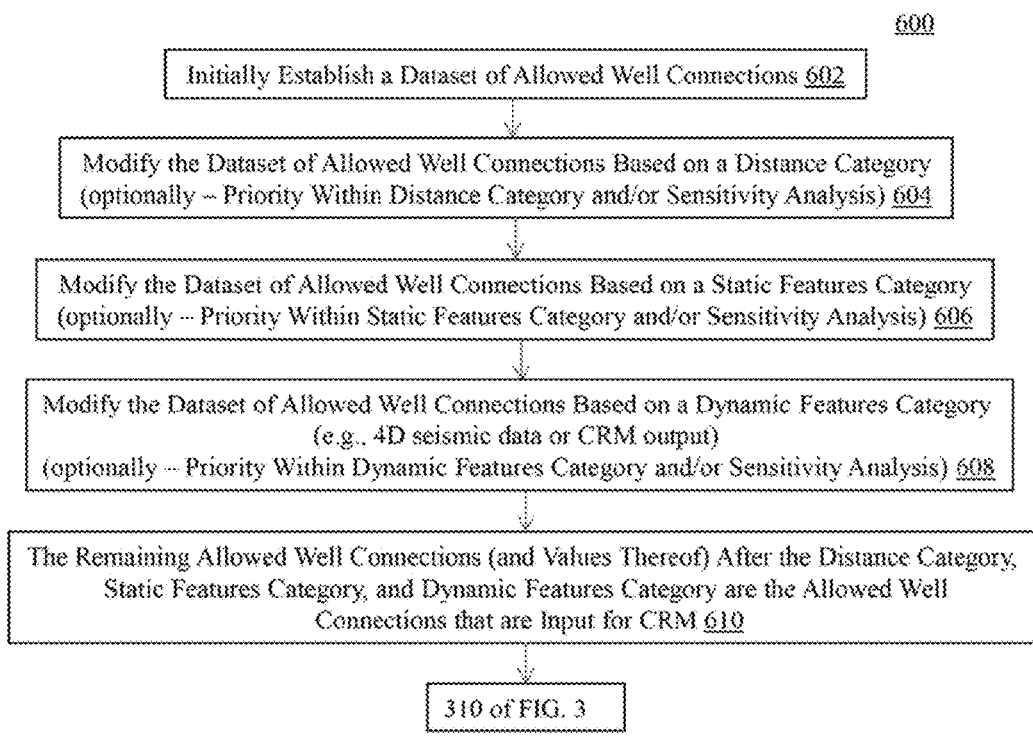
FIG. 6 illustrates one embodiment of a method for determining the allowed well connections.

FIG. 6 provides a method 600, which is an embodiment of a method for determining the allowed well connections. The method 600 can be executed by the CRM application 214. In some embodiments, the method 600 can be iterative, and allowed well connections can be determined for each injection well and production well pair. The method 600 can be executed for multiple injection wells or executed per injection well. The dataset of allowed well connections may be modified (e.g., iteratively) based on a distance category, a static features category, a dynamic features category, or any combination thereof. For example, the database of allowed well connections may be modified as will be discussed below in connection with 604, 606, 608. For ease of understanding, a running example for determining allowed connections will be discussed in the context of FIGS. 7-10. For simplicity, the running example will focus on injection wells Inj-05 and Inj-08 and production wells Pro-01 through Pro-12. Bold and strikethrough are used to indicate the changes between iterations.

The method 600 can be accomplished by a computer executed method only, a user only, or both a computer executed method and a user. In some embodiments, the order of distance, then static features, and then dynamic features of the method 600 can also be changed such that the dynamic features are higher priority and used first, then the static features, then the distance. Moreover, within each category, there can also be a priority (e.g., geobodies have a higher priority than geological boundaries or permeability, or vice versa, within the static feature category) (e.g., 4D seismic data or the pressure and saturation from 4D seismic data has a higher priority than tracer data, or vice versa, within the dynamic features category). Thus, there can be a priority between categories (e.g., dynamic features, then static features, then distance) and/or a priority within a category (e.g., geobodies have a higher priority than permeability within the static feature category or vice versa). Moreover, a sensitivity analysis can be run for each category and the allowed well connections per category can be based on the sensitivity analysis per category.

In a computer method only implementation of method 600, the computer method can rely on location data, boundaries, thresholds such as if the production well is within a number of feet or percentage outside of a geobody or saturation and pressure map boundary, and other data to determine the allowed well connections. Furthermore, it can display the corresponding diagrams/maps as in FIGS. 7-10, but it does not need to display the diagrams/maps. In some embodiments, a user can determined the allowed well connections as indicated in method 600, or revise the allowed well connections determined by a computer method only implementation. For example, the user can do so if he or she wants to use more flexibility and expertise, and not thresholds, in deciding whether a production well is connected or not to an injection well.

At 602, a dataset of allowed well connections can be established. The values for the allowed well connections can be initially established by indicating that a well connection exists for each injection well and production well pair. For example, a value of 1, yes, or other indication can be used to indicate a well connection between an injection well and a production well. In the running example, at 602, the dataset of allow well connections may indicate that each injection well can potentially support each production well, in other words, that there is a well connection between every production well and each injection well, as illustrated below:

TABLE 1

| Dataset of allowed well connections | ... | Inj-05 | ... | Inj-08 |
|---|---|---|---|---|
| Pro-01 | | 1 | | 1 |
| Pro-02 | | 1 | | 1 |
| Pro-03 | | 1 | | 1 |
| Pro-04 | | 1 | | 1 |
| Pro-05 | | 1 | | 1 |

TABLE 1-continued

| Dataset of allowed well connections | ... | Inj-05 | ... | Inj-08 |
|---|---|---|---|---|
| Pro-06 | | 1 | | 1 |
| Pro-07 | | 1 | | 1 |
| Pro-08 | | 1 | | 1 |
| Pro-09 | | 1 | | 1 |
| Pro-10 | | 1 | | 1 |
| Pro-11 | | 1 | | 1 |
| Pro-12 | | 1 | | 1 |

At 604, the dataset of allowed well connections can be modified based on a distance category (e.g., inverse distance). For example, a value of 1 for a particular injection well and production well pair is changed from 1 to 0 to indicate that a well connection does not exist based on distance for that particular injection well and production well pair. Alternatively, the value is kept at 1 if the well connection exists based on the distance category. A priority between categories may be received from a user, for example, and the priority may indicate that the distance category is first. Similarly, a priority within the distance features category may be used and received from a user. A user may designate the data that will be part of the distance category.

Figure 7:
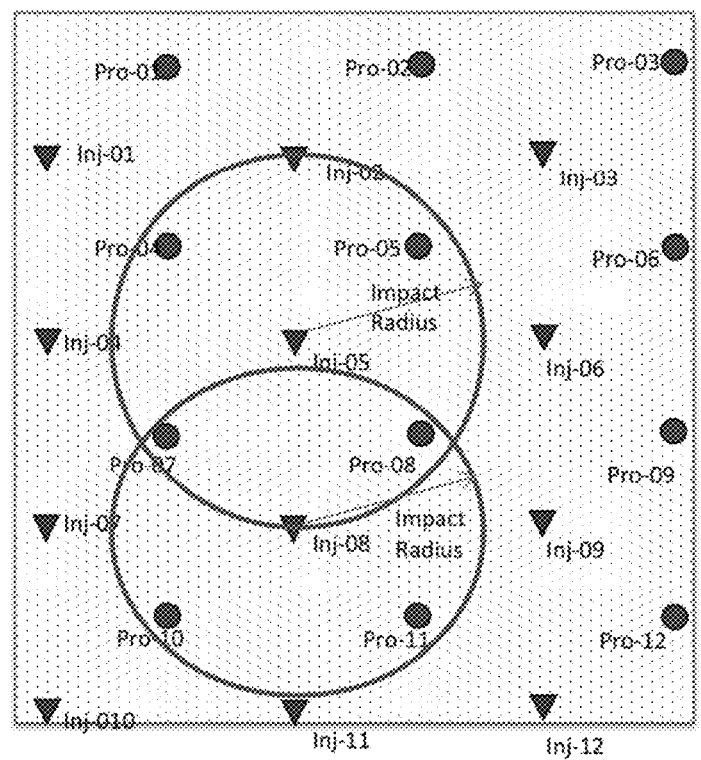
FIGS. 7-10 illustrate examples consistent with the embodiment of FIG. 6.
Figure 8:
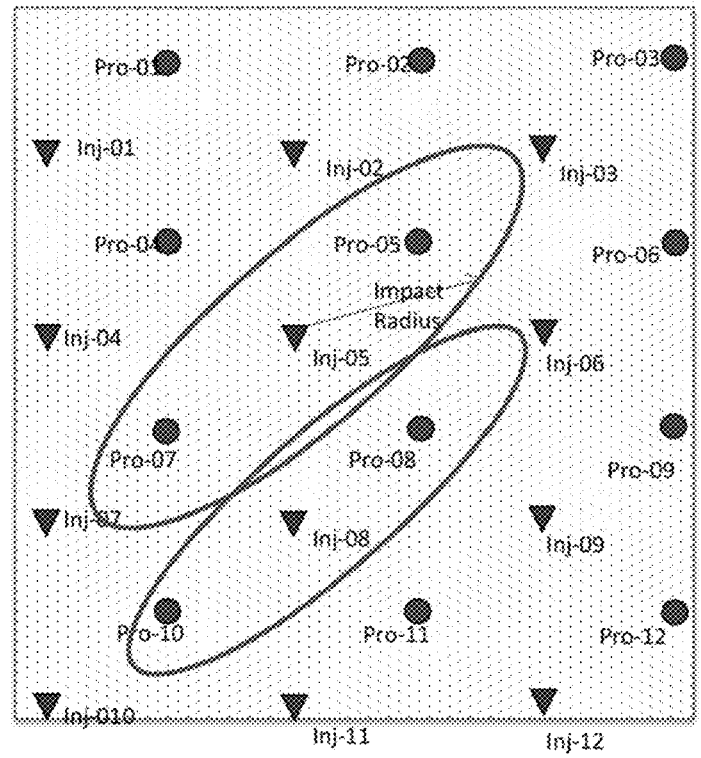

Returning to the running example, the diagrams or maps at FIGS. 7-8 may be used to illustrate the distance category. Regarding permeability in FIG. 8, permeability can be treated as distance (FIG. 8) or as a static feature (FIG. 9) depending on the embodiment. In the running example, at 604, the dataset of allowed well connections may be modified according to the distance illustrated in the diagram of FIG. 7 to indicate allowed well connections between the Inj-05 and Pro-04 pair, the Inj-05 and Pro-05 pair, the Inj-05 and Pro-07 pair, the Inj-05 and Pro-08 pair, the Inj-08 and Pro-07 pair, the Inj-08 and Pro-08 pair, the Inj-08 and Pro-10 pair, and the Inj-08 and Pro-11 pair, as illustrated below:

TABLE 2

| Dataset of allowed well connections modified by distance category per FIG. 7 | ... | Inj-05 | ... | Inj-08 |
|---|---|---|---|---|
| Pro-01 | | ~~1~~ 0 | | ~~1~~ 0 |
| Pro-02 | | ~~1~~ 0 | | ~~1~~ 0 |
| Pro-03 | | ~~1~~ 0 | | ~~1~~ 0 |
| Pro-04 | | 1 | | ~~1~~ 0 |
| Pro-05 | | 1 | | ~~1~~ 0 |
| Pro-06 | | ~~1~~ 0 | | ~~1~~ 0 |
| Pro-07 | | 1 | | 1 |
| Pro-08 | | 1 | | 1 |
| Pro-09 | | ~~1~~ 0 | | ~~1~~ 0 |
| Pro-10 | | ~~1~~ 0 | | 1 |
| Pro-11 | | ~~1~~ 0 | | 1 |
| Pro-12 | | ~~1~~ 0 | | ~~1~~ 0 |

Alternatively, in the running example, at 604, the dataset of allowed well connections may be modified according to the distance illustrated in the diagram of FIG. 8 to indicate allowed well connections between the Inj-05 and Pro-05 pair, the Inj-05 and Pro-07 pair, the Inj-08 and Pro-08 pair, and the Inj-08 and Pro-10 pair, as illustrated below:

TABLE 3

| Dataset of allowed well connections modified by distance category per FIG. 8 | ... | Inj-05 | ... | Inj-08 |
|---|---|---|---|---|
| Pro-01 | | ~~1~~ 0 | | ~~1~~ 0 |
| Pro-02 | | ~~1~~ 0 | | ~~1~~ 0 |

TABLE 3-continued

| Dataset of allowed well connections modified by distance category per FIG. 8 | ... | Inj-05 | ... | Inj-08 |
|---|---|---|---|---|
| Pro-03 | | ~~0~~ | | ~~0~~ |
| Pro-04 | | ~~0~~ | | ~~0~~ |
| Pro-05 | | 1 | | ~~0~~ |
| Pro-06 | | ~~0~~ | | ~~0~~ |
| Pro-07 | | 1 | | ~~0~~ |
| Pro-08 | | ~~0~~ | | 1 |
| Pro-09 | | ~~0~~ | | ~~0~~ |
| Pro-10 | | ~~0~~ | | 1 |
| Pro-11 | | ~~0~~ | | ~~0~~ |
| Pro-12 | | ~~0~~ | | ~~0~~ |

As in the running example, within the distance category, the distance associated with FIG. 7 and the permeability associated with FIG. 8 led to different well connections for the distance category. To resolve the conflict, modifying the dataset of allowed well connections according the distance category may include using a priority within the distance category. In the running example, distance was selected over permeability and therefore the distance was given the higher priority within the distance category for determining the well connections. If the running example included a second distance in addition to the distance of FIG. 7 and the permeability of FIG. 8, then the highest priority within the distance category may be the second distance, then distance of FIG. 7, then the permeability of FIG. 8 for the allowed connections.

At 606, the dataset of allowed well connections can be modified based on a static features category such as geological facies, etc. (e.g., same geobody from 3D seismic data, permeability, etc.). The static features category uses static data of the hydrocarbon reservoir, and the static data may include geological data, seismic data, three dimensional (3D) seismic data, faults, fractures, geobodies, geological boundaries, a processed version of any of these, or any combination thereof. If a particular injection well and production well pair indicates a value of 1, yes, or some other indication that the well connection does exist based on distance, but the static features suggest that a well connection does not exist for that pair, then the value for that well connection for that pair can be changed to 0, no, or some other indication. By doing so, the static features have a higher priority than distance, thereby selecting the highest priority. The priority between categories may be received from a user. Similarly, a priority within the static features category may be used and received from a user. A user may designate the data that will be part of the static features category.

Figure 9:
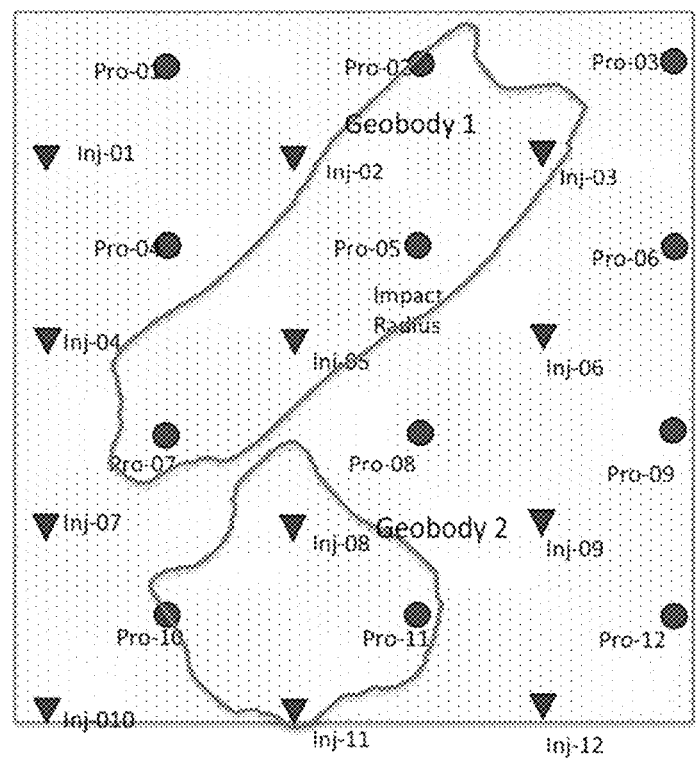

Returning to the running example, the diagram or map at FIG. 9 may be used to illustrate the static features category. Assuming the previous values associated with FIG. 7, in the running example, at 606, the dataset of allowed well connections may be modified according to the static features (e.g., geobodies 1 and 2 from geological study and 3D seismic data) illustrated in the diagram of FIG. 9 to indicate allowed well connections between the Inj-05 and Pro-02 pair, the Inj-05 and Pro-05 pair, the Inj-05 and Pro-07 pair, the Inj-08 and Pro-08 pair, the Inj-08 and Pro-10 pair, the Inj-08 and Pro-11 pair, and the Inj-08 and Pro-11 pair, as illustrated below:

TABLE 4

| Dataset of allowed well connections modified by static features category per FIG. 9 | ... | Inj-05 | ... | Inj-08 |
|---|---|---|---|---|
| Pro-01 | | ~~0~~ | | ~~0~~ |
| Pro-02 | | ~~0~~ 1 | | ~~0~~ |
| Pro-03 | | ~~0~~ | | ~~0~~ |
| Pro-04 | | ~~0~~ | | ~~0~~ |
| Pro-05 | | 1 | | ~~0~~ |
| Pro-06 | | ~~0~~ | | ~~0~~ |
| Pro-07 | | 1 | | ~~0~~ |
| Pro-08 | | ~~0~~ | | 1 |
| Pro-09 | | ~~0~~ | | ~~0~~ |
| Pro-10 | | ~~0~~ | | 1 |
| Pro-11 | | ~~0~~ | | 1 |
| Pro-12 | | ~~0~~ | | ~~0~~ |

At 608, the database of allowed well connections can be modified based on a dynamic features category such as 4D seismic data, tracer data analysis, pressure transient analysis, etc. (e.g., connected geobody from 4D seismic data). The dynamic features category uses dynamic data of the hydrocarbon reservoir, and the dynamic data may include well production data, injection rate data, pressure data, location data, fluid production geochemistry data, tracer data, log data, production log data, well log data, well test data, time lapse seismic data, four dimensional (4D) seismic data, maps of change in pressure and saturation, maps of pressure and saturation, preliminary well connections, pressure transient, pulse test, capacitance resistance modeling output data, polygon data, a processed version of any of these, or any combination thereof. If a particular injection well and production well pair indicates a value of 1, yes, or some other indication that the well connection does exist based on the static features, but the dynamic features suggest that a well connection does not exist for that pair, then the value for that well connection for that pair can be changed to 0, no, or some other indication. By doing so, the dynamic features have a higher priority than static features, thereby selecting the higher priority. The priority between categories may be received from a user. Similarly, a priority within the dynamic features category may be used and received from a user. A user may designate the data that will be part of the dynamic features category.

Figure 10:
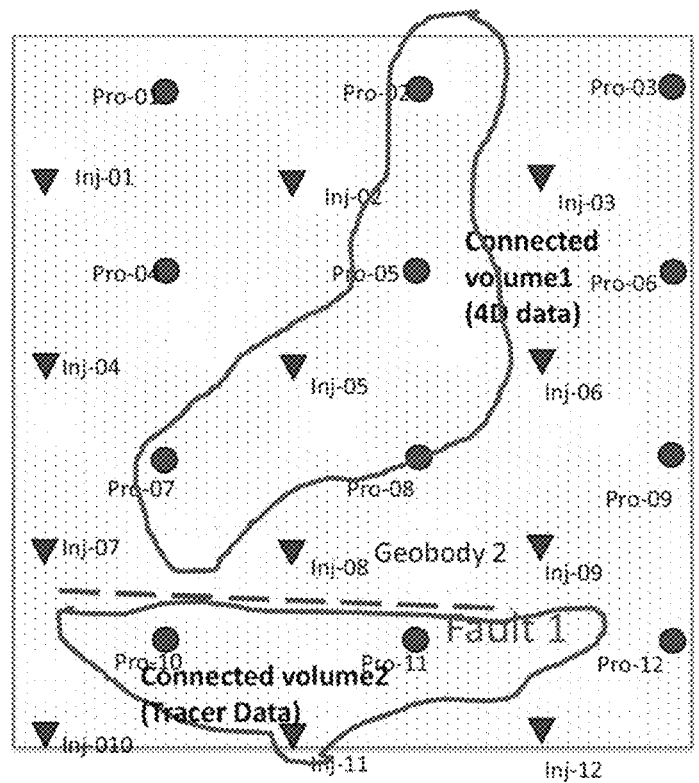

Returning to the running example, the diagrams and maps at FIG. 10 may be used to illustrate the dynamic features category. Assuming the previous values associated with FIG. 9, in the running example, at 608, the dataset of allowed well connections may be modified according to the dynamic features (e.g., connected volume1-4D data and connected volume2-tracer data) illustrated in the diagram of FIG. 10 to indicate allowed well connections between the Inj-05 and Pro-02 pair, the Inj-05 and Pro-05 pair, the Inj-05 and Pro-07 pair, the Inj-05 and Pro-08 pair, and no well connections for Inj-08 but for Inj-11 instead, as illustrated below:

TABLE 5

Dataset of allowed well connections modified by dynamic features category per FIG. 10

| | Inj-... 05 | Inj-... 08 | Inj-... 11 |
|---|---|---|---|
| Pro-01 | ~~0~~ | ~~0~~ | |
| Pro-02 | ~~0~~ 1 | ~~0~~ | |
| Pro-03 | ~~0~~ | ~~0~~ | |
| Pro-04 | ~~0~~ | ~~0~~ | |
| Pro-05 | 1 | ~~0~~ | |
| Pro-06 | ~~0~~ | ~~0~~ | |
| Pro-07 | 1 | ~~0~~ | |
| Pro-08 | ~~0~~ 1 | ~~0~~ | |
| Pro-09 | ~~0~~ | ~~0~~ | |
| Pro-10 | ~~0~~ | ~~0~~ | 1 |
| Pro-11 | ~~0~~ | ~~0~~ | 1 |
| Pro-12 | ~~0~~ | ~~0~~ | |

Of note, the dynamic features category indicates that Pro-10 and Pro-11 are connected to Inj-11 instead of Inj-08 based on the connected volume 1 (4D seismic data) and connected volume2 (tracer data). FIG. 10 also illustrated a sealing fault referred to as the fault1. The fault1, which may be considered in the static features category, further confirms that Pro-10 and Pro-11 are connected to Inj-11 instead of Inj-08. Thus, a combination of static features and dynamic features can also be used together as a category (e.g., during one iteration) in some embodiments, as illustrated in FIG. 10 with the fault1, the 4D seismic data, and the tracer data.

Furthermore, a sensitivity analysis can be run for each category and the allowed well connections per category can be based on the sensitivity analysis per category. For example, the values in Table 2 for the distance category may be based on a sensitivity analysis for the distance category. In the sensitivity analysis, a first distance may lead to first values, a second distance may lead to second values, a third distance may lead to third values, and so on, and if the value of 1 appears the most for a well pair then the value of 1 is selected for that well pair but if the value of 0 appears the most for a well pair then the value of 0 is selected for that well pair. A similar approach can be pursued for the static features category, the distance features category, or both. The sensitivity analysis for category may try to account for the variability (e.g., variability of a particular data item in that category such as first 4D seismic data, second 4D seismic data, etc. in the dynamic features category or first geological boundary, second geological boundary, etc. in the static features category) and potentially increase the accuracy of the allowed well connections for the category, and in turn potentially increase the accuracy of the final allowed well connections that are input to CRM.

At 610, the remaining well connections (and values thereof) after the distance, static features, and dynamic features are the allowed well connections 308 that are input for CRM. As illustrated above, out of 24 possible well pairs including Inj-05 and Inj-08, there are 4 allowed well connections namely the Inj-05 and Pro-02 pair, the Inj-05 and Pro-05 pair, the Inj-05 and Pro-07 pair, and the Inj-05 and Pro-08 and none for Inj-08. The dataset of allowed well connections in Table 6 may be used as input for CRM. Alternatively, the dataset of allowed well connections provided as input to CRM may only include the well connections with a value of 1.

TABLE 6

| Dataset of allowed well connections | ... Inj-05 | ... Inj-08 | ... Inj-11 |
|---|---|---|---|
| Pro-01 | 0 | 0 | |
| Pro-02 | 1 | 0 | |
| Pro-03 | 0 | 0 | |
| Pro-04 | 0 | 0 | |
| Pro-05 | 1 | 0 | |
| Pro-06 | 0 | 0 | |
| Pro-07 | 1 | 0 | |
| Pro-08 | 1 | 0 | |
| Pro-09 | 0 | 0 | |
| Pro-10 | 0 | 0 | 1 |
| Pro-11 | 0 | 0 | 1 |
| Pro-12 | 0 | 0 | |

After running CRM, the output of CRM may be used to further modify the dataset of allowed well connections. For example, the output of CRM such as the interwell connectivities (and Tau's) may be used to confirm well connections, add a new well connection (e.g., change 0 value to a 1 value for a well pair in the dataset of allowed well connections), remove a well connection (e.g., change 1 value to a 0 value for a well pair in the dataset of allowed well connections), etc. As an example, an interwell connectivity value of 0 or below a threshold for a particular well pair can lead to removing a well connection for that particular well pair by selecting 0 for that well pair in the dataset of allowed well connections. Indeed, CRM output available before or after running CRM may be treated as part of the dynamic features category to remove or add at least one allowed well connection to the dataset of allowed well connections. For instance, if dynamic data like tracer indicates no connection exists between a particular well pair while pulse test indicates a connection does exist between that same well pair, and then the value can be set to 1 for the well pair if pulse test has a higher priority but after running CRM, the CRM output indicates that the pulse test was incorrect so the value is changed to 0 to indicate no well connection for that well pair. The dataset of allowed well connections revised with the CRM output may be used as the initial dataset at 602.

Furthermore, those of ordinary skill in the art will appreciate that various modification can be made to the disclosed embodiments. For example, in some embodiments, the initial dataset of allowed well connections can be based on the distance category, instead of assuming all well connections exist, and the initial dataset of allowed well connections may be modified based on the static features category, the dynamic features category, or both. Similarly, in some embodiments, the initial dataset of allowed well connections can be based on the dynamic features category, instead of assuming all well connections exist, and the initial dataset of allowed well connections may be modified based on the static features category, the distance category, or both. Similarly, the initial dataset of allowed well connections can be based on previously determined allowed well connections. In some embodiments, all or fewer than all categories may be used to determine the allowed well connections (e.g., the static features category only, the dynamic features category only, or both). Furthermore, data may be received at different points (e.g., not just at 602), and therefore the dataset of allowed well connections may be modified a plurality of times before the allowed well connections are used as input to CRM.

Figure 11:
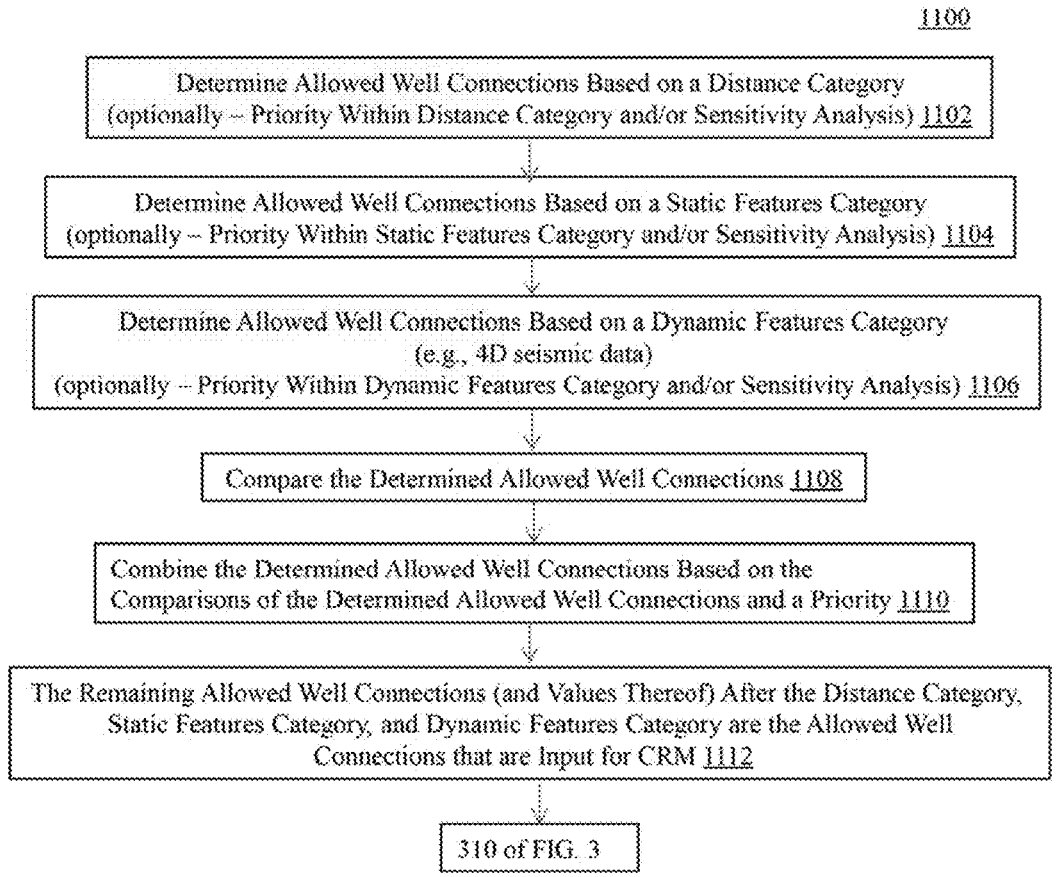
FIG. 11 is another embodiment of a method for determining allowed well connections.

FIG. 11 provides a method 1100, which is another embodiment of a method for determining allowed well connections. The method 1100 can be executed by the CRM application 214. The method 600 modifies a single dataset of allowed well connections whereas the method 1100 can generate a plurality of datasets (e.g., one dataset for a dynamic features category, one dataset for a static features category, and one data set for a distance category) and the plurality of datasets can be combined into a single dataset of allowed well connections based on priority.

At 1102, the method 1100 includes determining well connections based on a distance category (e.g., inverse distance). At 1104, the method 1100 includes determining allowed well connections based on a static features category such as geological facies, etc. (e.g., same geobody from 3D seismic data). At 1106, the method 1100 includes determining allowed well connections based on a dynamic features category such as 4D seismic data, tracer data analysis, pressure transient analysis, etc. (e.g., connected geobody from 4D seismic data). At 1108, the method 1100 includes comparing the determined allowed well connections. At 1110, the method 1100 includes combining the determined allowed well connections from the various datasets based on the comparisons and a priority (e.g., combining based on the dynamic features category having the highest priority of the three, then the static features category having the next higher priority, and then the distance category) into a combined dataset of allowed well connections. At 1112, the remaining allowed well connections after the distance, static features, and dynamic features are combined are the allowed well connections 310 that are input for CRM.

Figure 12:
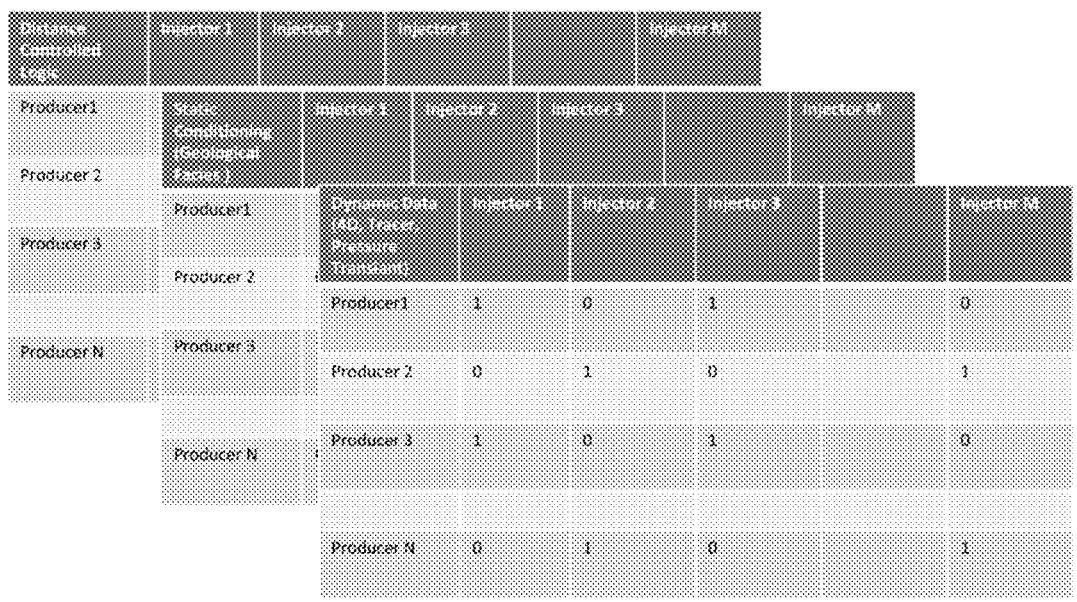
FIG. 12 illustrates an example consistent with the embodiment of FIG. 11.
Figure 13:
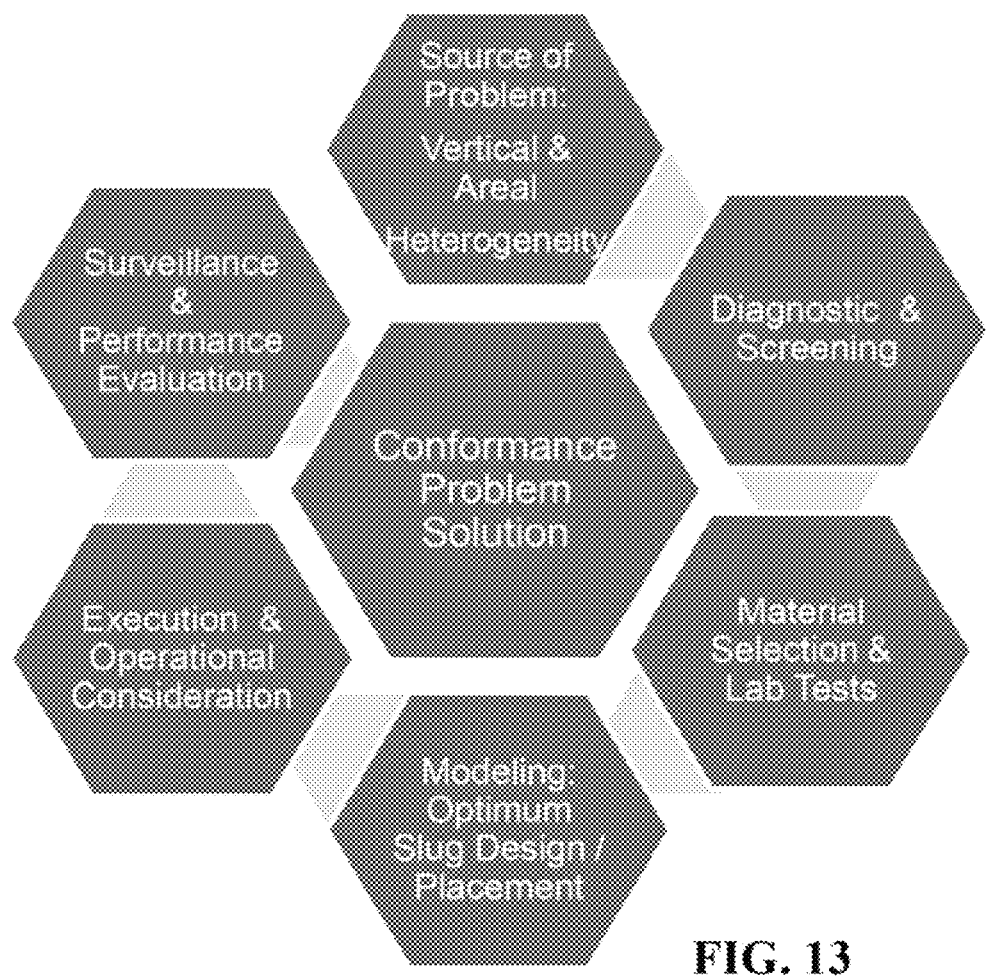
FIG. 13 illustrates one example of a conformance control workflow.

FIG. 12 provides an example consistent with the method 1100 and illustrates one dataset per category. The three datasets can be combined into one dataset of allowed well connections for input to CRM. Similarly, various datasets can be generated from FIGS. 7-10 and combined according to method 1100.

The method 1100 can be accomplished by a computer executed method only (e.g., using thresholds, boundaries, location data, etc.), a user only (e.g., for more flexibility), or both a computer executed method and a user (e.g., for more flexibility) as described hereinabove for method 600. Furthermore, in some embodiments, the order of distance, then static features, and then dynamic features of the method 600 can also be changed in the method 1100 such that the dynamic features are higher priority and used first at 1102, then the static features, then the distance. Moreover, there can be a priority between categories (e.g., dynamic features, then static features, then distance) and/or a priority within a category (e.g., geobodies have a higher priority than permeability within the static feature category or vice versa). Furthermore, as discussed in connection with FIG. 6, the priority between categories may be received from a user. Similarly, a priority within a category may be used and received from a user. Sensitivity analysis per category may also be performed. Moreover, a user may designate the data that will be part of the categories. After running CRM, the output of CRM may also be used to further modify the allowed well connections.

Returning to FIG. 3, at 312, CRM can be run using the allowed well connections as input to CRM from 310 and the other input to CRM from 306. For example, the CRM application 214 can run CRM to quantify the interwell connectivities using techniques known in the art, such as those in the documents incorporated herein. However, consistent with this disclosure, CRM can be modified to quantify the interwell connectivities in a manner that is consistent with the available data (e.g., from FIG. 5), consistent with the allowed well connections determined in FIGS. 6, 11 that are input, etc. In other words, CRM can be provided with constraints to enforce consistency with the available data (e.g., the 4D seismic data, the pressure and saturation from the 4D seismic data, the pressure and saturation maps, etc.) and the allowed well connections. Table 7 (below) illustrates an example of potential interwell connectivities that can be generated by CRM:

TABLE 7

Interwell Connectivities ($F_{ij}$) generated with allowed well connections as an input to CRM

| | ... | Inj-05 | ... | Inj-08 | ... | Inj-11 |
|---|---|---|---|---|---|---|
| Pro-01 | | 0 | | 0 | | |
| Pro-02 | | .1 | | 0 | | |
| Pro-03 | | 0 | | 0 | | |
| Pro-04 | | 0 | | 0 | | |
| Pro-05 | | .3 | | 0 | | |
| Pro-06 | | 0 | | 0 | | |
| Pro-07 | | .4 | | 0 | | |
| Pro-08 | | .2 | | 0 | | |
| Pro-09 | | 0 | | 0 | | |
| Pro-10 | | 0 | | 0 | | .3 |
| Pro-11 | | 0 | | 0 | | .2 |

At 314, practically any data available thus far can be integrated with at least one application or component by a computer executed method only, a user only, or both a computer executed method and a user. For example, the data available at this point can be the most current data (e.g., the most current interwell connectivities determined by CRM, the most current allowed well connections, the most current 4D seismic data, the most current pressure and saturation from the 4D seismic data, etc.). An application that uses or receives as input that type of data can be updated to integrate the data, for example, the application can be the petrotechnical mapping application 220, a simulation application, etc. such as illustrated in FIG. 2A, 2C.

Furthermore, at 314, additional interpretation can occur. For example, the additional interpretation can be a check for consistency, can find any inconsistencies, etc., which may also lead to integration of data into at least one application. The interpretation can happen before or after integration of data into at least one application. Control can pass to 304 to restart the loop.

At 316, reservoir decisions can be addressed. For example, a recommendation can automatically be generated based on the available data. Alternatively, a user can make at least one reservoir decision based on the available data. The reservoir decisions can relate to optimization, history matching, conformance control, changing a parameter of the flood operation, etc., for example, to improve the flood operation. Control can pass to 302 to restart the loop to receive more field data 222.

At the zonal level, a similar approach can be used. In some embodiments, each zone may be treated as an injection well, and allowed well connections for each injection well/zone and production well pair can be determined as described hereinabove in FIGS. 6, 11. For example, at 302, the received field data can include zonal splits data from the zonal application 218 that indicates the percentage of water, oil, gas, and/or injection (e.g., water injection) per zone. At 304, the received field data at the zonal level can be further processed as illustrated in FIG. 3, for example, to determine continuity of zones from the well log data 504. At 308, 310, the allowed well connections at the zonal level can be determined as illustrated in FIGS. 6, 11 and an example is illustrated below at Table 8.

In Table 8, 0's and 1's are illustrated for each zone and production well pair. Table 8 assumes the existence of 3 zones in the reservoir, a plurality of injection wells, and a plurality of production wells. Table 8 also assumes that only the injection well Inj-01 has perforations and fluidic contact with the three zones. In this example, there are 10 allowed well connections out of a possible 15 because the analysis is at the zonal level. At the well level, there would have been 9 possible allowed well connections, but Table 8 illustrates 10 allowed well connections out of a possible 15 at the zonal level:

TABLE 8

| | Dataset of allowed well connections at the zonal level | | | | |
|---|---|---|---|---|---|
| | Inj-01 zone-01 | Inj-01 zone-02 | Inj-01 zone-03 | Inj-02 | Inj-03 ... |
| Pro-01 | 0 | 0 | 1 | 1 | 1 |
| Pro-02 | 1 | 1 | 0 | 1 | 1 |
| Pro-03 | 1 | 0 | 0 | 1 | 1 |
| ... | | | | | |

Furthermore, as discussed in connection with FIGS. 6, 11, a priority between categories may be used and received from a user. Similarly, a priority within a category may be used and received from a user. Sensitivity analysis per category may also be performed. Moreover, a user may designate the data that will be part of the categories.

At 312, CRM can be run using the allowed well connections at the zonal level as input to CRM and the other input to CRM. After running CRM, the output of CRM may also be used to further modify the allowed well connections at the zonal level, as discussed in connection with FIGS. 6, 11. At 314, the available data at the zonal level at this point can be integrated with at least one application. At 316, reservoir decisions can be addressed at the zonal level, such as optimization at the zonal level, conformance control at the zonal level, history matching at the zonal level, changing a parameter at the zonal level, etc.

Those of ordinary skill in the art will appreciate that various embodiments and modifications are envisioned. For example, the input to CRM may be the entire dataset of allowed well connections with all of the 0's and 1's (such as from FIG. 6) or the entire combined dataset of allowed well connections with all of the 0's and 1's (such as from FIG. 11) at the well level. For example, the input to CRM may be the entire dataset of allowed well connections with all of the 0's and 1's (such as from FIG. 6) or the entire combined dataset of allowed well connections with all of the 0's and 1's (such as from FIG. 11) at the zonal level. For example, the input to CRM may be the dataset of allowed well connections with only the 1's (such as from FIG. 6) or the combined dataset of allowed well connections with only the 1's (such as from FIG. 11) at the well level. For example, the input to CRM may be the dataset of allowed well connections with only the 1's (such as from FIG. 6) or the combined dataset of allowed well connections with only the 1's (such as from FIG. 11) at the zonal level. Other modifications will become evident to those of ordinary skill in the art.

Those of ordinary skill in the art will appreciate that the accuracy of CRM can potentially be increased by the allowed well connections that are determined as the well level and/or at the zonal level. For example, the allowed well connection are based on dynamic features (e.g., 4D seismic data), static features, and/or distance for the reservoir, therefore potentially leading to improvements in the analysis of flood operations. Moreover, hidden faults and fractures are more likely to be identified and used in the analysis, multiple field data types suggesting the same are more likely to be identified and used in the analysis (e.g., tracer data and pulse test data supporting the existence of a well connection), conflicting data is more likely to be resolved (e.g., through priorities), etc.

Furthermore, in some embodiments, the analysis of a flood operation can be carried out in a faster or more efficient manner as only allowed well connections with 1's are input to CRM and/or processed further by CRM. In some examples, the analysis of the flood operation may speed up about 200 times or running CRM may decrease from hours, such as about 400 hours, to minutes, such as about 20 minutes.

Furthermore, those of ordinary skill in the art may appreciate that more accurate CRM output may be used to make at least one decision that is likely to improve the flood operation. The decisions may be related to optimization, history matching, conformance control, changing a parameter of the flood operation, or any combination thereof.

Heavy Oil Flood Operation

The hydrocarbon in some hydrocarbon reservoirs is referred to as heavy oil. A flood operation, such as waterflood operation, may be performed on a hydrocarbon reservoir having heavy oil. Disclosed herein are embodiments for using CRM to analyze a flood operation on a hydrocarbon reservoir having heavy oil. As will be discussed herein, various time windows may be generated and CRM may be run for each time window so as to account for mobility, time, or other items characteristics that are specific to hydrocarbon reservoirs having heavy oil. By doing so, CRM output may be more accurate and the analysis of the flood operation may be more accurate.

Figure 14:
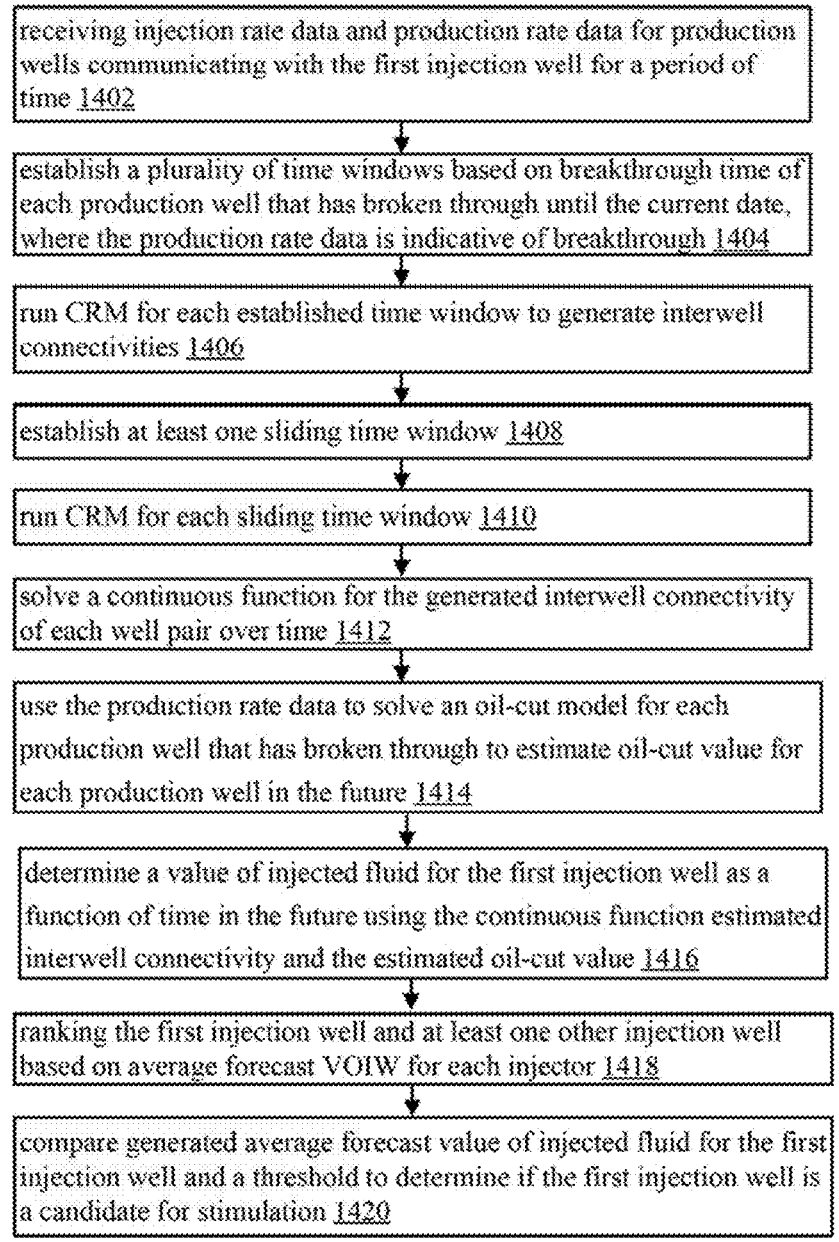
FIG. 14 illustrates an embodiment of a computer implemented method of analyzing a flood operation on a hydrocarbon reservoir having heavy oil.

An embodiment of a computer implemented method of analyzing a flood operation on a hydrocarbon reservoir having heavy oil, referred to as 1400 in FIG. 14. The method 1400 can be executed by a computing system, such as the computing system 200 of FIG. 2A or the CRM application 214 thereof. After executing the method 2000 of FIG. 20, the resulting output may be used as input to update or integrate with the polygon application 216, the zonal application 218, the petrotechnical mapping application 220, the one or more other application 221, the flooding analysis application 212, and/or other item (as in FIGS. 2A, 2C). For ease of understanding, a running example will be used and the running example assumes one injection well and three production wells.

At 1402, the method 1400 receives injection rate data and production rate data for production wells communicating with the first injection well for a period of time. For example, the method receives well names, well locations, injection rates, and production rates. At 1404, the method 1400 establishes a plurality of time windows based on breakthrough time of each production well that has broken through until the current date, wherein the production rate data is indicative of breakthrough. For example, a time window may be established for each producer that has broken through, and optionally, an extra time window. For example, 4 producers that have broken through may lead to establishing 4 or 5 time windows. In some embodiments, 10% watercut may be used as the breakthrough time indicator. In the running example, dates D2 and D3 are at 10% watercut. As such, a first time window from time 0-time 15 is established for the first producer to breakthrough and reach watercut of 10%, a second time window from time 15-time 60 is established for the second producer to breakthrough and reach watercut of 10%, and a third time window from time 60-time 130 is established for all producers to breakthrough and reach watercut of 10%, as illustrated below:

At 1406, CRM may be run for each established time window to generate interwell connectivities. In the running example, for the first time window ending at date D1, the CRM output may include the following interwell connectivities fijs:

|  | CRM-fij for I1-P1 | CRM-fij for Inj1-P2 |
|---|---|---|
| First time window | 0.743155395 | 0.256844605 |

In the running example, for the second time window ending between D1 and D2, the CRM output may include the following interwell connectivities fijs:

|  | CRM-fij for I1-P1 | CRM-fij for Inj1-P2 |
|---|---|---|
| Second time window | 0.784838501 | 0.215161499 |
|  | 0.792383944 | 0.207616056 |

In the running example, for the third time window ending between D3 and D2, the CRM output may include the following interwell connectivities fijs:

|  | data | Time, month | CRM-fij for I1-P1 | CRM-fij for Inj1-P2 | CRM Runs |
|---|---|---|---|---|---|
|  |  | 0 |  |  |  |
|  | 1 | 1 |  |  |  |
|  | 2 | 2 |  |  |  |
| first window at date D1 | 3 | 3 |  |  |  |
|  | 4 | 4 |  |  |  |
|  | 5 | 6 |  |  |  |
|  | 6 | 8 |  |  |  |
|  | 7 | 10 | 0.743155395 | 0.256844605 | Run1 - No Breakthrough |
|  | 8 | 15 |  |  | D1 |
|  | 9 | 25 | 0.784838501 | 0.215161499 | Sliding Window Run - Overlap Time Window |
|  | 10 | 30 |  |  |  |
| second window at date D2 | 11 | 38 | 0.792383944 | 0.207616056 | Run2 - Early stage post breakthrougn of first well - P1 |
|  | 12 | 50 |  |  |  |
|  | 13 | 60 |  |  | D2 -10% watercut first producer |
|  | 14 | 75 |  |  |  |
|  | 15 | 80 |  |  |  |
|  | 16 | 88 | 0.922930965 | 0.077069035 | Sliding Window Run - Overlap Time Window |
|  | 17 | 95 |  |  |  |
|  | 18 | 100 |  |  |  |
| third window at date D3 | 19 | 110 | 0.890533376 | 0.109466624 | Run3 - Early stage after BT of another well - P2 (repeat when another well BT) |
|  | 20 | 120 |  |  |  |
|  | 21 | 130 |  |  | D3 -10% watercut second producer |
|  | 22 | 132 |  |  |  |
|  | 23 | 133 | 0.909424554 | 0.090575446 | Sliding Window Run - Overlap Time Window |
|  | 24 | 142 |  |  |  |
|  | 25 | 149 |  |  |  |
|  | 26 | 150 |  |  |  |
|  | 27 | 153 |  |  |  |
|  | 28 | 161 |  |  |  |
|  | 29 | 166 |  |  |  |
|  | 30 | 172 |  |  |  |
|  | 31 | 181 | 0.899863617 | 0.100136383 | Run4 - After Breakthrough of All Wells until the last data point |
|  | 32 | 182 |  |  |  |
|  | 33 | 191 |  |  | D4 current date |
|  | 34 | 201 |  |  |  |
|  | 35 | 211 |  |  |  |
|  | 36 | 221 |  |  |  |
|  | 37 | 231 |  |  |  |
|  | 38 | 241 |  |  |  |
|  | 39 | 251 |  |  |  |
|  | 40 | 261 |  |  |  |

|  | CRM-fij for I1-P1 | CRM-fij for Inj1-P2 |
| --- | --- | --- |
| Third time window | 0.922930965 | 0.077069035 |
|  | 0.890533376 | 0.109466624 |

Optionally, at 1408-1410, at least one sliding time window may be established and CRM may be run for each sliding time window. The sliding time window may be established to improve the distribution of the interwell connectivity variation between CRM runs 1, 2, 3, and 4. A particular sliding time window may be established between two time windows established at 1404. In the running example, a sliding time window may be established from time 25-time 88, another sliding time window may be established from time 88-time 133, and another sliding time window may be established from time 133-time 191. The following tables indicate the interwell connectivities for the sliding time windows.

|  | CRM-fij for I1-P1 | CRM-fij for Inj1-P2 |
| --- | --- | --- |
| first sliding time window | 0.784838501 | 0.215161499 |
|  | 0.792383944 | 0.207616056 |
|  | 0.922930965 | 0.077069035 |

|  | CRM-fij for I1-P1 | CRM-fij for Inj1-P2 |
| --- | --- | --- |
| Second sliding time window | 0.922930965 | 0.077069035 |
|  | 0.890533376 | 0.109466624 |
|  | 0.909424554 | 0.090575446 |

|  | CRM-fij for I1-P1 | CRM-fij for Inj1-P2 |
| --- | --- | --- |
| third sliding time window | 0.909424554 | 0.090575446 |
|  | 0.899863617 | 0.100136383 |

Figure 15:
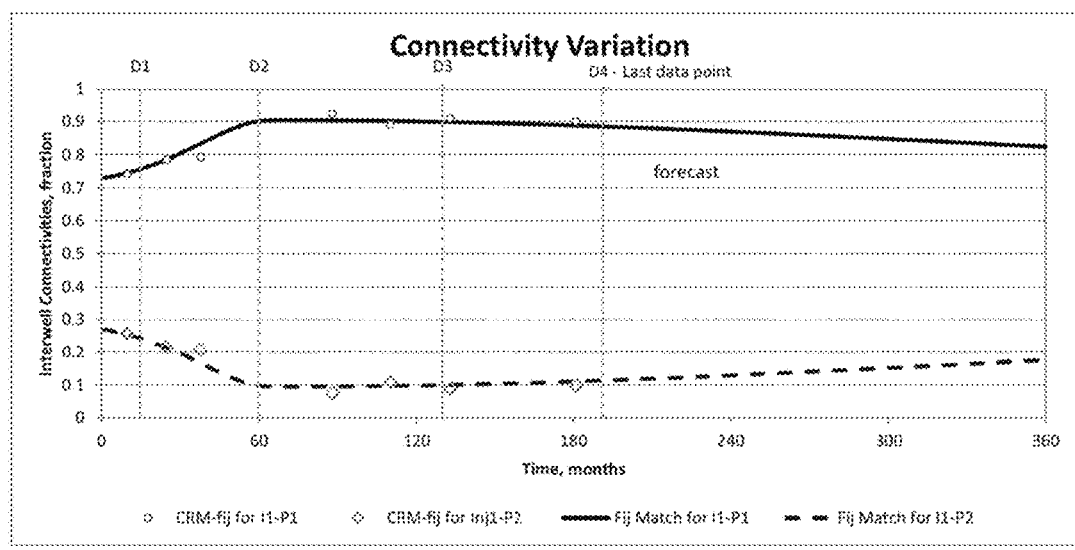
FIGS. 15-17 illustrate examples consistent with the embodiment of FIG. 14.

At 1412, the method 1400 may solve a continuous function for the generated interwell connectivity of each well pair over time using the discrete interwell connectivities obtained in 1406-1410. The continuous function may be a bell shaped, log-normal, betta, logistic curve, or other. In the running example, the interwell connectivity variation plot at FIG. 15 may be generated by plotting the interwell connectivities generated by CRM and then at least one function may be used to fit the interwell connectivity points (e.g., logistic curve) on a curve. The curve and the interwell connectivity points may be displayed to a user in some embodiments, but not in other embodiments.

In the running example, solving the continuous function may include solving the parameters of the function by matching function estimated interwell connectivities to the CRM generated interwell connectivities. Matching the interwell connectivities includes minimizing the error between the function estimated interwell connectivities and the CRM generated interwell connectivities. The parameters and the function estimated fij match values are illustrated below:

| Initial fij Value | Growth Rate (G) | Decline Rate (D) | Integration, N | Peak Time, Years |
| --- | --- | --- | --- | --- |
| 0.7 | 0.05 | 0.005 | 90 | 65 |
| 0.3 | 0.05 | 0.005 | 90 | 65 |

| Time, month | Function estimated fij Match for I1-P1 | Function estimated fij Match for I1-P2 |
| --- | --- | --- |
| 0 | 0.729400211 | 0.270599789 |
| 1 | 0.730789629 | 0.269210371 |
| 2 | 0.732238642 | 0.267761358 |
| 3 | 0.733749198 | 0.266250802 |
| 4 | 0.735323244 | 0.264676756 |
| 6 | 0.738669556 | 0.261330444 |
| 8 | 0.742292858 | 0.257707142 |
| 10 | 0.746207837 | 0.253792163 |
| 15 | 0.757357586 | 0.242642414 |
| 25 | 0.785903843 | 0.214096157 |
| 30 | 0.803196639 | 0.196803361 |
| 38 | 0.833762714 | 0.166237286 |
| 50 | 0.878277722 | 0.121722278 |
| 60 | 0.901382431 | 0.098617569 |
| 75 | 0.904417667 | 0.095582333 |
| 80 | 0.904258082 | 0.095741918 |
| 88 | 0.903870664 | 0.096129336 |
| 95 | 0.903399187 | 0.096600813 |
| 100 | 0.902987362 | 0.097012638 |
| 110 | 0.901978363 | 0.098021637 |
| 120 | 0.900726493 | 0.099273507 |
| 130 | 0.899237858 | 0.100762142 |
| 132 | 0.898912333 | 0.101087667 |
| 133 | 0.898746146 | 0.101253854 |
| 142 | 0.897149159 | 0.102850841 |
| 149 | 0.895783723 | 0.104216277 |
| 150 | 0.895580055 | 0.104419945 |
| 153 | 0.894956349 | 0.105043651 |
| 161 | 0.893201722 | 0.106798278 |
| 166 | 0.892039321 | 0.107960679 |
| 172 | 0.890579879 | 0.109420121 |
| 181 | 0.888263626 | 0.111736374 |
| 182 | 0.887997153 | 0.112002847 |
| 191 | 0.885520243 | 0.114479757 |
| 201 | 0.882609705 | 0.117390295 |
| 211 | 0.879544368 | 0.120455632 |

Figure 16:
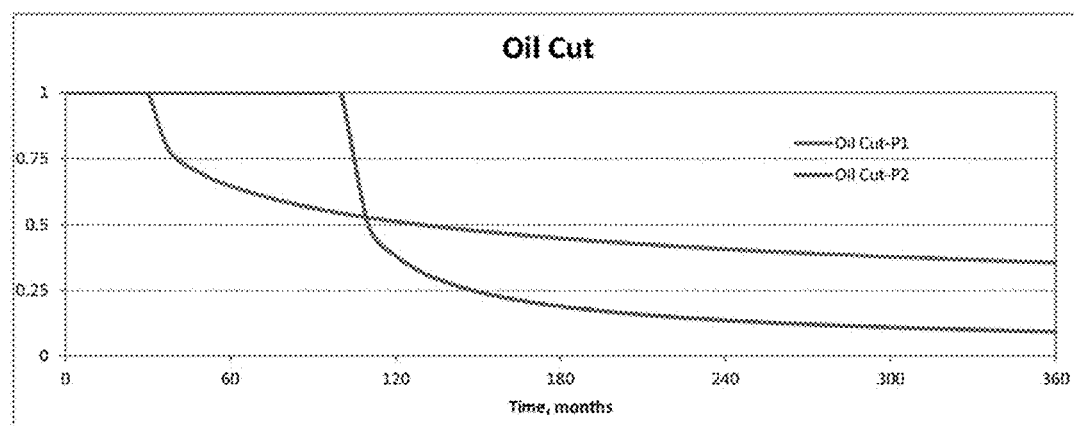

At 1414, the production rate data is used to solve an oil-cut model for each production well that has broken through to estimate oil-cut value for each production well in the future. In the running example, the received production rate data for each producer may be used to solve the parameter of the oil cut model (e.g., power law model). Alpha and beta (below) are the parameters of the oil cut model and a plot of oil cut is illustrated in FIG. 16:

|  | Oil-cut Model | |
| --- | --- | --- |
| breakthrough time | 30 | 100 |
| alpha | 0.1 | 0.2 |
| beta | 0.5 | 0.7 |
| Time, month | Oil Cut-P1 | Oil Cut-P2 |
| 0 |  |  |
| 1 | 1 | 1 |
| 2 | 1 | 1 |
| 3 | 1 | 1 |
| 4 | 1 | 1 |
| 6 | 1 | 1 |
| 8 | 1 | 1 |
| 10 | 1 | 1 |
| 15 | 1 | 1 |
| 25 | 1 | 1 |
| 30 | 1 | 1 |
| 38 | 0.7795188 | 1 |
| 50 | 0.690983 | 1 |
| 60 | 0.6461106 | 1 |
| 75 | 0.5985084 | 1 |
| 80 | 0.5857864 | 1 |

| Oil-cut Model | | |
|---|---|---|
| 88 | 0.5676731 | 1 |
| 95 | 0.5536406 | 1 |
| 100 | 0.5444666 | 1 |
| 110 | 0.527864 | 0.499407 |
| 120 | 0.513167 | 0.380465 |
| 130 | 0.5 | 0.316176 |
| 132 | 0.4975247 | 0.306491 |
| 133 | 0.4963052 | 0.301931 |
| 142 | 0.4858377 | 0.267581 |
| 149 | 0.4782695 | 0.24697 |
| 150 | 0.4772256 | 0.24435 |
| 153 | 0.4741463 | 0.236897 |
| 161 | 0.4662978 | 0.21957 |
| 166 | 0.4616399 | 0.210266 |
| 172 | 0.4562798 | 0.200331 |
| 181 | 0.4486678 | 0.187448 |
| 182 | 0.4478515 | 0.186144 |
| 191 | 0.4407504 | 0.175352 |
| 201 | 0.4333376 | 0.165047 |
| 211 | 0.4263733 | 0.15614 |

At 1416, the value of injected fluid as a function of time in future may be determined for each injector using the continuous function estimated interwell connectivity 1412 and the estimated oil-cut value of 1414. In the running example, VOIF(t) is calculated for the current timestep D4 and the timesteps in the forecast time window (1 or 2 or 3 years after the current date D4) and get an average VOIF. The following equation may be calculated to VOIF(t) for each injector:

$$VOIF(t) = \sum_{j}^{N} f_{ij}(t) f_{oj}(t)$$

Figure 17:
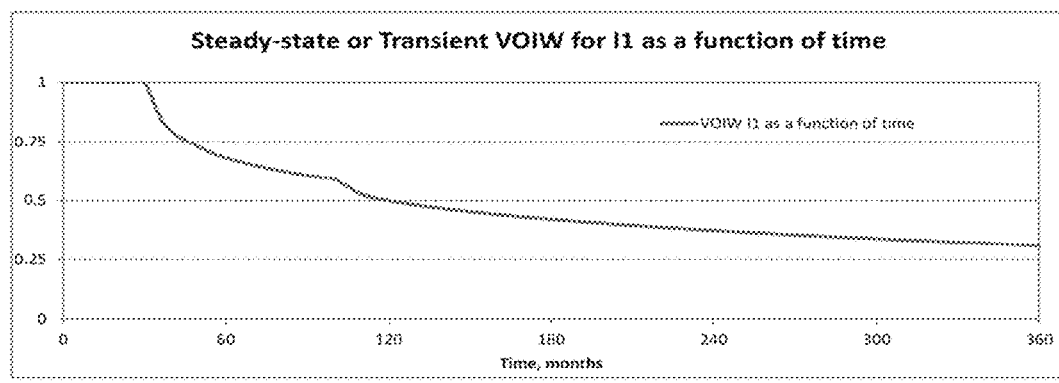

In the equation, $f_{oj}(t)$ is oil cut as a function of time and $f_{ij}(t)$ is interwell connectivity as a function of time. The (t) in the equation, such as in VOIF(t), is a function of time. In some embodiments, the $f_{ij}(t)$ may be at a steady state as discussed herein. Alternatively, if transient is desired, then fij(t) may be replaced with f*ij(t) in the equation. In the running example, 0.39 is the average forecast VOIF after current time D4 for I1, as illustrated below and at FIG. 17:

| Average forecast VOIF post D4 for I1 |
|---|
| 0.39 |

| Time, month | VOIF I1 as a function of time |
|---|---|
| 0 | |
| 1 | 1 |
| 2 | 1 |
| 3 | 1 |
| 4 | 1 |
| 6 | 1 |
| 8 | 1 |
| 10 | 1 |
| 15 | 1 |
| 25 | 1 |
| 30 | 1 |
| 38 | 0.816 |
| 50 | 0.729 |
| 60 | 0.681 |
| 75 | 0.637 |

| Time, month | VOIF I1 as a function of time | |
|---|---|---|
| 80 | 0.625 | |
| 88 | 0.609 | |
| 95 | 0.597 | |
| 100 | 0.589 | |
| 110 | 0.525 | |
| 120 | 0.500 | |
| 130 | 0.481 | |
| 132 | 0.478 | |
| 133 | 0.477 | |
| 142 | 0.463 | |
| 149 | 0.454 | |
| 150 | 0.453 | |
| 153 | 0.449 | |
| 161 | 0.440 | |
| 166 | 0.435 | |
| 172 | 0.428 | |
| 181 | 0.419 | |
| 182 | 0.419 | |
| 191 | 0.410 | D4: current date |
| 201 | 0.402 | |
| 211 | 0.394 | |
| 221 | 0.386 | |
| 231 | 0.379 | |
| 241 | 0.372 | |

At 1418, a plurality of injectors may be ranked based on average forecast VOIF (accounts for time) values for each injector for the forecasted time window, such as from current time to a defined period of timein. In the running example, there is only 1 injector, and it has as an average forecast VOIF of 0.39. However, this injector could be ranked against another injector.

At 1420, the generated average forecast value of injected fluid for the first injection well is compared with a threshold to determine if the first injection well is a candidate for stimulation. For example, a low average forecast VOIF may indicate that the corresponding injector is a candidate for stimulation (e.g., stimulation with an acid agent).

Those of ordinary skill in the art will appreciate that various modifications may be made to the embodiments disclosed herein. For example, all producers had broken through in the running example, but such need not be the case. For example, if only a portion of the producers had broken through, then oil cut can equal 1 for injectors with corresponding producers that have not broken through. Also, the number of time windows may be based on producers broken through, so the fewer producers broken through then the fewer time windows may be established.

Those of ordinary skill may appreciate the illustrate embodiments may lead to more accurate analysis of flood operations of reservoirs having heavy oil Furthermore, the method 1400 may also be able to recommend an injection rate for each injector based on the ranking per average forecast VOIF and operation limits. The method 1400 may output (e.g., display, print, etc.) the injection rate recommendation and a user may then physically make the appropriate adjustments to achieve the recommend injection rate for a particular injector. Adjusting the injection rate based on the ranking per average forecast VOIF from and operational limits of injectors and producers may improve hydrocarbon recovery.

Conformance Control

A flood operation sometimes leads to non-uniform volumetric sweep or a deviation from uniform volumetric sweep in a reservoir because of the reservoir heterogeneity, unfavorable mobility ratio, gravity segregation, gas override, well placement, perforations, completions, casing, etc. Such a scenario is known as a conformance problem and hydrocarbon production may increase by conformance control. Based on input data, different tools may be used as shown in the table below:

| Data/Evaluation | EV Estimates | Koval | CRM | CRM Zonal | Numerical Simulation | Tracer | Modified Hall Plot | Well Profiles (static and dynamic logs) |
|---|---|---|---|---|---|---|---|---|
| Model calibration | x | x | x | x | x | x | | |
| Logs, Core data & tests | x | x | | | x | | | x |
| Injection/Production data | x | x | x | x | x | x | x | |
| Water chemistry | | | | | x | x | | |
| Oil/gas chemistry | | | | | x | x | | |
| Injection profiles | | | | x | x | | | x |
| Production profiles | | | | x | x | | | x |
| Reservoir pressures | | | x | x | x | | x | |
| Flowing BHPs | | | x | x | x | | | x |
| Tracer data | | | x | x | x | x | | |
| Saturation logs | | | | x | x | | | |
| Seismic data | | | x | x | x | | | |
| Flow-Storage Capacity | | x | x | x | x | x | | x |

To screen for conformance issues where an injecting entity (an injection entity can be a field, a reservoir field, reservoir, well or zone) causes early and excessive displacing fluid production at a producing entity (a producing entity can be a field, a reservoir, a well, or a zone) and reduces hydrocarbon recovery, analytical tools such as CRM, modified Koval method (MKM), modified Hall Plot, tracer and flow-storage capacity plotsand, etc. may be used. To identify and rank conformance candidates at the level of any injecting and producing entity (e.g., a field, a reservoir, a well, or a zone), a conformance problem index (CPI) is introduced herein.

| Method | Koval | CRM | Numerical Simulation | Tracer | Modified Hall Plot | Well Profiles (static and dynamic logs) |
|---|---|---|---|---|---|---|
| Applied to Field/Reservoir Level Screening | X | X | X | | | |
| Applied to Injection Entity Screening | | X | X | X | X | |
| Applied to Production Entity Screening | X | | X | X | | |
| Applied to Injection Entity—Zonal Level | | X | X | X | | X |
| Applied to Production Entity—Zonal Level | X | | X | X | | X |
| Applied Injection-Production Entity Pair Level Screening | | X | X | X | | |

An embodiment of a computer implemented method of identifying at least one conformance candidate (e.g., using the CPI and components thereof) is provided herein, referred to the method 1800 (numbers 1802-1820) in FIG. 18. The method 1800 may correspond to the diagnostic & screening portion of the conformance control workflow of FIG. 13. The method 1800 can be executed by a computing system, such as the computing system 200 of FIG. 2A. After executing the method 2000 of FIG. 20, the resulting output may be used as input to update or integrate with the CRM application 214, polygon application 216, the zonal application 218, the petrotechnical mapping application 220, the one or more other application 221, the flooding analysis application 212, and/or other item (e.g., as illustrated in FIGS. 2A, 2C).

Defining Conformance Problem Index (CPI): As disclosed herein, a CPI is evaluated at the level of injecting and producing entities by defining and evaluating its three main components, which are Injection Entity Index (IEI), Production Entity Index (PEI) and Operational Index (OI), as illustrated below:

$$CPI = IEI * PEI * OI$$

The CPI value ranges between 0 and 1, the higher the CPI value the higher the degree of conformance issue in the entity (e.g., producing/injecting entities). Two running examples will be presented to illustrate use of the CPI at a field/reservoir level and at a well/zone level.

Defining Injection Entity Index: An IEI is defined by combining (i) injection efficiency and (ii)) Value of Injected Fluid (VIOF) obtained between at least one injecting entity and one producing entity pair (e.g., an injecting-producing entity pair could be at reservoir-reservoir level, injector-producer level, or injector-producer at zonal level) and (iii) pore volume injected (PVI) for each injecting entity. This calculation can be obtained based on analytical methods such as capacitance-resistance model (CRM), tracer analysis, or any combination thereof. In some embodiments, fij, may also be used. Nonetheless, an IEI ranges between 0 and 1, and may be solved according to the equation below:

$$IEI = (1 - f_{ij}) * VOIF_{ij} / PVI_i$$

Defining Producing Entity Index (PEI): A PEI is defined by evaluating an estimate (or a proxy of fraction) of remaining moveable oil in place at one pore volume injected for at least one producing entity. This calculation can be obtained based on analytical methods such as modified Koval method (MKM), tracer analysis, or any combination thereof. A recovery factor estimate, RF@1PVI is used in calculating PEI. A PEI ranges between 0 and 1, and may be solved according to the equation below:

PEI=1-RF@1PVI

Defining the Operational Index (OI): An OI is a value of either one or zero which represents operation status (e.g., the availability of a given producing or injecting entity) for any conformance treatment.

Application when injection and production entities are field/reservoir—the field/reservoir level injection efficiency for an example of four field/reservoir is shown below:

| CRM or Tracer Output 1 | | | | | |
|---|---|---|---|---|---|
| Injection Efficiency between Injection and | | Injection Entities (Field or Reservoir) | | | |
| Production Entities | | IE 01 | IE 02 | IE 03 | IE 04 |
| Production Entities (Field or Reservoir) | PE 01 | 0.75 | | | |
| | PE 02 | | 0.40 | | |
| | PE 03 | | | 0.92 | |
| | PE 04 | | | | 0.60 |
| Sum | | 0.75 | 0.4 | 0.92 | 0.6 |

Application when injection and production entities are field/reservoir—the field/reservoir level value of injected fluid (VOIF) for an example of four field/reservoir is shown below:

| CRM Output 2 | | | | | |
|---|---|---|---|---|---|
| Value of | | Injection Entities (Field or Reservoir) | | | |
| Injected Fluid | | IE 01 | IE 02 | IE 03 | IE 04 |
| Production Entities (Field or Reservoir) | PE 01 | 0.82 | | | |
| | PE 02 | | 0.43 | | |
| | PE 03 | | | 0.05 | |
| | PE 04 | | | | 0.30 |
| Sum | | 0.82 | 0.43 | 0.05 | 0.3 |

Application when injection and production entities are field/reservoir—the field/reservoir level pore volumes injected (PVI) for an example of four field/reservoir is shown below:

| | Injection Entities (Field or Reservoir) | | | |
|---|---|---|---|---|
| | IE 01 | IE 02 | IE 03 | IE 04 |
| Pore Volume Injected in Analysis Period | 1.2 | 0.7 | 2.1 | 1.8 |

Application when injection and production entities are field/reservoir—the field/reservoir level Injection Entity Index (IEI) for an example of four field/reservoir is calculated from IEI equation above and is shown below, in this example IEI is highest for field/reservoir 3:

| Injection Entity | | Injection Entities (Field or Reservoir) | | | |
|---|---|---|---|---|---|
| Index (IEI) | | IE 01 | IE 02 | IE 03 | IE 04 |
| Production Entities | PE 01 | 0.11 | | | |
| | PE 02 | | 0.33 | | |
| | PE 03 | | | 0.42 | |
| | PE 04 | | | | 0.23 |

Application when injection and production entities are field/reservoir—the field/reservoir level Production Entity Index (PEI) for an example of four field/reservoir is calculated from the estimates of recovery factors at one pore volume injected are shown below in this example the PEI is highest for field/reservoir 3:

| Modified Koval Method Output 1 | | | |
|---|---|---|---|
| | | Recovery Factor based on movable oil at 1 Pore Volume Injected | Production Entity Index (PEI) |
| Production Entities (Well or Zone) | PE 01 | 0.40 | 0.60 |
| | PE 02 | 0.32 | 0.68 |
| | PE 03 | 0.15 | 0.85 |
| | PE 04 | 0.20 | 0.80 |

Application when injection and production entities are field/reservoir—the field/reservoir level Operational Index (OI) for an example of four field/reservoir is shown below, in this example the OI is one for all field/reservoir indicating availability of all candidates for conformance treatment:

| Operational Condition/Stability | | | | | |
|---|---|---|---|---|---|
| Operational | | Injection Entities (Field or Reservoir) | | | |
| Index (OI) | | IE 01 | IE 02 | IE 03 | IE 04 |
| Production Entities (Field or Reservoir) | PE 01 | 1 | | | |
| | PE 02 | | 1 | | |
| | PE 03 | | | 1 | |
| | PE 04 | | | | 1 |

Application when injection and production entities are field/reservoir—the field/reservoir level Conformance Problem Index (CPI) for an example of four field/reservoir is calculated from CPI equation above and is shown below, in this example the CPI is highest for field/reservoir 3 indicating the field/reservoir with highest degree of conformance issue:

| Conformance | | Injection Entities (field) | | | |
|---|---|---|---|---|---|
| Problem Index | | IE 01 | IE 02 | IE 03 | IE 04 |
| Production Entities (Field or Reservoir) | PE 01 | 0.07 | | | |
| | PE 02 | | 0.22 | | |
| | PE 03 | | | 0.35 | |
| | PE 04 | | | | 0.19 |

Application when injection and production entities are well/zone—the well/zone level injection efficiency for an example of four well/zone is shown below:

| CRM Output 1 | | | | | |
|---|---|---|---|---|---|
| Injection Efficiency between Injection and | | Injection Entities (Well or Zone) | | | |
| Production Entities | | IE 01 | IE 02 | IE 03 | IE 04 |
| Production Entities (Well or Zone) | PE 01 | 0.96 | 0.47 | 0.10 | 0.18 |
| | PE 02 | 0.01 | 0.02 | 0.02 | 0.15 |
| | PE 03 | 0.00 | 0.19 | 0.02 | 0.00 |
| | PE 04 | 0.03 | 0.32 | 0.86 | 0.67 |
| | Sum | 1 | 1 | 1 | 1 |

Application when injection and production entities are well/zone—the well/zone level value of injected fluid (VOIF) for an example of four well/zone is shown below:

| CRM Output 2 | | | | | |
|---|---|---|---|---|---|
| Value of Injected Fluid | | Injection Entities (Well or Zone) | | | |
| | | IE 01 | IE 02 | IE 03 | IE 04 |
| Production Entities (Well or Zone) | PE 01 | 0.30 | 0.15 | 0.03 | 0.06 |
| | PE 02 | 0.00 | 0.01 | 0.01 | 0.06 |
| | PE 03 | 0.00 | 0.03 | 0.00 | 0.00 |
| | PE 04 | 0.01 | 0.06 | 0.15 | 0.12 |
| | Sum | 0.31 | 0.24 | 0.19 | 0.23 |

Application when injection and production entities are well/zone—the well/zone level pore volumes injected (PVI) for an example of four well/zone is shown below:

| | Injection Entities (Well or Zone) | | | |
|---|---|---|---|---|
| | IE 01 | IE 02 | IE 03 | IE 04 |
| Pore Volume Injected in Analysis Period | 1.00 | 2.00 | 1.20 | 2.10 |

Application when injection and production entities are well/zone—the well/zone level Injection Entity Index (IEI) for an example of four well/zone is calculated from IEI equation above and is shown below, in this example IEI is highest for well/zone IE01:

| Injection Entity Index (IEI) | | Injection Entities (Well or Zone) | | | |
|---|---|---|---|---|---|
| | | IE 01 | IE 02 | IE 03 | IE 04 |
| Production Entities (Well or Zone) | PE 01 | 0.67 | 0.20 | 0.08 | 0.08 |
| | PE 02 | 0.01 | 0.01 | 0.02 | 0.07 |
| | PE 03 | 0.00 | 0.09 | 0.02 | 0.00 |
| | PE 04 | 0.03 | 0.15 | 0.61 | 0.28 |

Application when injection and production entities are well/zone—the well/zone level Production Entity Index (PEI) for an example of four well/zone is calculated from the estimates of recovery factors at one pore volume injected are shown below in this example the PEI is highest for well/zone PE01:

| Modified Koval Method Output 1 | | | |
|---|---|---|---|
| | | Recovery Factor based on movable oil at 1 Pore Volume Injected | Production Entity Index (PEI) |
| Production Entities (Well or Zone) | PE 01 | 0.20 | 0.80 |
| | PE 02 | 0.40 | 0.60 |
| | PE 03 | 0.56 | 0.44 |
| | PE 04 | 0.37 | 0.63 |

Application when injection and production entities are well/zone—the well/zone level Operational Index (OI) for an example of four well/zone is shown below, in this example the OI is one for all well/zone indicating availability of all candidates for conformance treatment:

| Operational Condition/Stability | | | | | |
|---|---|---|---|---|---|
| Operational Index (OI) | | Injection Entities (Well or Zone) | | | |
| | | IE 01 | IE 02 | IE 03 | IE 04 |
| Production Entities (Well or Zone) | PE 01 | 1 | 1 | 1 | 1 |
| | PE 02 | 1 | 1 | 1 | 1 |
| | PE 03 | 1 | 1 | 1 | 1 |
| | PE 04 | 1 | 1 | 1 | 1 |

Application when injection and production entities are well/zone—the well/zone level Conformance Problem Index (CPI) for an example of four well/zone is calculated from CPI equation above and is shown below, in this example the CPI is highest for well/zone 3 indicating the well/zone with highest degree of conformance issue:

| Conformance Problem Index | | Injection Entities (Well) | | | |
|---|---|---|---|---|---|
| | | IE 01 | IE 02 | IE 03 | IE 04 |
| Production Entities (Well or Zone) | PE 01 | 0.53 | 0.16 | 0.06 | 0.06 |
| | PE 02 | 0.01 | 0.00 | 0.01 | 0.04 |
| | PE 03 | 0.00 | 0.04 | 0.01 | 0.00 |
| | PE 04 | 0.02 | 0.09 | 0.38 | 0.18 |

Figure 19A:
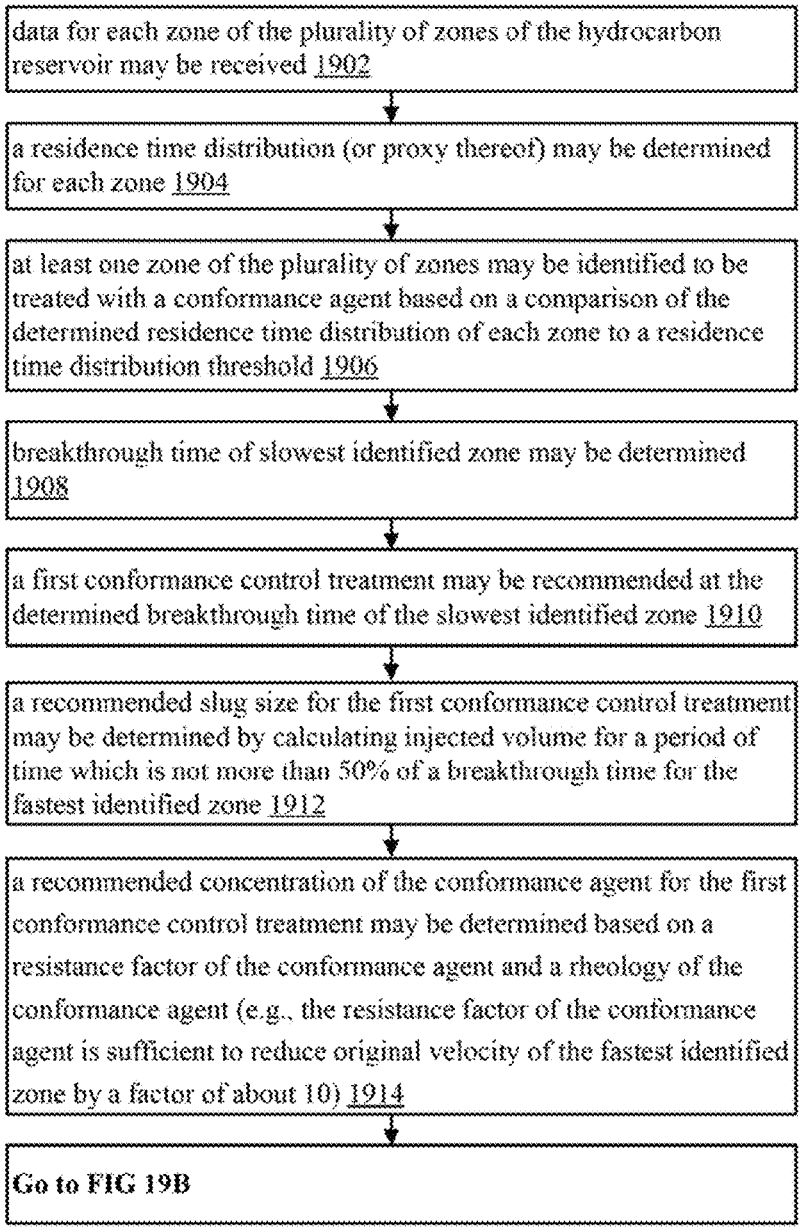
FIGS. 19A-19B illustrates one embodiment of a computer implemented method of determining a conformance control treatment for a well of a hydrocarbon reservoir, where the well is in fluidic communication with a plurality of zones of the hydrocarbon reservoir.
Figure 19B:
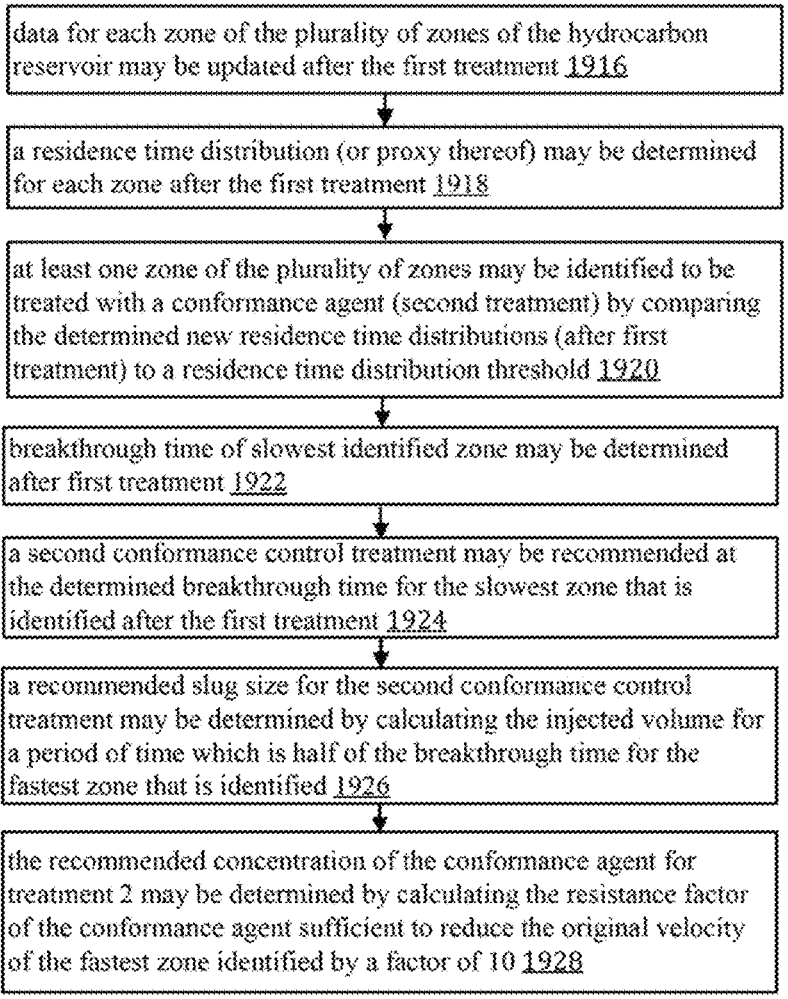

After an entity (e.g., a well) is identified as a conformance candidate, a conformance control treatment may be determined FIGS. 19A-19B illustrates one embodiment of a computer implemented method of determining a conformance control treatment for a well of a hydrocarbon reservoir, where the well is in fluidic communication with a plurality of zones of the hydrocarbon reservoir, referred to herein as method 1900. The method 1900 may correspond to modeling optimum slug design/placement portion of the conformance control workflow of FIG. 13. The method 1900 can be executed by a computing system, such as the computing system 200 of FIG. 2A. After executing the method 1900 of FIG. 20, the resulting output may be used as input to update or integrate with the CRM application 214, polygon application 216, the zonal application 218, the petrotechnical mapping application 220, the one or more other application 221, the flooding analysis application 212, and/or other item (e.g., as illustrated in FIG.). The method 1900 may be used to determine which zone or zones should be treated with a conformance agent, determine slug size, determine concentration of the conformance agent, and/or determine when to perform the conformance control treatment. The well may be identified as discussed herein in connection with FIG. 18 or using some other process. A running example will be discussed that assumes a hydrocarbon reservoir with at least one injection well and five zones. The running example also assumes an injection rate of 2500 bbls/day, a pore volume of 100,000 bbls, and a threshold for residence time distribution of 10 days.

At 1902, data for each zone of the plurality of zones of the hydrocarbon reservoir may be received. The data includes depth, porosity, permeability, and pore volume for each of the zones. In the running example, the following data is received for the zones.

| | Input Data | | | |
|---|---|---|---|---|
| Reservoir Zones | Depth (ft) | Porosity Fraction | Permeability (md) | Pore volume Bbls |
| | 485 | 0 | 0 | |
| 1 | 500 | 0.3 | 100 | 26,316 | 0.01 |
| 2 | 503 | 0.3 | 1000 | 5,263 | 0.1 |
| 3 | 535 | 0.3 | 10 | 56,140 | 0.001 |
| 4 | 540 | 0.3 | 500 | 8,772 | 0.05 |
| 5 | 542 | 0.3 | 5000 | 3,509 | 0.5 |

At 1904, a residence time distribution (or proxy thereof) may be determined for each zone. The residence time distribution may be determined using CRM zonal, F–C Plot, tracers, etc. The F–C Plot or flow capacity-Storage capacity is a static plot where both flow and storage capacity information are obtained from static log data, permeability, porosity, and thickness. In some embodiments, the F+C plot may be used. The F+C plot is a semi-dynamic plot—constructed similar to an F–C plot, but the flow information is from profile data and the storage capacity information is from porosity logs. In some embodiments, the F-Phi plot may be used. The F-Phi plot is a dynamic plot and both flow and storage information are from dynamic production data. Indeed, in some embodiments, determining the residence time distribution for each zone of the plurality of zones includes using tracer data, CRM zonal, a F–C plot, F+C plot, F-Phi plot, log data, ILT data, CRM generated PLT, slope data, or any combination thereof. In the running example, the following residence time distributions are determined for the zones.

| Original residence time distribution before treatment 1 | | |
|---|---|---|
| Reservoir Zones | Residence time distribution using CRM Zonal, F-C, Tracers, etc. tD, Dimensionless | Residence time distribution using CRM Zonal, F-C, Tracers, etc. t, days |
| 5 | 0.06 | 2 |
| 2 | 0.30 | 12 |
| 4 | 0.61 | 24 |
| 1 | 3.04 | 122 |
| 3 | 30.39 | 1215 |

At 1906, at least one zone of the plurality of zones may be identified to be treated with a conformance agent based on a comparison of the determined residence time distribution of each zone to a residence time distribution threshold. In the running example, the threshold for residence time distribution is 10 days and any zone with residence time distribution of less than or equal to the threshold may be identified for conformance control, which would likely shut off that zone. The threshold may be received from a user or automatically generated. In the running example, zone 2 has a residence time distribution of 2 days, which is lower than the threshold of 10 days, thus, zone 2 is identified for treatment with a conformance agent (treatment 1). A residence time distribution of 2 days indicates that the displacing fluid, such as water or brine from a waterflood operation, breaks through in about 2 days which is before the threshold of 10 days.

At 1908, breakthrough time of slowest identified zone may be determined. The breakthrough time may be determined from the residence time distributions determined at 1904 for the corresponding identified zones. In the running example, only zone2 was identified and the residence time distribution is 2 days for zone 2 so the breakthrough time is determined to be 2 days. If another zone had been identified, then the slowest residence time distribution from the identified may be selected, which will be described further in connection with treatment2.

At 1910, a first conformance control treatment may be recommended at the determined breakthrough time of the slowest identified zone. In the running example, a first conformance control treatment (treatment1) may be recommended at 2 days for zone 2, as illustrated below.

| | Treatment 1 |
|---|---|
| Time of conformance treatment is equal to breakthrough of the slowest of the zones to be shut off (days) | 2 days |
| Slug Size (bbls) is half of the injected volume before breakthrough of the fastest zones | 3039 bbls |
| Resistance factor to be used to reduce its velocity to 1/10th of its original velocity | 17 |
| Concentration of the conformance agent to be used based on the rheology | 20776 ppm |
| Sweep Efficiency before treatment @ 1 PV injected | 0.25 |
| Sweep efficiency after treatment 1 @ 1 PV injected | 0.5 |

At 1912, a recommend slug size for the first conformance control treatment may be determined. The slug size is determined by calculating injected volume for a period of time which is not more than 50% of a breakthrough time for the fastest identified zone. In the running example, a first conformance treatment slug size (treatment 1) is recommended to be 3039 Bbls.

At 1914, a recommended concentration of the conformance agent for treatment 1 may be determined by calculating a resistance factor of the conformance agent sufficient to reduce the original velocity of the fastest identified zone by a factor of about 10. The conformance agent rheology may be used to determine the concentration after the resistance factor is calculated. In the running example, the resistance factor for the first conformance agent (treatment 1) is recommended to be 17. From the rheology for the conformance agent, the recommended conformance agent concentration is determined to be 20776 ppm so that a resistance factor of 17 is achieved.

At 1916, data for each zone of the plurality of zones of the hydrocarbon reservoir may be updated after treatment 1. At least one of porosity, permeability, pore volume, or any combination thereof for each of the plurality of zones of the hydrocarbon reservoir may be updated after treatment 1. In the running example, the following data is updated for the zones.

| | Input Data | | | |
|---|---|---|---|---|
| Reservoir Zones | Depth (ft) | Porosity Fraction | Permeability (md) | Pore volume Bbls |
| | 485 | 0 | 0 | |
| 1 | 500 | 0.3 | 86 | 26,316 | 0.08 |
| 2 | 503 | 0.3 | 385 | 5,263 | 0.35 |

-continued

| | | Input Data | | | |
|---|---|---|---|---|---|
| Reservoir Zones | Depth (ft) | Porosity Fraction | Permeability (md) | Pore volume Bbls | |
| 3 | 535 | 0.3 | 10 | 56,140 | 0.01 |
| 4 | 540 | 0.3 | 278 | 8,772 | 0.25 |
| 5 | 542 | 0.3 | 556 | 3,509 | 0.50 |

At 1918, a residence time distribution (or proxy thereof) may be determined for each zone after the first treatment. The new residence time distribution may be determined using updated CRM zonal, F–C Plot, tracers, Modified Koval Method, etc. The F–C Plot or flow capacity-Storage capacity is a static plot where both flow and storage capacity information are obtained from static log data, permeability, porosity, and thickness. In some embodiments, the F+C plot may be used. The F+C plot is a semi-dynamic plot—constructed similar to an F–C plot, but the flow information is from profile data and the storage capacity information is from porosity logs. In some embodiments, the F-Phi plot may be used. The F-Phi plot is a dynamic plot and both flow and storage information are from dynamic production data, for example, tracers or Modified Koval Method. Indeed, in some embodiments, determining the new residence time distribution for each zone of the plurality of zones includes using updated tracer data, CRM zonal, Modified Koval Method, an F–C plot, F+C plot, F-Phi plot, log data, ILT data, CRM generated PLT, or any combination thereof. In the running example, the following new residence time distributions are determined for the zones after the first treatment.

| | Original residence time distribution after treatment 1 or before treatment 2 | |
|---|---|---|
| Reservoir Zones | Residence time distribution using CRM Zonal, F-C, Tracers, etc. tD, Dimensionless | Residence time distribution using CRM Zonal, F-C, Tracers or Modified Koval Method etc. t, days |
| 5 | 0.17 | 7 |
| 2 | 0.24 | 10 |
| 4 | 0.33 | 13 |
| 1 | 1.07 | 43 |
| 3 | 9.38 | 375 |

At 1920, at least one zone of the plurality of zones may be identified to be treated with a conformance agent (second treatment) by comparing the determined new residence time distributions (after first treatment) to a residence time distribution threshold. In the running example, the threshold for residence time distribution for treatment 2 is still 10 days and any zone with residence time distribution of less than or equal to the threshold may be identified for conformance control for second treatment, which would likely shut off that zone. The threshold may be received from a user or automatically generated. The threshold for this second conformance control treatment analysis may be the same or different than the threshold used for the first conformance control treatment analysis. In the running example, zones 5 and 2 have residence times of 7 and 10 days, respectively, after the first treatment which is lower than or equal to the threshold of 10 days. Thus, zones 5 and 2 are identified for treatment with a conformance agent (treatment 2). A residence time of 7 and 10 days indicates that the displacing fluid, such as water or brine from a waterflood operation, breaks through in about 10 days in the slowest of the identified layers (zone 2) which is equal to the threshold of 10 days.

At 1922, breakthrough time of slowest identified zone may be determined after first treatment. The breakthrough time may be determined from the residence time distributions determined at 1918 for the corresponding identified zones after treatment 1. In the running example, zones 5 and 2 were identified and the residence time distribution is 7 days for zone 5 and 10 days for zone 2 so the breakthrough time of slowest identified zone is determined to be 10 days.

At 1924, a second conformance control treatment may be recommended at the determined breakthrough time for the slowest zone that is identified after the first treatment. In the running example, a second conformance control treatment (treatment 2) may be recommended at 10 days for zones 5 and 2 after the first conformance treatment, as illustrated below.

| Treatment 2 | |
|---|---|
| Time of conformance treatment is equal to breakthrough of the slowest of the zones to be shut off (days) | 10 days |
| Slug Size (bbls) is half of the injected volume before breakthrough of the fastest zone | 8308 bbls |
| Resistance factor to be used to reduce its velocity to 1/10th of its original velocity | 17 |
| Concentration of the conformance agent to be used based on the rheology | 20776 ppm |
| Sweep efficiency after treatment 2 @ 1 PV injected | 0.6 |

At 1926, a recommended slug size for the second conformance control treatment may be determined. The slug size for the second conformance control treatment is determined by calculating injected volume for a period of time which is not more than 50% of an updated breakthrough time for the fastest identified zone. In the running example, the fastest of the zones identified is zone 5 and a second conformance treatment slug size (treatment 2) is recommended to be 8308 Bbls.

At 1928, a recommended concentration of the conformance agent for treatment 2 may be determined. The concentration of the conformance agent for the second conformance control treatment is based on a resistance factor of the conformance agent for the second conformance control treatment and a rheology of the conformance agent for the second conformance control treatment. The resistance factor of the conformance agent of the second conformance control treatment is sufficient to reduce updated velocity of the fastest identified zone after the first conformance control treatment by a factor of about 10. The conformance agent rheology may be used to determine the concentration after the sufficient resistance factor is calculated. In the running example, the resistance factor for the second conformance agent (treatment 2) is recommended to be 17. From the rheology for the conformance agent, the recommended conformance agent concentration is determined to be 20776 ppm so that a resistance factor of 17 is achieved.

Those of ordinary skill in the art may appreciate that these embodiments may lead to an increase in accuracy and an increase in repeatability in the area of conformance control. For example, a user may be given a recommendation as to the zone, slug size, concentration, and/or time period for the conformance control treatment, and therefore, decisions may be based on data and not ad-hoc.

Comparing Different Flood Operations

Different flood operations are oftentimes performed on a hydrocarbon reservoir. For example, a flood operation with polymer, also referred to as polymer flooding, is an enhanced oil recovery technique. In a polymer flooding operation, certain polymers and/or surfactants may be dissolved in the displacing fluid (e.g., prior to injecting the injection fluid) to decrease the displacing fluid's mobility and increase the displacing fluid's viscosity. By doing so, the displacing fluid flows through the hydrocarbon reservoir in a slower manner in a polymer flood operation and increases the likelihood that a larger volume of the hydrocarbon reservoir will be contacted as compared to a waterflood operation. Analysis of multiple flood operations may be useful in evaluating project feasibility and for other purposes.

Figure 20:
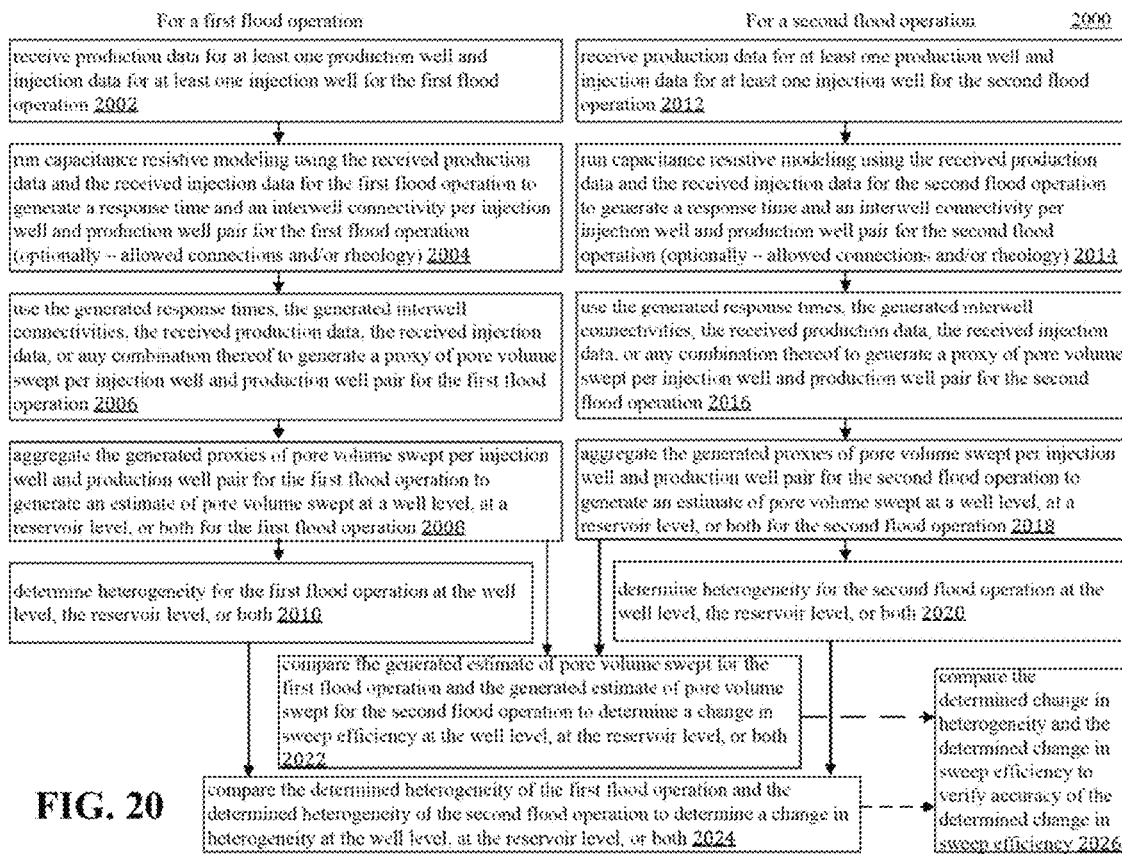
FIG. 20 illustrates one embodiment of a computer implemented method of analyzing at least a first flood operation and a second flood operation on a hydrocarbon reservoir having at least one production well and at least one injection well.

FIG. 20 illustrates one embodiment of a computer implemented method of analyzing at least a first flood operation and a second flood operation on a hydrocarbon reservoir having at least one production well and at least one injection well, referred to herein as method 2000. The method 200 can be executed by a computing system, such as the computing system 200 of FIG. 2A or the CRM application 214 thereof. After executing the method 2000 of FIG. 20, the resulting change in sweep efficiency between the first flood operation (e.g., a waterflood operation) and the second flood operation (e.g., a polymer flood operation) may be used as input to update or integrate with the polygon application 216, the zonal application 218, the petrotechnical mapping application 220, the one or more other application 221, the flooding analysis application 212, and/or other item (e.g., as illustrated in FIGS. 2A, 2C). The change in sweep efficiency between the first flood operation (e.g., the waterflood operation) and the second flood operation (e.g., the polymer flood operation) may also be used to make physical adjustments, such as physical adjustments to the polymer flood operation like changing the polymer concentration, changing the injection rate, and other physical adjustments.

Starting with the first flood operation, at 2002, production data may be received for at least one production well and injection data for at least one injection well for the first flood operation. A running example will be discussed that assumes a hydrocarbon reservoir with a first injection well $I_1$ and six production wells $P_1$, $P_2$, $P_3$, $P_4$, $P_5$, $P_6$, a first flood operation (e.g., a waterflood operation) was performed on the hydrocarbon reservoir between years 1980-1990, and a second flood operation (e.g., a polymer flood operation) was performed on the hydrocarbon reservoir between years 1990-1995. Production data such as production rate data may be received for the six production wells $P_1$, $P_2$, $P_3$, $P_4$, $P_5$, $P_6$ from the first flood operation, for example, production rate data for the entire or a portion of the first flood operation. Injection data such as injection rate data may be received for the first injection well $I_1$ from the first flood operation, for example, injection rate data for the entire or a portion of the first flood operation. The production data may include production rate and flowing pressure data as a function of time for production wells, and the injection data may include injection rate and flowing pressure data as a function of time for injection wells.

At 2004, CRM may be run using the received production data and the received injection data for the first flood operation to generate a response time and an interwell connectivity per injection well and production well pair for the first flood operation. For example, the response time injection well and production well pair may be generated by CRM using the following equation:

$$\tau_{ij} = \frac{c_t V_{pij}}{J_{ij}}$$

In the equation above, $V_{pij}$ represents pore volume of a particular injection well and production well pair, $i$ represents an injection well, $j$ represents an production well, $c_t$ represents compressibility as function of time, $J_{ij}$ represents the productivity index for a particular injection well and production well pair, and Tau or $\tau_{ij}$ represents the response time of a particular injection well and production well pair.

Also, the interwell connectivity per injection well and production well pair for the first flood operation may be generated by CRM using the following equation:

$$f_{ij} = \frac{q_{ij}}{I_i}$$

In the equation above, $q_{ij}$ represents the total flow rate for a particular injection well and production well pair, $I_i$ represents the total flow rate for a particular injection well, $i$ represents an injection well, $j$ represents an production well, and $f_{ij}$ represents the interwell connectivity between a particular injection well and production well pair.

The productivity index $J_{ij}$ between a particular injection well and production well pair may be calculated as follows:

$$J_{ij} = \frac{I_i f_{ij}}{\Delta P_{ij}}$$

In the equation above, $\Delta P_{ij}$ represents the pressure difference between a particular injection well and a production well and the other terms are discussed hereinabove.

CRM may be run with or without allowed well connections as described herein. CRM may generate the response times and interwell connectivities for the first injection well $I_1$ and the six production wells drilled into the hydrocarbon reservoir. Alternatively, if this example included hundreds of wells in addition to the first injection well $I_1$ and the six production wells drilled into the reservoir, CRM may generate response times and interwell connectivities for the first flood operation for all injection well and production well pairs and the generated response times and interwell connectivities for the well pairs of interest may be used at 2006.

The following table A illustrates the generated response times in the second column, steady state interwell connectivities in the third column for an infinite period of time (fij), and transient interwell connectivities in the fifth column for a specified period of time (f*ij) for $Inj_1$ and $P_1$, $P_2$, $P_3$, $P_4$, $P_5$, $P_6$ for the first flood operation:

TABLE A

Injection well $Inj_1$ and production wells $P_1$-$P_6$ - first flood operation

| Producers | Response time (τ) Response time Proxy | fij -interwell connectivity (steady state) | Equation results with steady state fij Swept Pore Volume Proxy (steady state) | f*ij -interwell connectivity (max duration of the flood) | Equation results with transient f*ij Swept Pore Volume Proxy (max duration of the flood) |
|---|---|---|---|---|---|
| $P_1$ | 10 | 0.30 | 153,846 | 0.30 | 153,846 |
| $P_2$ | 10 | 0.20 | 106,667 | 0.20 | 106,667 |
| $P_3$ | 10 | 0.20 | 95,238 | 0.20 | 95,238 |
| $P_4$ | 50 | 0.10 | 246,914 | 0.09 | 233,053 |
| $P_5$ | 20 | 0.10 | 111,111 | 0.10 | 111,028 |
| $P_6$ | 80 | 0.10 | 410,256 | 0.08 | 342,441 |
|  | 180 | Total swept Pore volume For $Inj_1$ | 1,124,032 |  | 1,042,274 |
|  |  | Lorenz Coefficient For first flood operation | .44 |  |  |

At 2006, the generated response times, the generated interwell connectivities, the received production data, the received injection data, or any combination thereof may be used to generate a proxy of pore volume swept per injection well and production well pair for the first flood operation. Disclosed herein are three methodologies to generate the proxy of pore volume swept per injection well and production well pair for the first flood operation. Each of the three methodologies will be discussed, but those of ordinary skill in the art will appreciate that all three methodologies are not necessary. For example, the second methodology only may be used throughout. As another example, the third methodology only may be used throughout.

The first methodology to generate a proxy of pore volume swept for a particular injection well and production well pair is to treat the generated response time for the particular pair as the proxy of pore volume swept. Thus, using the generated response time, the proxy for $Inj_1$ and $P_1$ is 10, the proxy for $Inj_1$ and $P_2$ is 10, the proxy for $Inj_1$ and $P_3$ is 10, the proxy for $Inj_1$ and $P_4$ is 50, the proxy for $Inj_1$ and $P_5$ is 20, and the proxy for $Inj_1$ and $P_6$ is 80.

The second methodology to generate a proxy of pore volume swept for a particular injection well and production well pair is to use the following equation with steady state interwell connectivities:

$$V_{pij} = \frac{\tau_{ij} f_{ij} I_i}{c_t \Delta P_{ij}}$$

In the equation above, $V_{pij}$ represents pore volume of a particular injection well and production well pair, $c_t$ represents compressibility as a function of time, $f_{ij}$ represents the interwell connectivity for an injection well and production well pair, Tau or $\tau_{ij}$ represents the response time of a particular injection well and production well pair, $\Delta P_{ij}$ represents the pressure difference between a particular injection well and a production well, and $I_i$ represents the total flow rate for a particular injection well. The above equation for $V_{pij}$ is a combination of the $J_{ij}$ and $\tau_{ij}$ equations. Thus, using the equation with steady state interwell connectivity, the proxy for $Inj_1$ and $P_1$ is 153,846, the proxy for $Inj_1$ and $P_2$ is 106,667, the proxy for $Inj_1$ and $P_3$ is 95,238, the proxy for $Inj_1$ and $P_4$ is 246,914, the proxy for $Inj_1$ and $P_5$ is 111,111, and the proxy for $Inj_1$ and $P_6$ is 410,256.

The third methodology to generate a proxy of pore volume swept for a particular injection well and production well pair is to use the following equation with transient interwell connectivities:

$$V_{pij} = \frac{\tau_{ij} f^*_{ij} I_i}{c_t \Delta P_{ij}}$$

In the equation above, the main difference is the use of $f^*_{ij}$ to represent a transient interwell connectivity for an injection well and production well pair. For the running example, 36 months was used for the transient interwell connectivities. Thus, using the equation with transient interwell connectivity, the proxy for $Inj_1$ and $P_1$ is 153,846, the proxy for $Inj_1$ and $P_2$ is 106,667, the proxy for $Inj_1$ and $P_3$ is 95,238, the proxy for $Inj_1$ and $P_4$ is 233,053, the proxy for $Inj_1$ and $P_5$ is 111,028, and the proxy for $Inj_1$ and $P_6$ is 342,441.

At 2008, the generated proxies of pore volume swept per injection well and production well pair for the first flood operation may be aggregated to generate an estimate of pore volume swept at a well level, at a reservoir level, or both for the first flood operation. The generated proxies may be aggregated using addition. The estimate of pore volume swept at the well level may be for a particular injection well or for a particular production well. Returning to the running example, the estimate of pore volume swept at the well level for $Inj_1$ based on the generated response time is 180. The estimate of pore volume swept at the well level for $Inj_1$ based on the equation with steady state interwell conductivities is 1,124,032. The estimate of pore volume swept at the well level for $Inj_1$ based on the equation with transient interwell conductivities is 1,042,274.

At 2010, heterogeneity at the well level, the reservoir level, or both may be determined for the first flood operation (e.g., by using the generated response times and the generated interwell connectivities). The heterogeneity may be determined to verify the accuracy of a change in sweep efficiency, discussed further at 2026. Heterogeneity of the first flood operation may be calculating using a Lorenz coefficient (Lc), Koval, a flow capacity-storage capacity curve, any combination thereof, etc. In some embodiments, the heterogeneity may be determined by quantifying the area below the flow capacity-storage capacity curve for the first flood operation. Heterogeneity is discussed further in U.S. Pat. No. 8,428,924, which is incorporated herein by reference in its entirety. In the running example, the heterogeneity at the well level for the first flood operation is 0.44182, as illustrated in FIG. 21A.

At 2012, 2014, 2016, 2018, 2020, a similar approach may be used for the second flood operation, as in Table B. Returning to the running example, the estimate of pore volume swept at the well level for the second flood operation based on the generated response time for $Inj_1$ is 275. The estimate of pore volume swept at the well level for the second flood operation based on the equation with steady state interwell conductivities for $Inj_1$ is 1,199,319. The estimate of pore volume swept at the well level for the second flood operation based on the equation with transient interwell conductivities for $Inj_1$ is 1,135,528. The heterogeneity at the well level for the second flood operation is 0.1182, as illustrated in FIG. 21B.

positive change in volumetric sweep (steady state). If the third methodology was used, then the change in sweep efficiency for $Inj_1$ is about 9% (i.e., (1,135,528−1,042,274)/1,042,274=0.0894*100=9%), which is a positive change in volumetric sweep (max duration of the flood).

Figure 21C:
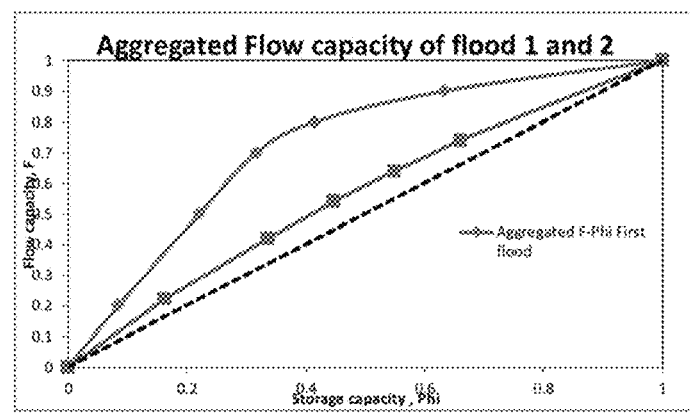

At 2024, the determined heterogeneity of the first flood operation and the determined heterogeneity of the second flood operation may be compared to determine a change in heterogeneity at the well level, at the reservoir level, or both. The comparison at 2022 may be performed before the comparison at 2024 or the comparison at 2024 may be performed before the comparison at 2022. Nonetheless, the change in heterogeneity may be determined by calculating the difference between the determined heterogeneity for the second flood operation and the determined heterogeneity for the first flood operation. The determined difference is divided by the determined heterogeneity for the first flood operation. Returning to the running example, at the well level, the heterogeneity for $Inj_1$ is about 73% (i.e., (0.44−0.12)/0.44=0.7272*100=73%) as illustrated in FIG. 21C, which is a Lorenz coefficient reduction.

TABLE B

Injection well $Inj_1$ and production wells $P_1$ $P_6$ - second flood operation

| Producers | Response time (τ) Response time Proxy | fij -interwell connectivity (steady state) | Equation results with fij Swept Pore VolumeProxy (steady state) | f*ij -interwell connectivity (max duration of the flood) | Equation results with f*ij Swept Pore Volume Proxy (max duration of the flood) |
|---|---|---|---|---|---|
| $P_1$ | 40 | 0.20 | 208,333 | 0.19 | 202,641 |
| $P_2$ | 50 | 0.10 | 134,409 | 0.09 | 126,864 |
| $P_3$ | 50 | 0.10 | 122,549 | 0.09 | 115,670 |
| $P_4$ | 35 | 0.22 | 194,444 | 0.22 | 191,268 |
| $P_5$ | 40 | 0.12 | 133,333 | 0.12 | 129,690 |
| $P_6$ | 60 | 0.26 | 406,250 | 0.24 | 369,396 |
| | 275 | Total swept Pore volume For $Inj_1$ | 1,199,319 | | 1,135,528 |
| | | Lorenz Coefficient for second flood operation | .12 | | |
| | | Positive change in volumetric sweep (steady state) | 7% | Positive change in volumetric sweep (max duration of the flood) | 9% |
| | | Lorenz coefficient reduction | 73% | | |

At 2022, the generated estimate of pore volume swept for the first flood operation and the generated estimate of pore volume swept for the second flood operation may be compared to determine a change in sweep efficiency at the well level, at the reservoir level, or both. The change in sweep efficiency may be determined by calculating the difference between the estimate of pore volume swept for the second flood operation and the estimate of pore volume swept for the first flood operation. The determined difference is divided by the estimate of pore volume swept for the first flood operation. Returning to the running example, if the first methodology was used, then the change in sweep efficiency for $Inj_1$ is about 53% (i.e., (275−180)/180=0.5277*100=53%), which is a positive change in volumetric sweep. If the second methodology was used, then the change in sweep efficiency for $Inj_1$ is about 7% (i.e., (1,199,319−1,124,032)/1,124,032=0.0669*100=7%), which is a At 2026, the determined change in heterogeneity and the determined change in sweep efficiency may be compared to verify accuracy of the determined change in sweep efficiency. In the running example, an inverse relationship may indicate that the determined change in sweep efficiency, regardless of the methodology used, is likely accurate. For instance, a positive change in volumetric sweep is consistent with a reduction in heterogeneity, and therefore a positive increase in 53%, 7%, or 9% is consistent with a reduction of 73% in heterogeneity.

Those of ordinary skill in the art will appreciate that various modifications may be made to the illustrated embodiments. For example, CRM may be run at 2004 and/or 2014 using allowed well connections as input, as discussed herein. The allowed well connections may be determined, and the running of the capacitance resistance modeling for the first flood operation, the second flood operation, or both includes using the determined allowed connections as an input to the capacitance resistance modeling.

Moreover, the first flood operation may be practically any flood operation and the second flood operation may be practically any flood operation, and the embodiments disclosed herein may be used to analyze them. For example, the first flood operation may be a polymer flood operation using a polymer at a first concentration, and the second flood operation may be a polymer flood operation using a polymer at a second concentration. Alternatively, the first flood operation may be a waterflood operation like in the running example, but the second flood operation may be a polymer flood operation with a surfactant and a polymer. Alternatively, the first flood operation may be a waterflood operation that uses a first brine and the second flood operation may be a waterflood operation that uses a second brine. The first brine and the second brine may be different, or the first brine and the second brine may be substantially similar in some embodiments.

Furthermore, the running example assumed one injection well for simplicity, but a change in sweep efficiency may be generated as described above for a plurality of injection wells. Indeed, the running example may include two injections wells, as illustrated further in FIGS. 22A-22B. Also, the embodiments discussed above can be applied at the reservoir level, as illustrated in FIGS. 23A-23G. Furthermore, the reservoir may include a plurality of zones, and each zone may be treated as an injection well, as illustrated in FIGS. 24A-24F.

Figure 25:
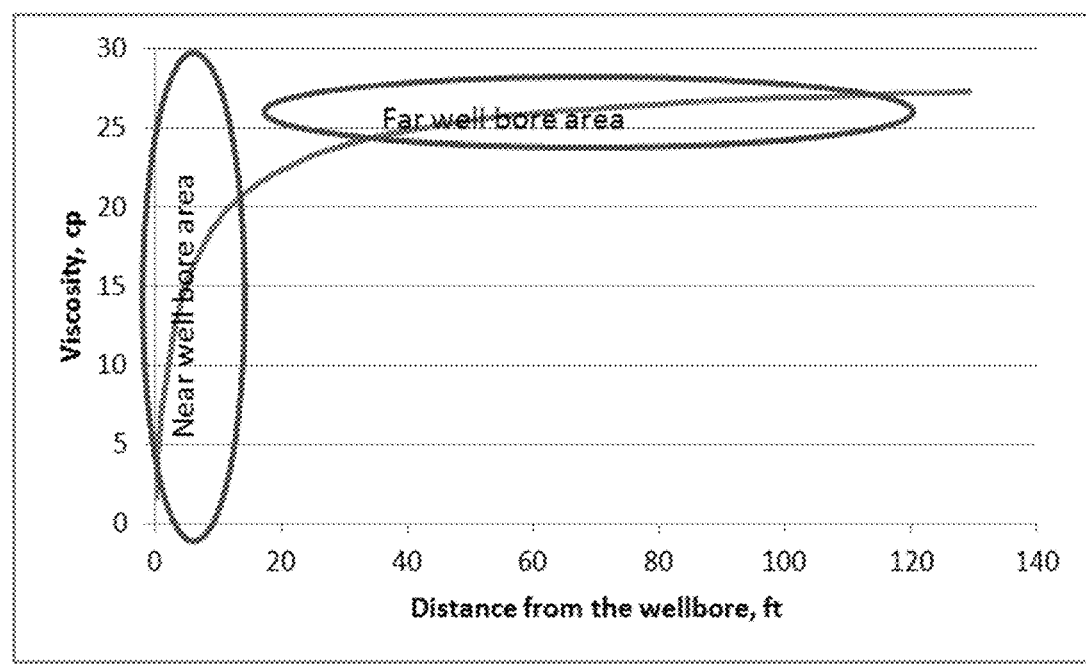
FIG. 25 illustrates one example of the sharp viscosity variation between near well bore areas to far well bore areas.

Optionally, if a flood operation uses a polymer alone or a polymer in combination with other material (e.g., surfactant), then the rheology of the polymer may be accounted for in CRM. In the running example, the second flood operation is a polymer flood operation, and therefore, the rheology of the polymer could have been accounted for in the running of CRM at 2014. Polymers used in oil fields oftentimes exhibit shear thinning rheology. Shear thinning rheology for a polymer oftentimes causes its viscosity to increase away from the well bore area. The viscosity variation may be sharp between near well bore areas to far well bore areas, as illustrated in FIG. 25. The polymer rheology can be mathematically described by at least one rheological model such as a power law model, Meters model, Carreau model, etc. based on laboratory experiments.

Figure 26:
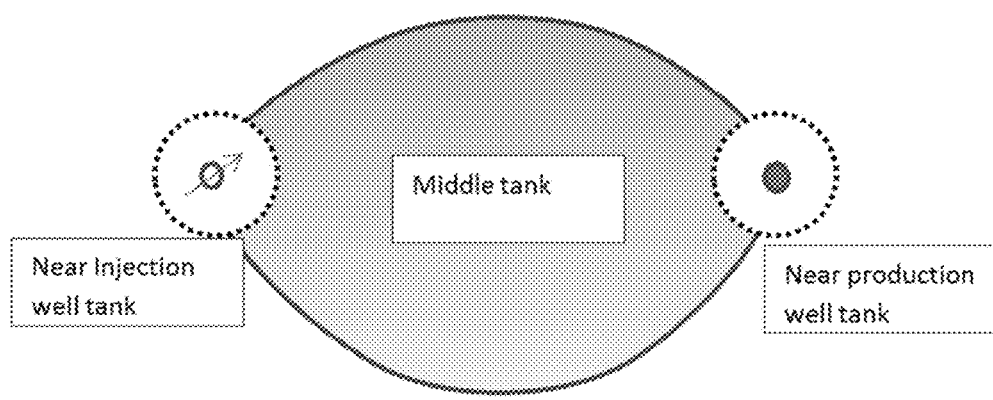
FIG. 26 illustrates one example of separating each injection well and production well pair of a polymer flood operation into three tanks including a near injection well tank, a near production well tank, and a middle tank between the near injection well tank and the near production well tank.

To account for the rheology in running CRM, accounting for the rheology includes separating each injection well and production well pair of the polymer flood operation into three tanks including a near injection well tank, a near production well tank, and a middle tank between the near injection well tank and the near production well tan, as illustrated in FIG. 26. By separating into at least three tanks, the rheology near well bore is separated from the rheology effects away from the well bore.

Furthermore, running the capacitance resistance modeling includes using (i) material balance equations for each of the tanks, (ii) injection and production well rates, (iii) injection and production well flowing pressure data, and (iv) the polymer rheology (e.g., using the power law model). The material balance equations are written out for each of the tanks separately as illustrated below. The near injection well tank material balance equation is:

$$c_t V_{p,i} \frac{\partial \overline{P}_i}{\partial t} = i_{i,p}(t) - q_i(t)$$

In the near injection well tank equation, $c_t$ is the total compressibility, $V_{p,i}$ is the pore volume of the near injection well tank associated with injection well i, $\overline{P}_i$ is the average pressure in the near injection well tank associated with injection well i, $i_{i,p}(t)$ is the flow rate of the polymer in injection well i and $q_i(t)$ is flow rate of the fluid out of the near injection well tank associated with the injection well i.

The near production well tank material balance equation is:

$$c_t V_{p,j} \frac{\partial \overline{P}_j}{\partial t} = \overline{q}_j(t) - (q_{p,j}(t) + q_{o,j}(t))$$

In the near production well tank equation, $c_t$ is the total compressibility, $V_{p,j}$ is the pore volume of the near production well tank associated with production well j, $\overline{P}_j$ is the average pressure in the near production well tank associated with production well j, $\overline{q}_j(t)$ is the flow rate of the fluid in production well j, $q_{p,j}(t)$ is the polymer flow rate in production well j and $q_{o,j}(t)$ is the oil flow rate in production well j.

The middle tank material balance equation is:

$$c_t \overline{V}_{p,j} \frac{\partial \overline{P}_j}{\partial t} = \sum_{i=1}^{Ni} q_{i,j}(t) - \overline{q}_j(t)$$

In the middle tank equation, $c_t$ is the total compressibility, $q_{i,j}(t)$ is the interwell total flow rate between injection well i and production well j, $\overline{P}_j$ is the average pressure in the middle tank, $\overline{V}_{p,j}$ is the pore volume of the middle tank.

The CRM polymer formulation (a single equation, shown below) is obtained by the combination of the material balance equations for each of the tanks. The final CRM formulation thus depends (i) material balance equations for each of the tanks, (ii) injection and production well rates, (iii) injection and production well flowing pressure data, and (iv) the polymer rheology (e.g., using the power law model). The CRM polymer formulation is:

$$\overline{\tau}_j \tau_j \frac{\partial}{\partial t}\left(\frac{\partial(q_{p,j}^n(t) + q_{o,j}(t))}{\partial t} + J_j \frac{\partial P_{wf,j}}{\partial t}\right) + \overline{\tau}_j \frac{\partial}{\partial t}(q_{p,j}(t) + q_{o,j}(t)) + \left(\overline{\tau}_j \frac{J_j}{\overline{J}_j} + \tau_j\right)\left(\frac{\partial(q_{p,j}^n(t) + q_{o,j}(t))}{\partial t} + J_j \frac{\partial P_{wf,j}}{\partial t}\right) + (q_{p,j}(t) + q_{o,j}(t)) = \sum_{i=1}^{Ni} f_{i,j}\left(i_{i,p}(t) + \tau_i\left(\frac{\partial i_{i,p}^n(t)}{\partial t} - J_i \frac{\partial P_{wf,i}}{\partial t}\right)\right)$$

In the CRM polymer formulation, $\tau_i$ is the time constant for the near injection well tank associated with injection well i, $\tau_j$ is the time constant for the near production well tank associated with production well j, and $\overline{\tau}_j$ is the time constant for the middle tank. $J_i$ is the injectivity index for injection well i, $J_j$ is the productivity index for production well j and $\overline{J}_j$ is the productivity index for the middle tank. $P_{wf,j}$ is the well flowing pressure for production well j and $P_{wf,i}$ is the well flowing pressure for injection well i.

The output from CRM using the CRM polymer formulation above includes $\tau$ for each of the tanks and the interwell connectivities fij or f*ij for each injection well and production well pair, and CRM therefore also accounts for the rheology of the polymer of the flood operation. Those of ordinary skill in the art will appreciate that existing CRM cannot account for rheology of polymer, and therefore the embodiments disclosed herein may lead to more accurate CRM output for flood operations involving a polymer. In some embodiments, rheology of a polymer may be accounted for in running CRM separate from determining sweep efficiency and/or separate from determining heterogeneity, as illustrated in an embodiment of a method of analyzing a polymer flood operation on a hydrocarbon reservoir in FIG. 27 (e.g., at method 2700, numbers 2702-2710).

Those of ordinary skill in the art may appreciate that analysis of a first flood operation and a second flood operation may have various benefits. For example, the injection and production field data of the polymer flood may be used via CRM to characterize the sweep efficiency improvement and performance of the polymer flood on the fly. This development may help with the following: 1. Optimizing a polymer flood while in progress by making changes such as adjusting injection-production rates or bottom hole pressures of wells to re-direct flow to un-swept volumes and improve performance of the polymer flood operation, 2. Design/optimize operational parameters of a polymer floods based on waterflood operation performance (e.g., choose optimal polymer concentrations, optimize injection-production rates and pressures, etc.), 3. Analyze the performance of a past polymer flood (pilot) to determine potential of future implementations, 4. Analyze a polymer flood pilot and use the incremental sweep efficiency information obtained to design future polymer floods, and/or 5. Determine infill drilling opportunities for the undergoing polymer flood to increase hydrocarbon recovery. Manipulation of CRM fundamental equations allows calculation of improved sweep efficiency by polymer floods from CRM analysis of polymer floods and comparison to the corresponding waterflood CRM performance. Time scale of connection or response time (tau) and well pair connectivities (fij) are used to calculate incremental sweep efficiency of polymer flood. As discussed above, this effort is not limited to waterfloods and polymer floods, and for example, may be applied to surfactant-polymer flood operations. This capability may allow robust design and optimization of chemical enhanced oil recovery (CEOR) processes based on field data. It may also help improve the performance of floods on the fly, which can change the outcome of a project from a failure to a success, potentially saving millions of dollars.

Pattern Management

Oftentimes, injection wells and production wells are drilled in locations so as to form patterns. Polygons are sometimes generated to represent the patterns. The embodiments discussed herein relate to (i) using producer centered (e.g., Voronoi) polygons to help identify infill drilling locations, (ii) using the polygons in choosing between two infill candidates in two different reservoirs, (iii) using the polygons (e.g., streamgrids) for converting an existing production well into an injection well or vice versa (referred to as pattern realignment, (iv) using polygon (e.g., streamgrid) allocation factors to initiate CRM interwell connectivity, and/or (v) estimating maximal areal sweep by zone and by reservoir with the populated polygons (e.g., streamgrids). The embodiments can be executed by a computing system, such as the computing system 200 of FIG. 2A or the polygon application 216 thereof. As discussed herein, a polygon may be a streamgrid or streamgrid polygon in some embodiments. After executing the embodiments, the output may be used as input to update or integrate with the CRM application 214, the zonal application 218, the petrotechnical mapping application 220, the one or more other application 221, the flooding analysis application 212, and/or other item (e.g., as illustrated in FIG.).

Figures 28A, 28B:
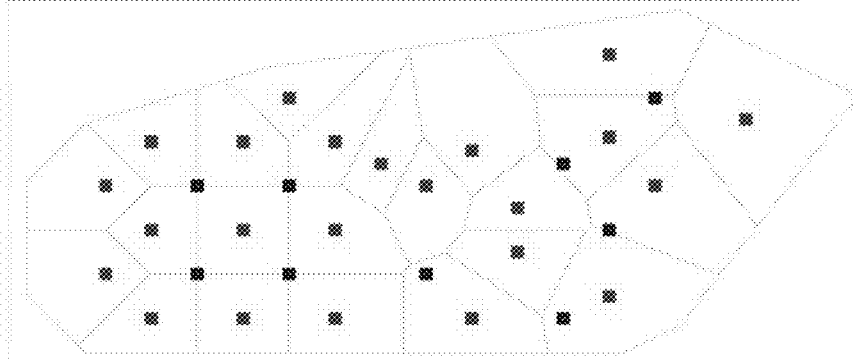
FIGS. 28A, 28B illustrate one embodiment of a computer implemented method for using producer centered (e.g., Voronoi) polygons to help identify infill drilling locations and an example thereof.

FIG. 28A illustrates one embodiment of a method for using producer centered (e.g., Voronoi) polygons to help identify infill drilling locations, referred to herein as method 2800. The method 2800 includes (i) loading or receiving well locations, reservoir boundary, and injection and production rate histories, (ii) creating producer-centered (e.g., Voronoi) polygons based on the producer locations and the reservoir boundary (or any fault, etc.), (iii) calculating the area (Ai) (e.g., drainage area, pore volume, proxy of OOIP, etc.) of any given producer by each polygon associated with each producer based on geometry or the geological boundary of the polygon, (iv) for each producer, calculating cumulative oil production (Qi) and a ratio between Qi and Ai, (v) ranking the producers from the smallest to largest Q/A ratio, and/or (vi) locating or indicating infill drilling places in the polygons with high-ranking producers. FIG. 28B and the following table illustrate an example.

| Producer | Area of producer-centered polygon (A) | Cumulative Oil Production from each producer (Q) | Ratio (Q/A) | Rank |
| --- | --- | --- | --- | --- |
| 1 | 35 | 1269 | 36.3 | 2 |
| 2 | 23 | 6389 | 277.8 | 7 |
| 3 | 82 | 8929 | 108.9 | 4 |
| 4 | 22 | 9827 | 446.7 | 9 |
| 5 | 57 | 6492 | 113.9 | 5 |
| 6 | 33 | 446 | 13.5 | 1 |
| 7 | 15 | 8921 | 594.7 | 10 |
| 8 | 24 | 8956 | 373.2 | 8 |
| 9 | 45 | 8013 | 178.1 | 6 |
| 10 | 45 | 1643 | 36.5 | 3 |

Figure 29B:
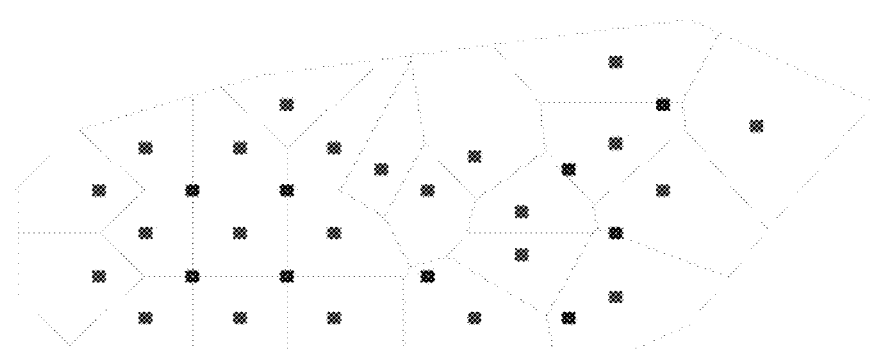
Figure 29C:
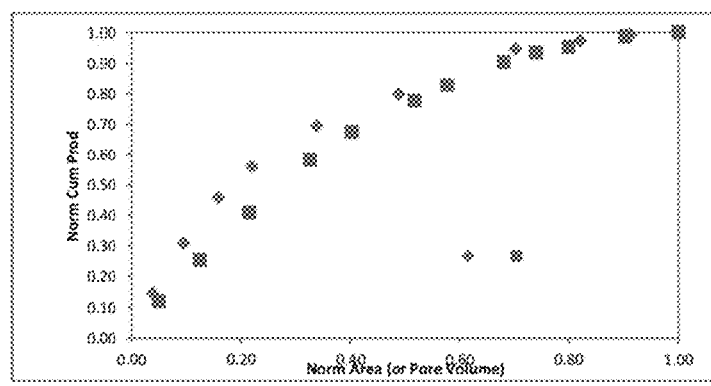

FIG. 29A illustrates one embodiment of a computer implemented method for using polygons to choose between two infill candidates in two different reservoirs, referred to herein as the method 2900. The method 2900 includes (i) loading or receiving well locations, reservoir boundary, and injection and production rate histories, (ii) creating producer-centered (e.g., Voronoi) polygons based on the producer locations and the reservoir boundary (or any fault, etc.), (iii) calculating the area ($A_i$) (e.g., drainage area, pore volume, proxy of OOIP, etc.) covered by each polygon associated with each producer based on geometry (or the geological boundary) of the polygon, (iv) for each producer, calculating cumulative oil production (Qi) and rank producers from largest Q to smallest Q, (v) for each producer, calculating cumulative oil production (Qi) and a ratio between Qi and Ai, (vi) ranking the producers from the smallest to largest Q/A ratio, (vii) calculating a norm area (or Pore volume) and norm cumulative oil production in that reservoir, and/or (viii) calculating an index of uneven sweep (IUS) of the reservoir. The method 2900 further includes (viiii) repeating (i)-(viii) for another reservoir, and ranking the reservoir for infill drilling opportunity with the largest IUS. FIGS. 29B-29C and the following table illustrate an example.

| Producer | Area (or Pore Volume) of Producer-centered Polygon (A) | Cumulative Oil Production from each producer (Q) | Ratio (Q/A) | Rank | Norm Area (or Pore Volume) | Norm Cum Oil | |
|---|---|---|---|---|---|---|---|
| Reservoir 1 | | | | | | | |
| 7 | 15 | 8921 | 594.7 | 1 | 0.04 | 0.15 | 0.002884 |
| 4 | 22 | 9827 | 446.7 | 2 | 0.10 | 0.31 | 0.016005 |
| 8 | 24 | 8956 | 373.2 | 3 | 0.16 | 0.46 | 0.040035 |
| 2 | 23 | 6389 | 277.8 | 4 | 0.22 | 0.56 | 0.07067 |
| 9 | 45 | 8013 | 178.1 | 5 | 0.34 | 0.69 | 0.144579 |
| 5 | 57 | 6492 | 113.9 | 6 | 0.49 | 0.80 | 0.256018 |
| 3 | 82 | 8929 | 108.9 | 7 | 0.70 | 0.94 | 0.443589 |
| 10 | 45 | 1643 | 36.5 | 8 | 0.82 | 0.97 | 0.556779 |
| 1 | 35 | 1269 | 36.3 | 9 | 0.91 | 0.99 | 0.647012 |
| 6 | 33 | 446 | 13.5 | 10 | 1.00 | 1.00 | 0.733309 |
| sum | 381 | 60885 | | | | IUS | 0.467 |
| Reservoir 2 | | | | | | | |
| 9 | 38 | 6522 | 171.6 | 1 | 0.05 | 0.12 | 0.003021 |
| 2 | 57 | 7304 | 128.1 | 2 | 0.13 | 0.25 | 0.017157 |
| 5 | 68 | 8452 | 124.3 | 3 | 0.22 | 0.41 | 0.04708 |
| 7 | 83 | 9381 | 113.0 | 4 | 0.33 | 0.58 | 0.101643 |
| 6 | 57 | 4921 | 86.3 | 5 | 0.40 | 0.67 | 0.149051 |
| 4 | 87 | 5688 | 65.4 | 6 | 0.52 | 0.78 | 0.232659 |
| 10 | 45 | 2786 | 61.9 | 7 | 0.58 | 0.83 | 0.280552 |
| 8 | 79 | 4218 | 53.4 | 8 | 0.68 | 0.90 | 0.371375 |
| 3 | 44 | 1697 | 38.6 | 9 | 0.74 | 0.94 | 0.425132 |
| 12 | 44 | 1000 | 22.7 | 10 | 0.80 | 0.95 | 0.480336 |
| 1 | 79 | 1747 | 22.1 | 11 | 0.90 | 0.99 | 0.582096 |
| 11 | 72 | 764 | 10.6 | 12 | 1.00 | 1.00 | 0.677043 |
| Sum | 753 | 54480 | | | | IUS | 0.354 |

FIG. 30A illustrates one embodiment of a computer implemented method for using polygons (e.g., streamgrids) for pattern realignment, referred to herein as the method 3000. The method 2800 includes (i) loading or receiving well locations, and injection and production rate histories for all wells, (ii) creating polygons (e.g., streamgrid polygons) based on the well locations, (iii) calculating allocation factors for injector and producers based on any available allocation method (e.g., injection angle, producer angle), (iv) calculating the allocated water injection and water production within each polygon (e.g., streamgrid) (between connected injector-producer pair), (v) calculating water cycling between connected injector-producer pair for each polygon (e.g., streamgrid), (vi) defining a threshold for water cycling based on a distribution, and/or (vii) identifying at least one polygon (e.g., streamgrid) that have water cycling above the threshold and convert the producer in that polygon (e.g., streamgrid) for pattern realignment. FIGS. 30B-30C illustrate an example.

Figure 31A:
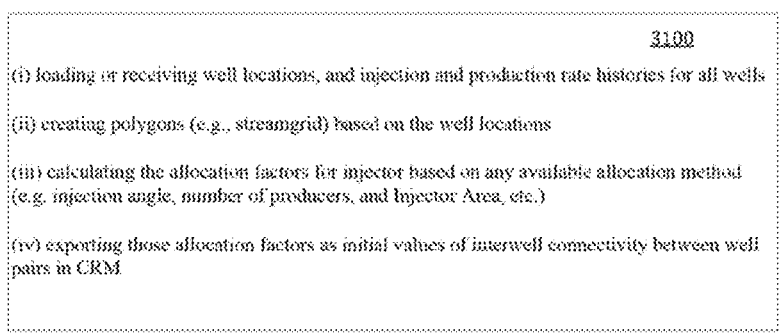
Figure 31B:
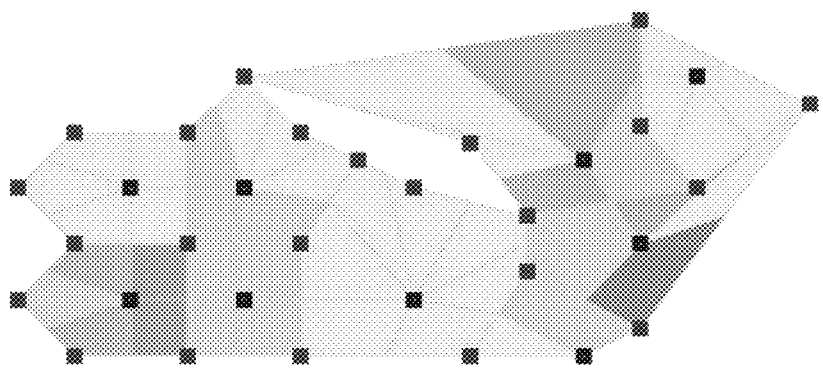
Figure 35D:
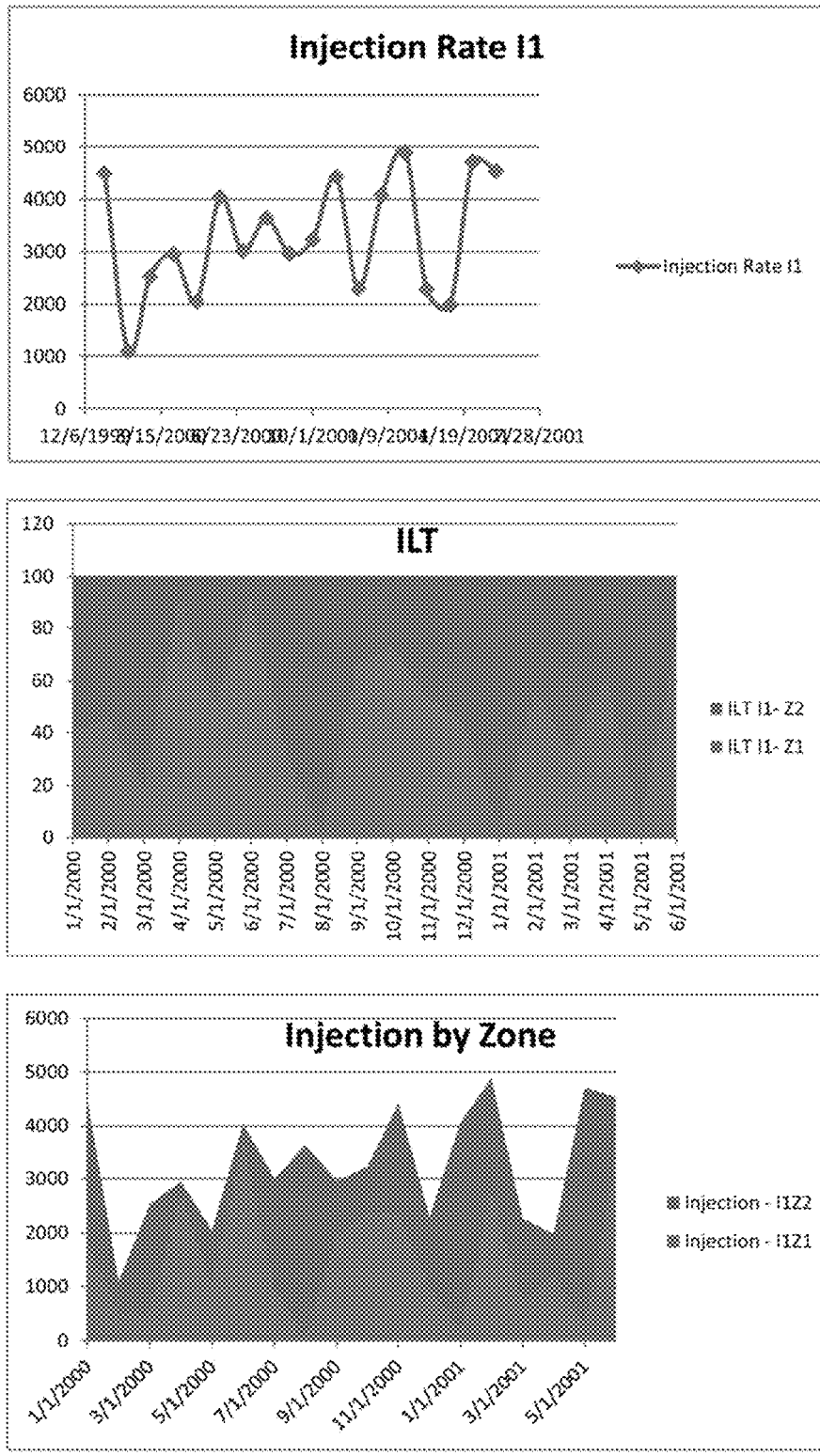
Figure 36G:
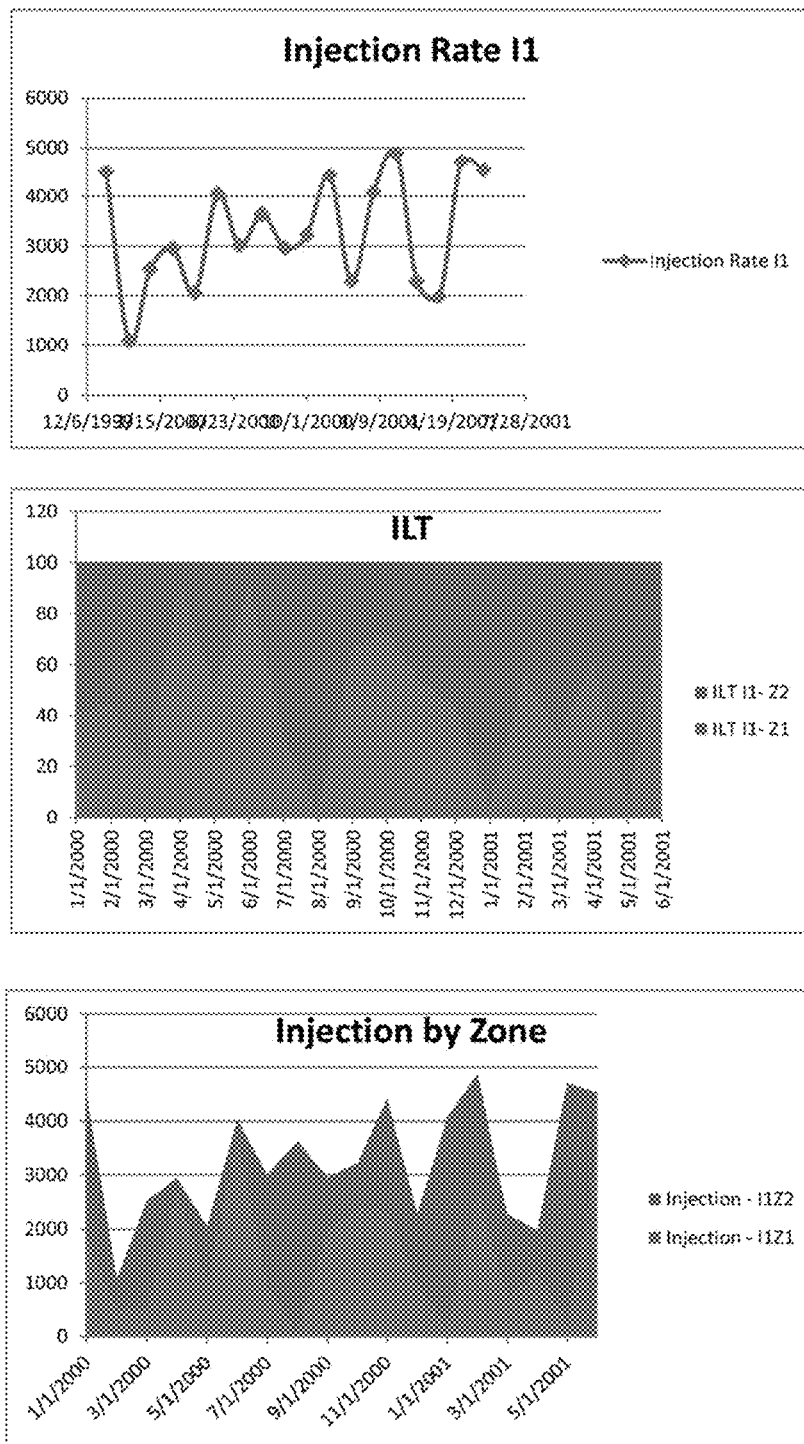
Figure 37I:
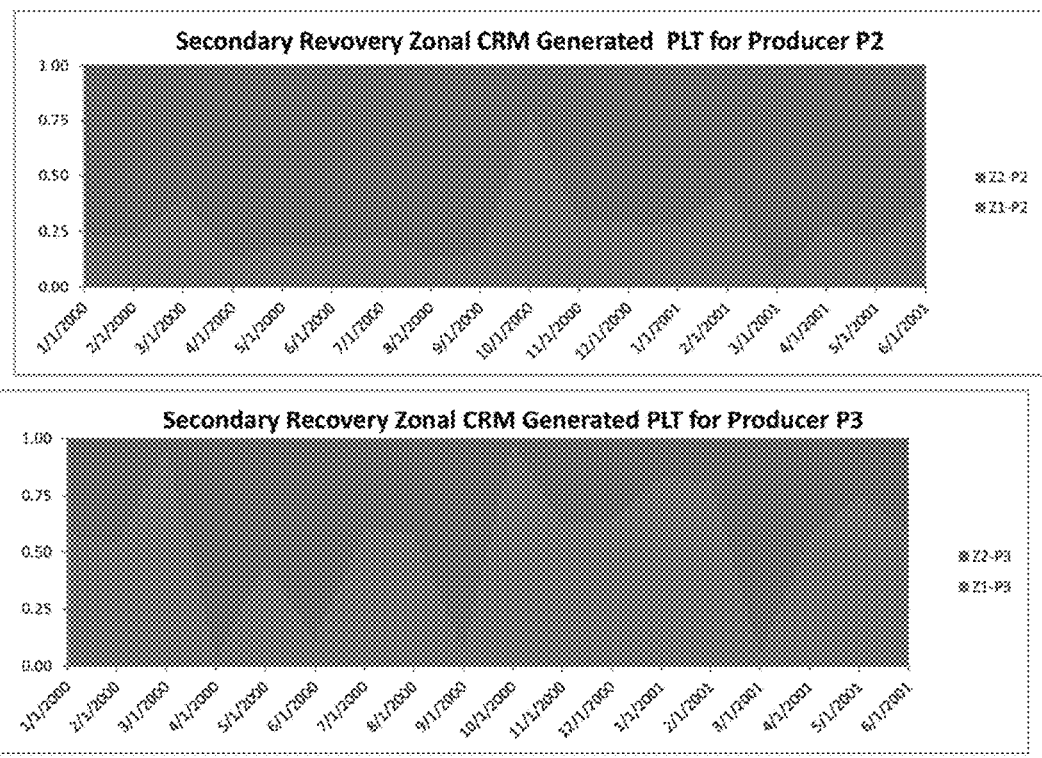

FIG. 31A illustrates one embodiment of a computer implemented method for using polygons (e.g., streamgrid) allocation factors to initiate CRM interwell connectivity, referred to herein as the method 3100. The method 3100 includes (i) loading or receiving well locations, and injection and production rate histories for all wells, (ii) creating polygons (e.g., streamgrid) based on the well locations, (iii) calculating the allocation factors for injector based on any available allocation method (e.g. injection angle, number of producers, and Injector Area, etc.), and/or (iv) exporting those allocation factors as initial values of interwell connectivity between well pairs in CRM. FIGS. 31B-31C illustrate an example.

FIG. 32A illustrates one embodiment of a computer implemented method for estimating maximal areal sweep by zone and by reservoir with the populated polygons (e.g., streamgrids), referred to herein as the method 3200. The method 3200 includes (i) for any given zone of a reservoir, getting a reservoir boundary in that zone and calculating its total area (St), (ii) getting contact point of all wells that penetrate and are perforated in that zone, (iii) creating streamgrid with the well-zone contact locations, (iv) calculating the total area (S) covered by populated streamgrids, and/or (v) estimating maximal areal sweep efficiency in that zone, which equals S/St. The method 3200 also includes repeating (i)-(v) for all zones in a reservoir and getting the S and St for each zone, calculate the ratio between summation of S from all zones and summation of St from all zones to get the maximum areal sweep efficiency for the reservoir. FIGS. 32B-32C illustrate an example.

Value of Injected Fluid (VOIF)

An embodiment of a computer implemented method of determining a value of injected fluid for a flood operation on a hydrocarbon reservoir having at least one injection well and at least one production well, referred to as 3300 in FIG. 33. The method 3300 can be executed by a computing system, such as the computing system 200 of FIG. 2A or the CRM application 214 thereof. After executing the method 2000 of FIG. 20, the resulting output may be used as input to update or integrate with the polygon application 216, the zonal application 218, the petrotechnical mapping application 220, the one or more other application 221, the flooding analysis application 212, and/or other item (e.g., FIGS. 2A, 2C). For ease of understanding, a running example will be used and the running example assumes five injection wells and four production wells.

At 3302, the method 3300, for a first injection well, receiving injection rate data for the first injection well and production rate data for at least one production well communicating with the injection well. At 3304, the method 3300 includes running capacitance resistance modeling using the received data to generate an interwell connectivity for each injection well and production well pair. CRM may be run using allowed well connections as described herein.

The table below illustrates the interwell connectivities:

Connectivity Values

CRM Parameters for Total Production Estimation

| | τ | Inj. 1 (f1j) | Inj. 2 (f2j) | Inj. 3 (f3j) | Inj. 4 (f4j) | Inj. 5 (f5j) | Jj | q(t = t0), B/D | qt_j Error, B/D |
|---|---|---|---|---|---|---|---|---|---|
| Pro. 1 | 365 | 0.3 | 0.2 | 0.5 | 0.25 | 0.25 | 0 | 3177 | 61.14295976 |
| Pro. 2 | 60 | 0.4 | 0.4 | 0 | 0.25 | 0.25 | 0 | 199 | 41.56255395 |
| Pro. 3 | 180 | 0.3 | 0.1 | 0.25 | 0.25 | 0.1 | 0 | 187 | 28.98366241 |
| Pro. 4 | 180 | 0 | 0.1 | 0.25 | 0.25 | 0.25 | 0 | 2333 | 33.53199791 |
| Sum fij =< 1 | | 1 | 0.8 | 1 | 1 | 0.85 | | | 41.30529351 |
| Injection Efficiency: | | 0.925 | | | | | | | |
| Target VRR: | | 1.081 | | | | | | | |

At 3306, the method 3300 includes determining a value of injected fluid for each injection well and production well pair using the generated interwell connectivity for the well pair and an oil-cut value for the production well of the pair. In some embodiments, determining the value of injected fluid per well pair includes using an equation for each well pair, wherein the equation is:

$$VOIF_{ij} = f_{ij} f_{oj}$$

In the equation, $f_{oj}$ is oil cut and $f_{ij}$ is interwell connectivity. In some embodiments, the $f_{ij}$ may be at a steady state as discussed herein. Alternatively, if transient is desired, then fij may be replaced with f*ij in the equation.

At 3308, the method 3300 includes aggregating the generated values of injected fluid per pair to determine a value of injected fluid for the first injection well. In the running example, the final value of injected fluid for the first injection well is 0.37 at steady state by aggregating the four values of injected fluid per well pair (0.15+0.16+0.06+0=0.37).

At 3310, the method 3300 includes generating a value of injected fluid for at least one other injection well. At 3312, the method 3300 includes ranking the first injection well and the at least one other injection well based on the values of injected fluid. Returning to the running example, at the steady state, the ranking and intermediate items may be the following:

Steady State Connectivities

| VOIF Table Time | Steady State Connectivities 1E + 13 days | | | | | | |
|---|---|---|---|---|---|---|---|
| fij Steady State | Inj. 1 | Inj. 2 | Inj. 3 | Inj. 4 | Inj. 5 | | Last Year Oil cut / Oil-Cut j |
| Pro. 1 | 0.30 | 0.20 | 0.50 | 0.25 | 0.25 | Pro. 1 | 0.5 |
| Pro. 2 | 0.40 | 0.40 | 0.00 | 0.25 | 0.25 | Pro. 2 | 0.4 |
| Pro. 3 | 0.30 | 0.10 | 0.25 | 0.25 | 0.10 | Pro. 3 | 0.2 |
| Pro. 4 | 0.00 | 0.10 | 0.25 | 0.25 | 0.25 | Pro. 4 | 0.2 |
| Sum fij | 1 | 0.8 | 1 | 1 | 0.85 | | |

Calculate VOIF for each wellpair - Sum for Injectors, Rank Injectors For One Barrel
Table Steady State
Value of Injected Fluid (VOIF) Evaluation

| for 1 bbl of injection | 1 | 1 | 1 | 1 | 1 |
|---|---|---|---|---|---|

-continued

| VOIF*_ij | Inj. 1 | Inj. 2 | Inj. 3 | Inj. 4 | Inj. 5 |
|---|---|---|---|---|---|
| Pro. 1 | 0.15 | 0.1 | 0.25 | 0.125 | 0.125 |
| Pro. 2 | 0.16 | 0.16 | 0 | 0.1 | 0.1 |
| Pro. 3 | 0.06 | 0.02 | 0.05 | 0.05 | 0.02 |
| Pro. 4 | 0 | 0.02 | 0.05 | 0.05 | 0.05 |
| VOIF_i | 0.37 | 0.3 | 0.35 | 0.325 | 0.295 |
| Steady State Rank | 1 | 4 | 2 | 3 | 5 |

At 3314, the method 3300 may include generating a net value of injected fluid for the first injection well and the at least one other injection well. The net value for a particular injection well may be determines using the following equations:

$$\text{Net VOIF}_i = \Sigma_j^N f_{ij} I_i f_{oj} \text{ OR Net VOIF}_{ij} = f_{ij} I_i f_{oj}$$

At 3316, the method 3300 includes reranking the first injection well and the at least one other injection well based the net values of injected fluid. In the running example, for steady state, the reranking may be:

Calculate Net Value of Injection - Steady State
For Current Injection
Steady State
Net Value of Injected Fluid (VOIF) Evaluation

| Current Inj_i, B/D | 1000 | 500 | 1000 | 500 | 1000 |
|---|---|---|---|---|---|
| Net VOIF_ij | Inj. 1 | Inj. 2 | Inj. 3 | Inj. 4 | Inj. 5 |
| Pro. 1 | 150 | 50 | 250 | 62.5 | 125 |
| Pro. 2 | 160 | 80 | 0 | 50 | 100 |
| Pro. 3 | 60 | 10 | 50 | 25 | 20 |
| Pro. 4 | 0 | 10 | 50 | 25 | 50 |
| Net VOIF_i | 370 | 150 | 350 | 162.5 | 295 |
| Rank | 1 | 5 | 2 | 4 | 3 |

In the running example, assuming transient, the following tables illustrate the items that may be generated:

Transient Connectivities

| VOIF Table 2 B Time | 6 month 180 days | | | | | |
|---|---|---|---|---|---|---|
| fij Transient | Inj. 1 | Inj. 2 | Inj. 3 | Inj. 4 | Inj. 5 | Last Year Oil cut / Oil-Cut j |

Transient Connectivities

| | | | | | | | |
|---|---|---|---|---|---|---|---|
| Pro. 1 | 0.12 | 0.08 | 0.19 | 0.10 | 0.10 | Pro. 1 | 0.5 |
| Pro. 2 | 0.38 | 0.38 | 0.00 | 0.24 | 0.24 | Pro. 2 | 0.4 |
| Pro. 3 | 0.19 | 0.06 | 0.16 | 0.16 | 0.06 | Pro. 3 | 0.2 |
| Pro. 4 | 0.00 | 0.06 | 0.16 | 0.16 | 0.16 | Pro. 4 | 0.2 |
| Sum Transient fij | 0.69 | 0.58 | 0.51 | 0.65 | 0.56 | | |

Calculate VOIF for each well pair - Sum for Injectors, Rank Injectors
For One Barrel
Table Transient

| Value of Injected Fluid (VOIF) Evaluation for 1 bbl of injection | 1 | 1 | 1 | 1 | 1 |
|---|---|---|---|---|---|
| VOIF*_ij | Inj. 1 | Inj. 2 | Inj. 3 | Inj. 4 | Inj. 5 |
| Pro. 1 | 0.06 | 0.04 | 0.10 | 0.05 | 0.05 |
| Pro. 2 | 0.15 | 0.15 | 0.00 | 0.10 | 0.10 |
| Pro. 3 | 0.04 | 0.01 | 0.03 | 0.03 | 0.01 |
| Pro. 4 | 0.00 | 0.01 | 0.03 | 0.03 | 0.03 |
| VOIF_i | 0.25 | 0.22 | 0.16 | 0.21 | 0.19 |
| Transient Rank | 1 | 2 | 5 | 3 | 4 |

Calculate VOIF for each well pair - Sum for Injectors, Rank Injectors
For Current Injection
Transient

| Net Value of Injected Fluid (VOIF) Evaluation Current Inj_i, B/D | 1000 | 500 | 1000 | 500 | 1000 |
|---|---|---|---|---|---|
| Net VOIF_ij | Inj. 1 | Inj. 2 | Inj. 3 | Inj. 4 | Inj. 5 |
| Pro. 1 | 58 | 19 | 97 | 24 | 49 |
| Pro. 2 | 152 | 76 | 0 | 48 | 95 |
| Pro. 3 | 38 | 6 | 32 | 16 | 13 |
| Pro. 4 | 0 | 6 | 32 | 16 | 32 |
| Net VOIF_i | 248 | 108 | 161 | 103 | 188 |
| Rank | 1 | 4 | 3 | 5 | 2 |

Those of ordinary skill in the art will appreciate that modifications may be made to the illustrated embodiments. For example, the hydrocarbon reservoir may include a plurality of zones, and each zone is treated as an injection well as described above. Indeed, VOIF may be determined at a well level or at a zonal level. Furthermore, sensitivity analysis may be used. For example, (i) sensitivity analysis may be performed to determine the allowed well connections for CRM, (ii) CRM may be run with sensitivity analysis, (iii) VOIF may be determined for an injection well at the steady state with or without sensitivity analysis, and/or (iv) VOIF may be determined for an injection well as transient with or without sensitivity analysis. VOIF may also be used to recommend a target injection rate. VOIF may also be used to recommend a conformance candidate (e.g., if f*ij or fij is more than a threshold such as 0.4, and if VOIF is less than a threshold such as 0.1, and if injection rate is more than average, then the method 3300 may recommend the corresponding well and/or zone as a conformance candidate). Criteria may also be used to recommend a stimulation candidate. Thus, at 3318, the method 3300 may generate a recommendation. Also, in some embodiments, PLT can be a substitute for oil-cut in determining VOIF.

CRM Zonal

CRM General Formulation: In one example, a representation of a producer is interacting with offset injectors in which a fraction of each injector injection rate ($f_{ij}$) is contributing to the production rate of producer j. Because CRM is derived based on the continuity equation, all the model parameters reflect physical characteristics of the reservoir. Interwell connectivities ($f_{ij}$), delay time constants ($\tau_{ij}$), and productivity indices ($J_{ij}$) between any injector i (i=1, 2, ..., $N_{inj}$) and producer j (j=1, 2, ..., $N_{pro}$) are CRM model parameters and are back-calculated during the course of simultaneous fitting of Eq. 1 to the fluid production of all producers. CRM formulation is based on producer control volume and can be written as:

$$q_j(t_n) = q_j(t_0) e^{-\left(\frac{t_n - t_0}{\tau_j}\right)} + \sum_{k=1}^{n} e^{-\left(\frac{t_n - t_0}{\tau_j}\right)} \left(1 - e^{\frac{-\Delta t_k}{\tau_j}}\right) \left(\sum_{i=1}^{N_{inj}} [f_{ij} I_i^{(k)}] - J_j \tau_j \frac{\Delta p_{wf,j}^{(k)}}{\Delta t_k}\right) \quad (1)$$

(for j = 1, 2, ..., $N_{pro}$)

Where $I_i^{(k)}$ and $\Delta p_{wf,j}^{(k)}$ represent the rate of injector i and changes in flowing bottomhole pressure of producer j during time interval $\Delta t_k = t_k - t_{k-1}$, respectively.

As Eq. 1 illustrates, fluid production rate at producer j is composed of three elements: primary depletion the first term, the impact of injection input signals, and the variation caused by changing the bottomhole pressure of producer j.

CRM Zonal and its application in generating continuous production profile over time: Zonal connectivity can be identified by CRM using ILT data. Injection profile data obtained over time can be used to split injection to the zonal level. Assuming no vertical communication between different zones, and using the injection profile and injection rates each injector gets split into multiple zonal level injectors. The Table below illustrates the breakdown of injection rate from one injector (I1) over time into two zones (Z1 and Z2) as an example.

Injection Profile

| | | Zonal split from ILT (%) | | Zonal Injection Rate | |
|---|---|---|---|---|---|
| | Date | Injection Rate I1 | ILT I1-Z1 | ILT I1-Z2 | Injection-I1Z1 | Injection-I1Z2 |
| 1 | Jan. 1, 2000 | 4490 | 41 | 59 | 1840.9 | 2649.1 |
| 2 | Feb. 1, 2000 | 1090 | 45 | 55 | 490.5 | 599.5 |
| 3 | Mar. 1, 2000 | 2530 | 20 | 80 | 506 | 2024 |
| 4 | Apr. 1, 2000 | 2950 | 92 | 8 | 2714 | 236 |
| 5 | May 1, 2000 | 2050 | 51 | 49 | 1045.5 | 1004.5 |
| 6 | Jun. 1, 2000 | 4040 | 91 | 9 | 3676.4 | 363.6 |
| 7 | Jul. 1, 2000 | 3010 | 32 | 68 | 963.2 | 2046.8 |
| 8 | Aug. 1, 2000 | 3640 | 2 | 98 | 72.8 | 3567.2 |
| 9 | Sep. 1, 2000 | 2960 | 67 | 33 | 1983.2 | 976.8 |
| 10 | Oct. 1, 2000 | 3230 | 73 | 27 | 2357.9 | 872.1 |
| 11 | Nov. 1, 2000 | 4420 | 53 | 47 | 2342.6 | 2077.4 |
| 12 | Dec. 1, 2000 | 2290 | 44 | 56 | 1007.6 | 1282.4 |
| 13 | Jan. 1, 2001 | 4080 | 4 | 96 | 163.2 | 3916.8 |
| 14 | Feb. 1, 2001 | 4880 | 56 | 44 | 2732.8 | 2147.2 |
| 15 | Mar. 1, 2001 | 2280 | 33 | 67 | 752.4 | 1527.6 |
| 16 | Apr. 1, 2001 | 1980 | 61 | 39 | 1207.8 | 772.2 |
| 17 | May 1, 2001 | 4710 | 6 | 94 | 282.6 | 4427.4 |
| 18 | Jun. 1, 2001 | 4530 | 75 | 25 | 3397.5 | 1132.5 |

Following the splitting of an injector well into multiple zonal level injectors, a capacitance resistance model is generated in which each zonal level injector is treated as a single injector, therefore interwell connectivities are obtained at the zonal level for at least one injector and the producers that it supports. In the running example with one injector (I1) and two zones (Z1 and Z2) and two producers (P1 and P2), interwell connectivities are obtained at the zonal level (fij) between injector I1 at zone Z1 and zone Z2 with the two producers P2 and P3 as shown in table below:

| CRM Connectivity at Zonal level- fij | | | |
|---|---|---|---|
| I1Z1-P2 | I1Z2-P2 | I1Z1-P3 | I1Z2-P3 |
| 0.2 | 0.4 | 0.8 | 0.6 |

The injected fluid can have a preferred flow path in different zones. The preferential flow path in the running example is shown in Table above. It shows that the injected fluid has a preferred flow path between Injector I1 and Producer P3 in zone Z2.

Secondary Production Application: Continuous production profile in case of if only secondary recovery is contributing in production is obtained from injection rates and zonal level connectivities by summing up contribution of zonal injectors and their connectivities to at least one of the producers.

At Zone 1 for Producer j:

$$q_j^{Z1}(t) = \sum_{i=1}^{N_{inj}} [f_{ij}^{Z1} I_i^{(Z1)}(t)]$$

(for $j = 1, 2, \ldots, N_{pro}$)

Considering the zonal level connectivities and injection rates, of the example above, CRM estimates of continuous production rate at the zonal level for contributing zones of producer P2 and P3 are obtained and shown in table below,

| | CRM Estimates of Secondary flux at zone level (qij = Injection rate by zone multiplied by connectivity @ zone 1 and 2) | | | |
|---|---|---|---|---|
| Date | I1Z1-P2 | I1Z2-P2 | I1Z1-P3 | I1Z2-P3 |
| Jan. 1, 2000 | 368 | 1060 | 1473 | 1589 |
| Feb. 1, 2000 | 98 | 240 | 392 | 360 |
| Mar. 1, 2000 | 101 | 810 | 405 | 1214 |
| Apr. 1, 2000 | 542 | 94 | 2171 | 142 |
| May 1, 2000 | 209 | 402 | 836 | 603 |
| Jun. 1, 2000 | 735 | 145 | 2941 | 218 |
| Jul. 1, 2000 | 192 | 819 | 771 | 1228 |
| Aug. 1, 2000 | 14 | 1427 | 58 | 2140 |
| Sep. 1, 2000 | 396 | 391 | 1587 | 586 |
| Oct. 1, 2000 | 471 | 349 | 1886 | 523 |
| Nov. 1, 2000 | 468 | 831 | 1874 | 1246 |
| Dec. 1, 2000 | 201 | 513 | 806 | 769 |
| Jan. 1, 2001 | 32 | 1567 | 131 | 2350 |
| Feb. 1, 2001 | 546 | 859 | 2186 | 1288 |
| Mar. 1, 2001 | 150 | 611 | 602 | 917 |
| Apr. 1, 2001 | 241 | 309 | 966 | 463 |
| May 1, 2001 | 56 | 1771 | 226 | 2656 |
| Jun. 1, 2001 | 679 | 453 | 2718 | 680 |

CRM estimates of production rates for contributing zone is normalized to provide production split of each zone as a continues value during the production of the producers, as shown in table below, these estimate are cross checked with sparse production profile data which also is considered in calibration of the CRM zonal level analysis.

| Date | Z1-P2 | Z2-P2 | check for P2, sum = 1 | Z1-P3 | Z2-P3 | Check for P3, sum = 1 |
|---|---|---|---|---|---|---|
| Jan. 1, 2000 | 0.26 | 0.74 | 1.00 | 0.48 | 0.52 | 1.00 |
| Feb. 1, 2000 | 0.29 | 0.71 | 1.00 | 0.52 | 0.48 | 1.00 |
| Mar. 1, 2000 | 0.11 | 0.89 | 1.00 | 0.25 | 0.75 | 1.00 |
| Apr. 1, 2000 | 0.85 | 0.15 | 1.00 | 0.94 | 0.06 | 1.00 |
| May 1, 2000 | 0.34 | 0.66 | 1.00 | 0.58 | 0.42 | 1.00 |
| Jun. 1, 2000 | 0.83 | 0.17 | 1.00 | 0.93 | 0.07 | 1.00 |
| Jul. 1, 2000 | 0.19 | 0.81 | 1.00 | 0.39 | 0.61 | 1.00 |
| Aug. 1, 2000 | 0.01 | 0.99 | 1.00 | 0.03 | 0.97 | 1.00 |
| Sep. 1, 2000 | 0.50 | 0.50 | 1.00 | 0.73 | 0.27 | 1.00 |
| Oct. 1, 2000 | 0.57 | 0.43 | 1.00 | 0.78 | 0.22 | 1.00 |
| Nov. 1, 2000 | 0.36 | 0.64 | 1.00 | 0.60 | 0.40 | 1.00 |
| Dec. 1, 2000 | 0.28 | 0.72 | 1.00 | 0.51 | 0.49 | 1.00 |
| Jan. 1, 2001 | 0.02 | 0.98 | 1.00 | 0.05 | 0.95 | 1.00 |
| Feb. 1, 2001 | 0.39 | 0.61 | 1.00 | 0.63 | 0.37 | 1.00 |
| Mar. 1, 2001 | 0.20 | 0.80 | 1.00 | 0.40 | 0.60 | 1.00 |
| Apr. 1, 2001 | 0.44 | 0.56 | 1.00 | 0.68 | 0.32 | 1.00 |
| May 1, 2001 | 0.03 | 0.97 | 1.00 | 0.08 | 0.92 | 1.00 |
| Jun. 1, 2001 | 0.60 | 0.40 | 1.00 | 0.80 | 0.20 | 1.00 |

Primary and Secondary Production Application: Continuous production profile from primary and secondary production is obtained by using the primary and secondary recovery portion of CRM estimate once the CRM zonal is performed. The Primary portion of production profile is estimated from CRM zonal level primary portion which is an exponential decline. The secondary portion of production rates at zonal level are obtained from summing the multiplication of injection rates and connectivities at zonal level from all injectors contributing in the production of a given producer.

Primary Portion of CRM:

$$q_j(t_0) e^{-\left(\frac{t_n - t_0}{\tau_{Primary,j}}\right)} - J_j \tau_{Primary,j} \frac{\Delta p_{wf,j}^{(k)}}{\Delta t_k} \left(1 - e^{\frac{-\Delta t_k}{\tau_{Primary,j}}}\right)$$

Secondary Portion of CRM:

$$\left(1 - e^{\frac{-\Delta t_k}{\tau_{Secondary,j}}}\right) \left(\sum_{i=1}^{N_{inj}} [f_{ij} I_i^{(k)}]\right)$$

(for $j = 1, 2, \ldots, N_{pro}$)

In the running example table below shows historical production, CRM estimate and its primary and secondary portions estimated from equation above,

| | Production Rate History | | Primary + Secondary | | Secondary Portion | | Primary Portion | |
|---|---|---|---|---|---|---|---|---|
| | Producer | Producer | CRM | CRM | CRM | CRM | CRM | CRM |
| Date | P2 | P3 | P2 | P3 | P2 | P3 | P2 | P3 |
| Jan. 1, 2000 | 2168 | 3717 | 2303 | 4032 | 1428 | 3062 | 876 | 969 |
| Feb. 1, 2000 | 887 | 1288 | 950 | 1349 | 338 | 752 | 612 | 597 |
| Mar. 1, 2000 | 1317 | 2058 | 1414 | 2144 | 911 | 1619 | 503 | 525 |
| Apr. 1, 2000 | 938 | 2672 | 1020 | 2732 | 636 | 2313 | 383 | 419 |
| May 1, 2000 | 834 | 1733 | 890 | 1813 | 611 | 1439 | 279 | 373 |
| Jun. 1, 2000 | 1046 | 3400 | 1092 | 3501 | 880 | 3159 | 212 | 342 |
| Jul. 1, 2000 | 1133 | 2196 | 1184 | 2406 | 1011 | 1999 | 173 | 408 |
| Aug. 1, 2000 | 1532 | 2360 | 1658 | 2462 | 1441 | 2199 | 218 | 264 |

-continued

| | Production Rate History | | Primary + Secondary | | Secondary Portion | | Primary Portion | |
|---|---|---|---|---|---|---|---|---|
| | Producer P2 | Producer P3 | CRM P2 | CRM P3 | CRM P2 | CRM P3 | CRM P2 | CRM P3 |
| Date | | | | | | | | |
| Sep. 1, 2000 | 854 | 2305 | 884 | 2382 | 787 | 2173 | 97 | 210 |
| Oct. 1, 2000 | 870 | 2518 | 893 | 2631 | 820 | 2410 | 73 | 221 |
| Nov. 1, 2000 | 1336 | 3209 | 1376 | 3286 | 1299 | 3121 | 77 | 165 |
| Dec. 1, 2000 | 741 | 1648 | 808 | 1696 | 714 | 1576 | 95 | 121 |
| Jan. 1, 2001 | 1619 | 2540 | 1741 | 2645 | 1599 | 2481 | 142 | 164 |
| Feb. 1, 2001 | 1420 | 3523 | 1516 | 3831 | 1405 | 3475 | 111 | 357 |
| Mar. 1, 2001 | 772 | 1558 | 800 | 1587 | 761 | 1518 | 39 | 68 |
| Apr. 1, 2001 | 558 | 1462 | 566 | 1521 | 550 | 1430 | 16 | 92 |
| May 1, 2001 | 1833 | 2909 | 1966 | 2972 | 1827 | 2883 | 139 | 90 |
| Jun. 1, 2001 | 1137 | 3419 | 1198 | 3492 | 1132 | 3398 | 66 | 95 |

Similar to the case of no primary recovery zonal contribution from each of producing zones for secondary production is estimated using CRM zonal level interwell connectivities as shown before while the primary recovery contribution is evaluated by using at least one measurement of production profile data for each producer to divide the primary production portion of to its contributing zones, in the example of the producer P2 CRM estimates a total production rate of 950 bbl/day (highlighted in table above), and profile is obtained on February 2000 indicating 332 (234+98) and 618 (378+240) bbl/day production for Zone Z1 and Z2 accordingly; and for producer P3 CRM estimates a total production rate of 1813 bbl/day (highlighted in table above), a profile is obtained on May 2000 indicating the production rate of 906 (Secondary portion 70+primary portion 836) and 907 (304+603) bbl/day production for Zone Z1 and Z2 accordingly; therefore, the Primary production portion of a well is divided accordingly to make up for the remaining production of each zone in February 2000 and May 2000 for Producer P2 and P3:

| | Secondary Portions | | | | Primary Portions | | | |
|---|---|---|---|---|---|---|---|---|
| Date | I1Z1-P2 | I1Z2-P2 | I1Z1-P3 | I1Z2-P3 | Z1-P2 | Z2-P2 | Z1-P3 | Z2-P3 |
| Jan. 1, 2000 | 368 | 1060 | 1473 | 1589 | 335 | 540 | 181 | 788 |
| Feb. 1, 2000 | 98 | 240 | 392 | 360 | 234 | 378 | 112 | 485 |
| Mar. 1, 2000 | 101 | 810 | 405 | 1214 | 193 | 310 | 98 | 427 |
| Apr. 1, 2000 | 542 | 94 | 2171 | 142 | 147 | 237 | 78 | 341 |
| May 1, 2000 | 209 | 402 | 836 | 603 | 107 | 172 | 70 | 304 |
| Jun. 1, 2000 | 735 | 145 | 2941 | 218 | 81 | 131 | 64 | 278 |
| Jul. 1, 2000 | 192 | 819 | 771 | 1228 | 66 | 107 | 76 | 331 |
| Aug. 1, 2000 | 14 | 1427 | 58 | 2140 | 83 | 134 | 49 | 214 |
| Sep. 1, 2000 | 396 | 391 | 1587 | 586 | 37 | 60 | 39 | 171 |
| Oct. 1, 2000 | 471 | 349 | 1886 | 523 | 28 | 45 | 41 | 180 |
| Nov. 1, 2000 | 468 | 831 | 1874 | 1246 | 29 | 47 | 31 | 134 |
| Dec. 1, 2000 | 201 | 513 | 806 | 769 | 36 | 58 | 23 | 98 |
| Jan. 1, 2001 | 32 | 1567 | 131 | 2350 | 54 | 87 | 31 | 134 |
| Feb. 1, 2001 | 546 | 859 | 2186 | 1288 | 42 | 68 | 67 | 290 |
| Mar. 1, 2001 | 150 | 611 | 602 | 917 | 15 | 24 | 13 | 56 |
| Apr. 1, 2001 | 241 | 309 | 966 | 463 | 6 | 10 | 17 | 75 |
| May 1, 2001 | 56 | 1771 | 226 | 2656 | 53 | 86 | 17 | 73 |
| Jun. 1, 2001 | 679 | 453 | 2718 | 680 | 25 | 41 | 18 | 77 |

In the running example, CRM estimates of production rates for each contributing zone is then normalized to provide production split of each zone as a continuous value during the production of the producers for both primary and secondary contributions; as shown in table below, these estimate are cross checked with sparse production profile data which also is considered in calibration of the CRM zonal level analysis.

| CRM PLT Estimates (Primary + Secondary) | | | | | |
|---|---|---|---|---|---|
| Time | Z1-P2 | Z2-P2 | Check | Z1-P3 | Z2-P3 | Check |
| Jan. 1, 2000 | 0.31 | 0.69 | | 0.41 | 0.59 | |
| Feb. 1, 2000 | 0.35 | 0.65 | Measured P2 | 0.37 | 0.63 | |
| Mar. 1, 2000 | 0.21 | 0.79 | | 0.23 | 0.77 | |
| Apr. 1, 2000 | 0.68 | 0.32 | | 0.82 | 0.18 | |
| May 1, 2000 | 0.35 | 0.65 | | 0.50 | 0.50 | Measured P3 |
| Jun. 1, 2000 | 0.75 | 0.25 | | 0.86 | 0.14 | |
| Jul. 1, 2000 | 0.22 | 0.78 | | 0.35 | 0.65 | |
| Aug. 1, 2000 | 0.06 | 0.94 | | 0.04 | 0.96 | |
| Sep. 1, 2000 | 0.49 | 0.51 | | 0.68 | 0.32 | |
| Oct. 1, 2000 | 0.56 | 0.44 | | 0.73 | 0.27 | |
| Nov. 1, 2000 | 0.36 | 0.64 | | 0.58 | 0.42 | |
| Dec. 1, 2000 | 0.29 | 0.71 | | 0.49 | 0.51 | |
| Jan. 1, 2001 | 0.05 | 0.95 | | 0.06 | 0.94 | |
| Feb. 1, 2001 | 0.39 | 0.61 | | 0.59 | 0.41 | |
| Mar. 1, 2001 | 0.21 | 0.79 | | 0.39 | 0.61 | |
| Apr. 1, 2001 | 0.44 | 0.56 | | 0.65 | 0.35 | |
| May 1, 2001 | 0.06 | 0.94 | | 0.08 | 0.92 | |
| Jun. 1, 2001 | 0.59 | 0.41 | | 0.78 | 0.22 | |

Those of ordinary skill in the art will appreciate that modifications may be made to the illustrated embodiments, such as the illustrated CRM zonal embodiments (see also FIGS. 34, 35A-35E, 36A-36H, 37A-37I). For example, VOIF may be determined at a well level or at a zonal level. Furthermore, sensitivity analysis may be used. Also, for example, (i) sensitivity analysis may be performed to determine the allowed well connections for CRM, (ii) CRM may be run with sensitivity analysis, (iii) VOIF may be determined for an injection well (or zone) at the steady state with or without sensitivity analysis, and/or (iv) VOIF may be determined for an injection well (or zone) as transient with or without sensitivity analysis. CRM zonal may also be used to determine conformance candidates at zonal level and/or to make recommendations as discussed herein. VOIF may also be used to recommend a conformance candidate (e.g., if fij or fij is more than a threshold such as 0.4, and if VOIF is less than a threshold such as 0.1, and if injection rate is more than average, then the method 3300 may recommend the corresponding well and/or zone as a conformance candidate). Criteria may also be used to recommend a stimulation candidate. Thus, the method 3400 may generate a recommendation. Also, in some embodiments, PLT can be a substitute for oil-cut in determining VOIF.

Furthermore, CRM zonal may be used to determining if there is crossflow between at least two zones. For example, allocation factors may be received or determined from ILT/PLT, K H Q, or other zonal splits (e.g., from zonal application 218). Next, CRM may be run with the assumption that each zone is treated like an injector. Next, the method may include calculating CRM based zonal splits for producers by zone. Next, the method may compare the CRM based zonal splits with those received to determine if there is crossflow.

Those of ordinary skill in the art will appreciate that CRM zonal may be used to identify the value of injected fluid for each zone of a hydrocarbon reservoir (as discussed in the VOIF section herein), to generate PLTs, to identify conformance control issues (as discussed in the conformance control section herein), etc.

While many details have been set forth for purpose of illustration, it will be apparent to those skilled in the art that the disclosure is susceptible to alteration and that certain other details described herein can vary considerably without departing from the basic principles of the invention. In addition, it should be appreciated that structural features or method steps shown or described in any one embodiment herein can be used in other embodiments as well.

For the avoidance of doubt, the present application includes the subject-matter defined in the following numbered paragraphs:

Allowed Connections

A1. A computer implemented method of analyzing a flood operation for a hydrocarbon reservoir, the method comprising: establishing a dataset of allowed well connections for at least one production well and at least one injection well of the hydrocarbon reservoir; iteratively modifying the dataset of allowed well connections based on a distance category, a static features category, a dynamic features category, or any combination thereof, wherein the static features category uses static data of the hydrocarbon reservoir and the dynamic features category uses dynamic data of the hydrocarbon reservoir; and after iteratively modifying the dataset of allowed well connections, running capacitance resistance modeling using the modified dataset of allowed well connections as an input.

A2. The method of paragraph A1, further comprising using at least one interwell connectivity generated by running capacitance resistance modeling to modify the dataset of allowed well connections.

A3. The method of paragraph A1, wherein the hydrocarbon reservoir includes a plurality of zones, and wherein each zone is treated as an injection well.

A4. The method of paragraph A1, wherein iteratively modifying the dataset of allowed well connections includes using a priority between the categories.

A5. The method of paragraph A1, wherein iteratively modifying the dataset of allowed well connections based on the distance category includes using a priority within the distance category, a sensitivity analysis for the distance category, or both.

A6. The method of paragraph A1, wherein iteratively modifying the dataset of allowed well connections based on the static features category includes using a priority within the static features category, a sensitivity analysis for the static features category, or both.

A7. The method of paragraph A1, wherein iteratively modifying the dataset of allowed well connections based on the dynamic features category includes using a priority within the dynamic features category, a sensitivity analysis for the dynamic features category, or both.

A8. The method of paragraph A1, wherein the static data includes geological data, seismic data, three dimensional (3D) seismic data, faults, fractures, geobodies, geological boundaries, a processed version of any of these, or any combination thereof.

A9. The method of paragraph A1, wherein the dynamic data includes well production data, injection rate data, pressure data, location data, fluid production geochemistry data, tracer data, log data, production log data, well log data, well test data, time lapse seismic data, four dimensional (4D) seismic data, maps of change in pressure and saturation, maps of pressure and saturation, preliminary well connections, pressure transient, pulse test, capacitance resistance modeling output data, polygon data, a processed version of any of these, or any combination thereof.

A10. The method of paragraph A1, further comprising updating at least one application based on output from the capacitance resistance modeling.

A11. A computer implemented method of analyzing a flood operation for a hydrocarbon reservoir, the method comprising: determining a dataset of allowed well connections for at least one production well and the at least one injection well of the hydrocarbon reservoir based on a distance category; determining a dataset of allowed well connections for the at least one production well and the at least one injection well of the hydrocarbon reservoir based on a static features category, wherein the static features category uses static data of the hydrocarbon reservoir; determining a dataset of allowed well connections for the at least one production well and the at least one injection well of the hydrocarbon reservoir based on a dynamic features category, wherein the dynamic features category uses dynamic data of the hydrocarbon reservoir; comparing the determined allowed well connections from the various datasets; combining the determined allowed well connections from the various datasets based on the comparison and a priority into a combined dataset of allowed well connections; and running capacitance resistance modeling using the combined dataset of allowed well connections as an input.

A12. The method of paragraph A11, further comprising using at least one interwell connectivity generated by running capacitance resistance modeling to modify the combined dataset of allowed well connections.

A13. The method of paragraph A11, wherein the hydrocarbon reservoir includes a plurality of zones, and wherein each zone is treated as an injection well.

A14. The method of paragraph A11, wherein determining the dataset of allowed well connections based on the distance category includes using a priority within the distance category, a sensitivity analysis for the distance category, or both.

A15. The method of paragraph A11, wherein determining the dataset of allowed well connections based on the static features category includes using a priority within the static features category, a sensitivity analysis for the static features category, or both.

A16. The method of paragraph A11, wherein determining the dataset of allowed well connections based on the dynamic features category includes using a priority within the dynamic features category, a sensitivity analysis for the dynamic features category, or both.

A17. The method of paragraph A11, wherein the static data includes geological data, seismic data, three dimensional (3D) seismic data, faults, fractures, geobodies, geological boundaries, a processed version of any of these, or any combination thereof.

A18. The method of paragraph A11, wherein the dynamic data includes well production data, injection rate data, pressure data, location data, fluid production geochemistry data, tracer data, log data, production log data, well log data, well test data, time lapse seismic data, four dimensional (4D) seismic data, maps of change in pressure and saturation, maps of pressure and saturation, preliminary well connections, pressure transient, pulse test, capacitance resistance modeling output data, polygon data, a processed version of any of these, or any combination thereof.

A19. The method of paragraph A1, further comprising updating at least one application based on output from the capacitance resistance modeling.

A20. A computing system for analyzing a flood operation for a hydrocarbon reservoir, the system comprising: at least one processor; and at least one memory containing computer executable instructions, that when executed by the at least one processor, cause the computing system to: establish a dataset of allowed well connections for at least one production well and at least one injection well of the hydrocarbon reservoir; iteratively modify the dataset of allowed well connections based on a distance category, a static features category, a dynamic features category, or any combination thereof, wherein the static features category uses static data of the hydrocarbon reservoir and the dynamic features category uses dynamic data of the hydrocarbon reservoir; and after iteratively modifying the dataset of allowed well connections, run capacitance resistance modeling using the modified dataset of allowed well connections as an input.

Comparing Different Flood Operations/PF

B1. A computer implemented method of analyzing at least a first flood operation and a second flood operation on a hydrocarbon reservoir having at least one production well and at least one injection well, the method comprising: for each of the first flood operation and the second flood operation: receiving production data for the at least one production well and injection data for the at least one injection well for the flood operation; running capacitance resistance modeling using the received production data and the received injection data for the flood operation to generate a response time and an interwell connectivity per injection well and production well pair for the flood operation; using the generated response times, the generated interwell connectivities, the received production data, the received injection data, or any combination thereof to generate a proxy of pore volume swept per injection well and production well pair for the flood operation; and aggregating the generated proxies of pore volume swept per injection well and production well pair for the flood operation to generate an estimate of pore volume swept at a well level, at a reservoir level, or both for the flood operation; and comparing the generated estimate of pore volume swept for the first flood operation and the generated estimate of pore volume swept for the second flood operation to determine a change in sweep efficiency at the well level, at the reservoir level, or both.

B2. The method of paragraph B1, further comprising, for each of the first flood operation and the second flood operation, determining heterogeneity at the well level, the reservoir level, or both.

B3. The method of paragraph B2, further comprising comparing the determined heterogeneity of the first flood operation and the determined heterogeneity of the second flood operation to determine a change in heterogeneity at the well level, at the reservoir level, or both.

B4. The method of paragraph B3, further comprising comparing the determined change in heterogeneity and the determined change in sweep efficiency to verify accuracy of the determined change in sweep efficiency.

B5. The method of paragraph B1, wherein the hydrocarbon reservoir includes a plurality of zones, and wherein each zone is treated as an injection well.

B6. The method of paragraph B1, wherein the production data includes production rate and flowing pressure data as a function of time, and wherein the injection data includes injection rate and flowing pressure data as a function of time.

B7. The method of paragraph B1, wherein the first flood operation, the second flood operation, or both is a polymer flood operation, further comprising accounting for rheology of the polymer used in the polymer flood operation in the running of the capacitance resistance modeling.

B8. The method of paragraph B7, wherein accounting for the rheology in running capacitance resistance modeling includes separating each injection well and production well pair of the polymer flood operation into at least three tanks, wherein the three tanks include a near injection well tank, a near production well tank, and a middle tank between the near injection well tank and the near production well tank.

B9. The method of paragraph B8, wherein the production data includes production rate and flowing pressure data as a function of time, and wherein the injection data includes injection rate and flowing pressure data as a function of time, and wherein accounting for the rheology in running capacitance resistance modeling includes using (i) material balance equations for each of the tanks, (ii) the injection and production rates, (iii) the injection and production flowing pressure data, and (iv) a polymer rheology.

B10. The method of paragraph B8, wherein accounting for the rheology in running capacitance resistance modeling includes using a capacitance resistance modeling polymer formulation:

$$\bar{\tau}_j \tau_j \frac{\partial}{\partial t}\left(\frac{\partial(q_{p,j}^n(t) + q_{o,j}(t))}{\partial t} + J_j \frac{\partial P_{wf,j}}{\partial t}\right) + \bar{\tau}_j \frac{\partial}{\partial t}(q_{p,j}(t) + q_{o,j}(t)) +$$
$$\left(\bar{\tau}_j \frac{\bar{J}_j}{J_j} + \tau_j\right)\left(\frac{\partial(q_{p,j}^n(t) + q_{o,j}(t))}{\partial t} + J_j \frac{\partial P_{wf,j}}{\partial t}\right) + (q_{p,j}(t) + q_{o,j}(t)) =$$
$$\sum_{i=1}^{Ni} f_{i,j}\left(i_{i,p}(t) + \tau_i\left(\frac{\partial i_{i,p}^n(t)}{\partial t} - J_i \frac{\partial P_{wf,i}}{\partial t}\right)\right)$$

wherein $\tau_i$ is a time constant for the near injection well tank associated with injection well i, $\tau_j$ is a time constant for the near production well tank associated with production well j, $\bar{\tau}_j$ is a time constant for the middle tank, $J_i$ is an injectivity index for injection well i, $J_j$ is a productivity index for production well j, $\bar{J}_j$ is a productivity index for the middle tank, $P_{wf,j}$ is a well flowing pressure for production well j, $P_{wf,i}$ is a well flowing pressure for injection well i, $i_{i,p}(t)$ is a flow rate of the polymer in injection well i, $q_{p,j}(t)$ is a polymer flow rate in production well j, $q_{o,j}(t)$ is an oil flow rate in production well j and n defines the polymer rheology.

B11. A computing system for analyzing at least a first flood operation and a second flood operation on a hydrocarbon reservoir having at least one production well and at least one injection well, the system comprising: at least one processor; and at least one memory containing computer executable instructions, that when executed by the at least one processor, cause the computing system to perform a method comprising: for each of the first flood operation and the second flood operation: receiving production data for the at least one production well and injection data for the at least one injection well for the flood operation; running capacitance resistance modeling using the received production data and the received injection data for the flood operation to generate a response time and an interwell connectivity per injection well and production well pair for the flood operation; using the generated response times, the generated interwell connectivities, the received production data, the received injection data, or any combination thereof to generate a proxy of pore volume swept per injection well and production well pair for the flood operation; and aggregating the generated proxies of pore volume swept per injection well and production well pair for the flood operation to generate an estimate of pore volume swept at a well level, at a reservoir level, or both for the flood operation; and comparing the generated estimate of pore volume swept for the first flood operation and the generated estimate of pore volume swept for the second flood operation to determine a change in sweep efficiency at the well level, at the reservoir level, or both.

B12. The computing system of paragraph B11, wherein the computer executable instructions are further configured to, for each of the first flood operation and the second flood operation, determine heterogeneity at the well level, the reservoir level, or both.

B13. The computing system of paragraph B12, wherein the computer executable instructions are further configured to compare the determined heterogeneity of the first flood operation and the determined heterogeneity of the second flood operation to determine a change in heterogeneity at the well level, at the reservoir level, or both.

B14. The computing system of paragraph B13, wherein the computer executable instructions are further configured to compare the determined change in heterogeneity and the determined change in sweep efficiency to verify accuracy of the determined change in sweep efficiency.

B15. The computing system of paragraph B11, wherein the hydrocarbon reservoir includes a plurality of zones, and wherein each zone is treated as an injection well.

B16. The computing system of paragraph B11, wherein the first flood operation, the second flood operation, or both is a polymer flood operation, and wherein the computer executable instructions are further configured to account for rheology of the polymer used in the polymer flood operation in the running of the capacitance resistance modeling.

B17. A computer implemented method of analyzing a polymer flood operation on a hydrocarbon reservoir having at least one injection well and at least one production well, the method further comprising: receiving production data for the at least one production well and injection data for the at least one injection well for the flood operation; and running capacitance resistance modeling using the received production data and the received injection data for the polymer flood operation to generate a response time and an interwell connectivity per injection well and production well pair for the polymer flood operation, wherein running capacitance resistance modeling includes accounting for rheology of the polymer used in the polymer flood operation in the running of the capacitance resistance modeling.

B18. The method of paragraph B17, wherein accounting for the rheology in running capacitance resistance modeling includes separating each injection well and production well pair of the polymer flood operation into at least three tanks, wherein the three tanks include a near injection well tank, a near production well tank, and a middle tank between the near injection well tank and the near production well tank.

B19. The method of paragraph B18, wherein the production data includes production rate and flowing pressure data as a function of time, and wherein the injection data includes injection rate and flowing pressure data as a function of time, and wherein accounting for the rheology in running capacitance resistance modeling includes using (i) material balance equations for each of the tanks, (ii) the injection and production rates, (iii) the injection and production flowing pressure data, and (iv) a polymer rheology.

B20. The method of paragraph B18, wherein accounting for the rheology in running capacitance resistance modeling includes using a capacitance resistance modeling polymer formulation:

$$\overline{\tau}_j \tau_j \frac{\partial}{\partial t}\left(\frac{\partial (q_{p,j}^n(t)+q_{o,j}(t))}{\partial t} + J_j \frac{\partial P_{wf,j}}{\partial t}\right) + \overline{\tau}_j \frac{\partial}{\partial t}(q_{p,j}(t)+q_{o,j}(t)) +$$

$$\left(\overline{\tau}_j \frac{J_j}{\bar{J}_j} + \tau_j\right)\left(\frac{\partial (q_{p,j}^n(t)+q_{o,j}(t))}{\partial t} + J_j \frac{\partial P_{wf,j}}{\partial t}\right) + (q_{p,j}(t)+q_{o,j}(t)) =$$

$$\sum_{i=1}^{N_i} f_{i,j}\left(i_{i,p}(t) + \tau_i\left(\frac{\partial i_{i,p}^n(t)}{\partial t} - J_i \frac{\partial P_{wf,i}}{\partial t}\right)\right)$$

wherein $\tau_i$ is a time constant for the near injection well tank associated with injection well i, $\tau_j$ is a time constant for the near production well tank associated with production well j, $\overline{\tau}_j$ is a time constant for the middle tank, $J_i$ is an injectivity index for injection well i, $J_j$ is a productivity index for production well j, $\bar{J}_j$ is a productivity index for the middle tank, $P_{wf,j}$ is a well flowing pressure for production well j, $P_{wf,i}$ is a well flowing pressure for injection well i, $i_{i,p}(t)$ is a flow rate of the polymer in injection well i, $q_{p,j}(t)$ is a polymer flow rate in production well j, $q_{o,j}(t)$ is an oil flow rate in production well j and n defines the polymer rheology.

Pattern Management

C1. A computer implemented method of using producer centered polygons to identify at least one infill drilling location in a hydrocarbon reservoir having a plurality of producers and at least one injector, the method comprising: load well locations, reservoir boundary, and injection rate and production rate histories; creating producer-centered polygons based on the producer locations and the reservoir boundary; calculating an area ($A_i$) of any given producer by each polygon associated with each producer based on geometry or the geological boundary of the polygon; for each producer, calculating cumulative oil production (Qi) and a ratio between Qi and Ai; ranking the producers from smallest to largest Q/A ratio; and locating infill drilling places in the polygons with high-ranking producers.

C2. The method of paragraph C1, wherein the producer centered polygons are producer centered Voronoi polygons.

C3. The method of paragraph C1, wherein the area is a drainage area, a pore volume, a proxy for OOIP, or any combination thereof.

C4. A computer implemented method of using polygons to choose between a first infill candidate in a first hydrocarbon reservoir and a second infill candidate in a different second hydrocarbon reservoir, wherein each of the hydrocarbon reservoirs has a plurality of producers and at least one injector, the method comprising: for the first hydrocarbon reservoir: loading well locations, reservoir boundary, and injection rate and production rate histories; creating producer-centered polygons based on the producer locations and the reservoir boundary; calculating an area covered (Ai) by each polygon associated with each producer based on geometry of the polygon; for each producer, calculating cumulative oil production (Qi) and rank producers from largest Q to smallest Q; for each producer, calculating cumulative oil production (Qi) and a ratio between Qi and Ai; ranking the producers from smallest to largest Q/A ratio; calculating a norm area and norm cumulative oil production in the first reservoir; calculating an index of the uneven sweep (IUS) of the first reservoir.

C5. The method of paragraph C4, further comprising repeat steps of paragraph C1 for the second reservoir.

C6. The method of paragraph C5, further comprising selecting the reservoir for infill drilling opportunity with the largest IUS.

C7. The method of paragraph C4, wherein the producer centered polygons are producer centered Voronoi polygons.

C8. The method of paragraph C4, wherein the area is a drainage area, a pore volume, a proxy for OOIP, or any combination thereof.

C9. The method of paragraph C4, wherein the norm area is pore volume.

C10. A computer implemented method of using streamgrids for pattern realignment for a hydrocarbon reservoir having at least one producer and at least one injector, the method comprising: loading well locations and injection rate and production rate histories for all wells; creating streamgrid based on the well locations; calculating allocation factors for injector and producers based an allocation method; calculating allocated water injection and water production within each streamgrid between connected injector-producer pair) calculating water cycling between connected injector-producer pair for each streamgrid; defining a threshold for the water cycling based on a distribution; and identifying at least one streamgrid that has water cycling above the threshold for converting the producer in the identified streamgrid for pattern realignment C11. The method of paragraph C10, wherein the allocation method is an injection angle, a producer angle, or any combination thereof.

C12. The method of paragraph C10, wherein the allocated water injection and water production within each streamgrid are calculated between connected injector-producer pair.

C13. A computer implemented method of using streamgrid allocation factors to initiate capacitance resistance modeling interwell connectivity, the method comprising: loading well locations and injection rate and production rate histories for all wells of a hydrocarbon reservoir having at least one producer and at least one injector; creating streamgrid based on well locations; calculating allocation factors for injector based on and allocation method; exporting the allocation factors as initial values of interwell connectivity between well pairs in the capacitance resistance modeling.

C14. The method of paragraph C13, wherein the allocation method is an injection angle, number of producers, injector Area, or any combination thereof.

C15. A computer implemented method of estimating maximal areal sweep by zone and by reservoir with populated streamgrids, the method comprising: for any given zone of a reservoir: getting the reservoir boundary in that zone and calculating its total area (St); getting contact point of all wells that penetrate and are perforated in that zone; creating streamgrid with well-zone contact locations; calculating total area (S) covered by populated streamgrids; and estimating maximal areal sweep efficiency in that zone, wherein the maximal areal sweep efficiency equals S/St.

C16. The method of paragraph C15, further comprising repeating steps of paragraph C1 for all remaining zones in the reservoir to get the S and St for each zone.

C17. The method of paragraph C16, further comprising calculating a ratio between summation of S from all zones and summation of St from all zones to get a maximum areal sweep efficiency for the reservoir.

Conformance Control

D1. A computer implemented method of identifying conformance candidates, the method comprising: for a first entity: solving an injection entity index to generate an injection entity index value, wherein the injection entity index includes injection efficiency, value of injected fluid, and pore volume injected for a period of time; solving a production entity index to generate a production entity index value, wherein the production entity index includes estimate of remaining movable oil in place; evaluating an operation entity index that represents operation status to generate an operation entity index value; and combining the injection entity index value, the production entity index value, and the operation entity index value to generate a conformance problem index value for the first entity.

D2. The method of paragraph D1, further comprising comparing the generated conformance problem index value for the first and a threshold to determine if the first entity is a conformance candidate.

D3. The method of paragraph D1, further comprising generating a conformance problem index value for at least one other entity.

D4. The method of paragraph D3, further comprising ranking the first entity and the at least one other entity based on the generated conformance problem index values.

D5. The method of paragraph D4, wherein a higher generated conformance problem index value indicates a higher likelihood of a conformance problem.

D6. The method of paragraph D4, wherein the first entity has the highest generated conformance problem index value, and wherein the first entity is at a field level, further comprising generating a conformance problem index value at a reservoir level, well level, a zone level, or any combination thereof.

D7. The method of paragraph D4, wherein the first entity has the highest generated conformance problem index value, and wherein the first entity is at a reservoir level, further comprising generating a conformance problem index value at a well level, a zone level, or any combination thereof.

D8. The method of paragraph D4, wherein the first entity has the highest generated conformance problem index value, and wherein the first entity is at a well level, further comprising generating a conformance problem index value at a zone level.

D9. The method of paragraph D1, wherein the first entity is at a field level, a reservoir level, a well level, a zone level, or any combination thereof.

D10. The method of paragraph D4, wherein the first entity has the highest generated conformance problem index value, and wherein the first entity includes a plurality of zones, further comprising: receiving data for each zone of the plurality of zones, the received data to be used to determine a residence time distribution for each zone; determining the residence time distribution for each zone of the plurality of zones using the received data; identifying at least one zone of the plurality of zones to be treated with a conformance agent by comparing the determined residence time distributions of the zones and a residence time distribution threshold; and recommending a first conformance control treatment at breakthrough time of the slowest identified zone for the at least one identified zone.

D11. The method of paragraph D10, further comprising recommending a slug size for the first conformance control treatment, wherein the slug size is determined by calculating injected volume for a period of time which is not more than 50% of a breakthrough time for the fastest identified zone.

D12. The method of paragraph D10, further comprising recommending a concentration of the conformance agent for the first conformance control treatment, wherein the concentration of the conformance agent is based on a resistance factor of the conformance agent and a rheology of the conformance agent.

D13. The method of paragraph D10, further comprising: receiving updated data for each zone of the plurality of zones after the first conformance control treatment; determining an updated residence time distribution for each zone of the plurality of zone after the first conformance control treatment; identifying at least one zone of the plurality of zones after the first conformance control treatment to be treated with a conformance agent in a second conformance control treatment based on a comparison of the updated residence time distribution of each zone and the residence time distribution threshold; and recommending a second conformance control treatment at an updated breakthrough time of the slowest identified zone after the first conformance control treatment for the at least one identified zone after the first conformance control treatment.

D14. A computer implemented method of determining a conformance control treatment for a well of a hydrocarbon reservoir, wherein the well is in fluidic communication with a plurality of zones of the hydrocarbon reservoir, the method comprising: receiving data for each zone of the plurality of zones, the received data to be used to determine a residence time distribution for each zone; determining the residence time distribution for each zone of the plurality of zones using the received data; identifying at least one zone of the plurality of zones to be treated with a conformance agent by comparing the determined residence time distributions of the zones and a residence time distribution threshold; and recommending a first conformance control treatment at breakthrough time of the slowest identified zone for the at least one identified zone.

D15. The method of paragraph D14, further comprising recommending a slug size for the first conformance control treatment, wherein the slug size is determined by calculating injected volume for a period of time which is not more than 50% of a breakthrough time for the fastest identified zone.

D16. The method of paragraph D14, further comprising recommending a concentration of the conformance agent for the first conformance control treatment, wherein the concentration of the conformance agent is based on a resistance factor of the conformance agent and a rheology of the conformance agent.

D17. The method of paragraph D16, wherein the resistance factor of the conformance agent is sufficient to reduce original velocity of the fastest identified zone by a factor of about 10.

D18. The method of paragraph D14, further comprising: receiving updated data for each zone of the plurality of zones after the first conformance control treatment; determining an updated residence time distribution for each zone of the plurality of zone after the first conformance control treatment; identifying at least one zone of the plurality of zones after the first conformance control treatment to be treated with a conformance agent in a second conformance control treatment based on a comparison of the updated residence time distribution of each zone and the residence time distribution threshold; and recommending a second conformance control treatment at an updated breakthrough time of the slowest identified zone after the first conformance control treatment for the at least one identified zone after the first conformance control treatment.

D19. The method of paragraph D18, further comprising recommending a slug size for the second conformance control treatment, wherein the slug size for the second conformance control treatment is determined by calculating injected volume for a period of time which is not more than 50% of an updated breakthrough time for the fastest identified zone.

D20. The method of paragraph D18, further comprising recommending a concentration of the conformance agent for the second conformance control treatment, wherein the concentration of the conformance agent for the second conformance control treatment is based on a resistance factor of the conformance agent for the second conformance control treatment and a rheology of the conformance agent for the second conformance control treatment.

D21. The method of paragraph D20, wherein the resistance factor of the conformance agent of the second conformance control treatment is sufficient to reduce updated velocity of the fastest identified zone after the first conformance control treatment by a factor of about 10.

D22. A computing system for identifying conformance candidates, the system comprising: at least one processor; and at least one memory containing computer executable instructions, that when executed by the at least one processor, cause the computing system to perform a method comprising: for a first entity: solving an injection entity index to generate an injection entity index value, wherein the injection entity index includes injection efficiency, value of injected fluid, and pore volume injected for a period of time, solving an production entity index to generate an production entity index value, wherein the production entity index includes estimate of remaining movable oil in place; evaluating an operation entity index that represents operation status to generate an operation entity index value; and combining the injection entity index value, production entity index value, and the operation entity index value to generate a conformance problem index value for the first entity.

Heavy Oil Flood Operation

E1. A computer implemented method of analyzing a flood operation on a hydrocarbon reservoir having heavy oil, the method comprising: for a first injection well of the hydrocarbon reservoir: receiving injection rate data and production rate data for production wells communicating with the first injection well for a period of time; establishing a plurality of time windows based on breakthrough time of each production well that has broken through until the current date, wherein the production rate data is indicative of breakthrough; running capacitance resistance modeling for each established time window to generate interwell connectivities for each well pair; solving a continuous function for each well pair using the capacitance resistance modeling generated interwell connectivity of the well pair over time to estimate interwell connectivity for each well pair in the future; using the production rate data to solve an oil-cut model for each production well that has broken through to estimate oil-cut value for each production well in the future; and determining a value of injected fluid for the first injection well as a function of time in the future using the continuous function estimated interwell connectivity and the estimated oil-cut value.

E2. The method of paragraph E1, further comprising: establishing at least one sliding scale time window between two established time windows; and running the capacitance resistance modeling for each established sliding time window to generate interwell connectivities for each well pair, wherein the generated interwell connectivities derived from the sliding time window are included in the solving of the continuous function.

E3. The method of paragraph E1, wherein the continuous function is bell shaped, log-normal, betta, logistic curve, or any combination thereof.

E4. The method of paragraph E1, further comprising comparing the generated average forecast value of injected fluid for the first injection well and a threshold to determine if the first injection well is a candidate for stimulation.

E5. The method of paragraph E1, further comprising generating an average forecast value of injected fluid for at least one other injection well.

E6. The method of paragraph E5, further comprising ranking the first injection well and the at least one other injection well based on the generated average forecast values of injected fluid.

E7. The method of paragraph E1, wherein all of the productions wells communication with the first injection well have broken through.

E8. The method of paragraph E1, wherein less than all of the productions wells communication with the first injection well have broken through.

E9. The method of paragraph E1, wherein determining the value of injected fluid as a function of time for the first injection well includes using an equation, wherein the equation is: $VOIF(t)=\Sigma_j^N f_{ij}(t) f_{oj}(t)$ wherein $f_{oj}(t)$ is oil cut as a function of time and $f_{ij}(t)$ is interwell connectivity as a function of time.

E10. A computing system for analyzing a flood operation on a hydrocarbon reservoir having heavy oil, the system comprising: at least one processor; and at least one memory containing computer executable instructions, that when executed by the at least one processor, cause the computing system to perform a method comprising: for a first injection well of the hydrocarbon reservoir: receiving injection rate data and production rate data for production wells communicating with the first injection well for a period of time; establishing a plurality of time windows based on breakthrough time of each production well that has broken through until the current date, wherein the production rate data is indicative of breakthrough; running capacitance resistance modeling for each established time window to generate interwell connectivities for each well pair; solving a continuous function for each well pair using the capacitance resistance modeling generated interwell connectivity of the well pair over time to estimate interwell connectivity for each well pair in the future; using the production rate data to solve an oil-cut model for each production well that has broken through to estimate oil-cut value for each production well in the future; and determining a value of injected fluid for the first injection well as a function of time in the future using the continuous function estimated interwell connectivity and the estimated oil-cut value.

E11. The system of paragraph E10, wherein the computer executable instructions are further configured to establish at least one sliding scale time window between two established time windows; and run the capacitance resistance modeling for each established sliding time window to generate interwell connectivities for each well pair, wherein the generated interwell connectivities derived from the sliding time window are included in the solving of the continuous function.

E12. The system of paragraph E10, wherein the continuous function is bell shaped, log-normal, betta, logistic curve, or any combination thereof.

E13. The system of paragraph E10, wherein the computer executable instructions are further configured to compare the generated average forecast value of injected fluid for the first injection well and a threshold to determine if the first injection well is a candidate for stimulation.

E14. The system of paragraph E10, wherein the computer executable instructions are further configured to generate an average forecast value of injected fluid for at least one other injection well.

E15. The system of paragraph E14, wherein the computer executable instructions are further configured rank to the first injection well and the at least one other injection well based on the generated average forecast values of injected fluid.

E16. The system of paragraph E10, wherein all of the productions wells communication with the first injection well have broken through.

E17. The system of paragraph E10, wherein less than all of the productions wells communication with the first injection well have broken through.

E18. The system of paragraph E10, wherein determining the value of injected fluid as a function of time for the first injection well includes using an equation, wherein the equation is: $VOIF(t)=\Sigma_j^N f_{ij}(t) f_{oj}(t)$ wherein $f_{oj}(t)$ is oil cut as a function of time and $f_{ij}(t)$ is interwell connectivity as a function of time.

E19. A computer-readable storage medium comprising computer-executable instructions which, when executed by a computing system, cause the computing system to perform a method of analyzing a flood operation on a hydrocarbon reservoir having heavy oil, the method comprising: for a first injection well of the hydrocarbon reservoir: receiving injection rate data and production rate data for production wells communicating with the first injection well for a period of time; establishing a plurality of time windows based on breakthrough time of each production well that has broken through until the current date, wherein the production rate data is indicative of breakthrough; running capacitance resistance modeling for each established time window to generate interwell connectivities for each well pair; solving a continuous function for each well pair using the capacitance resistance modeling generated interwell connectivity of the well pair over time to estimate interwell connectivity for each well pair in the future; using the production rate data to solve an oil-cut model for each production well that has broken through to estimate oil-cut value for each production well in the future; and determining a value of injected fluid for the first injection well as a function of time in the future using the continuous function estimated interwell connectivity and the estimated oil-cut value.

E20. The computer-readable storage medium of paragraph E19, further comprising generating an average forecast value of injected fluid for at least one other injection well; and ranking the first injection well and the at least one other injection well based on the generated average forecast values of injected fluid.

VOIF

F1. A computer implemented method of determining a value of injected fluid for a flood operation on a hydrocarbon reservoir, the method comprising: for a first injection well of the hydrocarbon reservoir: receiving injection rate data for the first injection well and production rate data for at least one production well communicating with the injection well; running capacitance resistance modeling using the received data to generate an interwell connectivity for each injection well and production well pair; determining a value of injected fluid for each injection well and production well pair using the generated interwell connectivity for the well pair and an oil-cut value for the production well of the pair; and aggregating the generated values of injected fluid per pair to determine a value of injected fluid for the first injection well.

F2. The method of paragraph F1, further comprising generating a value of injected fluid for at least one other injection well.

F3. The method of paragraph F2, further comprising ranking the first injection well and the at least one other injection well based on the values of injected fluid.

F4. The method of paragraph F3, further comprising generating a net value of injected fluid for the first injection well and the at least one other injection well.

F5. The method of paragraph F4, further comprising re-ranking the first injection well and the at least one other injection well based on the net values of injected fluid.

F6. The method of paragraph F1, wherein the value of injected fluid for the first injection well is determined at a steady state.

F7. The method of paragraph F1, wherein the value of injected fluid for the first injection well is determined as transient.

F8. The method of paragraph F1, wherein the value of injected fluid for the first injection well is determined using sensitivity analysis.

F9. The method of paragraph F1, wherein the hydrocarbon reservoir may include a plurality of zones, and each zone is treated as an injection well.

F10. The method of paragraph F1, further comprising recommending a conformance candidate or a stimulation candidate.

F11. The method of paragraph F1, further comprising recommending a target injection rate.

F12. A computing system for determining a value of injected fluid for a flood operation on a hydrocarbon reservoir, the system comprising: at least one processor; and at least one memory containing computer executable instructions, that when executed by the at least one processor, cause the computing system to perform a method comprising: for a first injection well of the hydrocarbon reservoir: receiving injection rate data for the first injection well and production rate data for at least one production well communicating with the injection well; running capacitance resistance modeling using the received data to generate an interwell connectivity for each injection well and production well pair; determining a value of injected fluid for each injection well and production well pair using the generated interwell connectivity for the well pair and an oil-cut value for the production well of the pair; and aggregating the generated values of injected fluid per pair to determine a value of injected fluid for the first injection well.

F13. The system of paragraph F12, wherein the computer executable instructions are further configured to generate a value of injected fluid for at least one other injection well.

F14. The system of paragraph F13, wherein the computer executable instructions are further configured to rank the first injection well and the at least one other injection well based on the values of injected fluid.

F15. The system of paragraph F14, wherein the computer executable instructions are further configured to generate a net value of injected fluid for the first injection well and the at least one other injection well.

F16. The system of paragraph F15, wherein the computer executable instructions are further configured to re-rank the first injection well and the at least one other injection well based on the net values of injected fluid.

F17. The system of paragraph F12, wherein the value of injected fluid for the first injection well is determined at a steady state, as transient, using sensitivity analysis, or any combination thereof.

F18. The system of paragraph F12, wherein the hydrocarbon reservoir may include a plurality of zones, and each zone is treated as an injection well.

F19. The system of paragraph F12, further comprising recommending a conformance candidate, a stimulation candidate, a target injection rate, or any combination thereof.

F20. A computer-readable storage medium comprising computer-executable instructions which, when executed by a computing system, cause the computing system to perform a method of determining a value of injected fluid for a flood operation on a hydrocarbon reservoir, the method comprising: for a first injection well of the hydrocarbon reservoir: receiving injection rate data for the first injection well and production rate data for at least one production well communicating with the injection well; running capacitance resistance modeling using the received data to generate an interwell connectivity for each injection well and production well pair; determining a value of injected fluid for each injection well and production well pair using the generated interwell connectivity for the well pair and an oil-cut value for the production well of the pair; and aggregating the generated values of injected fluid per pair to determine a value of injected fluid for the first injection well.

CRM Zonal

G1. A computer implemented method for analyzing a flood operation for a hydrocarbon reservoir having a plurality of zones, the method comprising: receiving injection profile data (ILT) and injection rates; using the received injection profile data and injection rates to split each injection well into multiple zonal level injectors; and running capacitance resistance modeling treating each zonal level injector as a single injector, wherein running capacitance resistance modeling includes generating interwell connectivities at the zonal level.

G2. The method of paragraph G1, further comprising determining if there is crossflow between at least two zones.

G3. The method of paragraph G1, further comprising generating at least one PLT.

G4. The method of paragraph G1, further comprising generating continuous production profile (PLT).

G5. The method of paragraph G4, wherein continuous production profile (PLT) is generated if secondary recovery is contributing in production, which can be obtained from injection rates and zonal level connectivities by summing up contribution of zonal injectors and their connectivities to at least one of the producers.

G6. The method of paragraph G4, wherein continuous production profile from primary and secondary production is obtained by using the primary and secondary recovery portion of CRM estimate once the CRM zonal is performed.

G7. The method of paragraph G6, wherein the primary portion of production profile is estimated from CRM zonal level primary portion which is an exponential decline.

G8. The method of paragraph G6, wherein the secondary portion of production rates at zonal level are obtained from summing the multiplication of injection rates and connectivities at zonal level from all injectors contributing in the production of a given producer.

G9. The method of paragraph G1, further comprising interpolating for PLT, ILT, or both.

G10. A computing system for analyzing a flood operation for a hydrocarbon reservoir having a plurality of zones, the system comprising: at least one processor; and at least one memory containing computer executable instructions, that when executed by the at least one processor, cause the computing system to perform a method comprising: receiving injection profile data (ILT) and injection rates; using the received injection profile data and injection rates to split each injection well into multiple zonal level injectors; and running capacitance resistance modeling treating each zonal level injector as a single injector, wherein running capacitance resistance modeling includes generating interwell connectivities at the zonal level.

G11. The system of paragraph G10, wherein the computer executable instructions are further configured to generate a value of injected fluid for at least one other injection well.

G12. The system of paragraph G10, wherein the computer executable instructions are further configured to determine if there is crossflow between at least two zones.

G13. The system of paragraph G10, wherein the computer executable instructions are further configured to generate at least one PLT.

G14. The system of paragraph G10, wherein the computer executable instructions are further configured to generate continuous production profile (PLT).

G15. The system of paragraph G14, wherein the continuous production profile (PLT) is generated if secondary recovery is contributing in production, which can be obtained from injection rates and zonal level connectivities by summing up contribution of zonal injectors and their connectivities to at least one of the producers.

G16. The system of paragraph G14, wherein the continuous production profile from primary and secondary production is obtained by using the primary and secondary recovery portion of CRM estimate once the CRM zonal is performed.

G17. The system of paragraph G16, wherein the primary portion of production profile is estimated from CRM zonal level primary portion which is an exponential decline, G18. The system of paragraph G16, wherein the secondary portion of production rates at zonal level are obtained from summing the multiplication of injection rates and connectivities at zonal level from all injectors contributing in the production of a given producer.

G19. The system of paragraph G10, wherein the computer executable instructions are further configured to interpolate for PLT, ILT, or both.

G20. A computer-readable storage medium comprising computer-executable instructions which, when executed by a computing system, cause the computing system to perform a method of analyzing a flood operation for a hydrocarbon reservoir having a plurality of zones, the method comprising: receiving injection profile data (ILT) and injection rates; using the received injection profile data and injection rates to split each injection well into multiple zonal level injectors; and running capacitance resistance modeling treating each zonal level injector as a single injector, wherein running capacitance resistance modeling includes generating interwell connectivities at the zonal level.

from first provisional patent application:

H1. A computer implemented method of using Capacitance Resistance Model (CRM) to identify candidate injector wells, the method comprising: receiving injector data for a plurality of injector wells, producer data for a plurality of producer wells, and flowing pressure data as well as relative bottomhole location, injection and production profile data, polygons indicating geo-bodies, geological boundaries or structural boundaries such as fault or fractures from 3D seismic and/or 4D seismic data; pressure transient testing data including any of pulse test, interwell tracer information indicating well pair in communication; receiving phase data for phases; performing CRM analysis using the received data; repeating the CRM analysis; identifying a plurality of candidate injector wells from injector well properties including any of value of injection, priorities workover, conformance control characteristics both in areal and vertical sweep efficiency; and determining at least a candidate injector well from the plurality of injector wells.

H2. The method of paragraph H1, further comprising identifying a plurality of candidate injector wells and a plurality of producer wells responsive to connectivity maps.

H3. The method of paragraph H2, wherein the at least a candidate injector well is determined from the plurality of injector wells and the plurality of producer wells.

H4. The method of paragraph H1, further comprising ranking the plurality of candidate injector wells.

H5. The method of paragraph H1, wherein performing CRM analysis comprises performing sensitivity analysis by a) adding noise based on measurement accuracy to injection, production and pressure data to generate many data set, b) representing different earth model by allowing or limiting connectivities compared to a base case model; c) perform sliding time window based analysis to attain interactivity as a function of time; and d) screening connectivities based on their confidence level.

H6. The method of paragraph H1, wherein the connectivity maps indicate high connectivity of >0.5, with high confidence as demonstrated by coefficient of variation less than 10%, and wherein the connectivities that exist are common in all history-matched model with similar history-matched error post adding noise to the input data.

H7. The method of paragraph H6, further comprising identifying the candidate injector well zone, wells and area as targets for conformance operations.

H8. The method of paragraph H1, wherein the connectivity maps indicate low connectivity (>0.25), with high confidence as demonstrated by coefficient of variation less than 10%, and wherein the connectivities that exist are common in all history-matched model with similar history-matched error post adding noise to the input data.

H9. The method of paragraph H8, further comprising identifying the candidate injector well zone, wells and area as targets for enhanced oil recovery operations.

H10. The method of paragraph H9, wherein the enhanced oil recovery operations include at least one of chemical flooding or polymer flooding.

H11. The method of paragraph H1, wherein the injector data includes injector profile data over time, wherein the injector profile data includes a distribution of injection for each zone.

H12. The method of paragraph H1, wherein the producer data includes producer profile data over time, wherein the producer profile data includes a distribution of production for each zone.

H13. The method of paragraph H1, further comprising receiving at least one of geological data, tracer data, or pulse test data; and using it in one or more of the analyses.

H14. The method of paragraph H1, wherein the phase data includes at least one of total injected fluid.

H15. The method of paragraph H14, wherein the injected fluid is selected from any of water, hydrocarbons (gas or oil); $CO_2$, $N_2$, and combinations thereof.

H16. The method of paragraph H15, wherein the injected fluid is injected in sequence, and alternating between different injection fluids.

H17. The method of paragraph H15, wherein the injected fluid is sour gas.

H18. The method of paragraph H1, further comprising determine an injection value for all injectors, and wherein the injector value for each injector indicates the amount of oil being produced in offset producers by injecting in the injector.

H19. The method of paragraph H18, wherein the injector value is a measure of ranking, prioritizing work over, acid jobs, increasing injection to improve reservoir performance.

H20. The method of paragraph H19, further comprising quantifying contribution of injectors as a function of oil production to evaluate external factors.

H21. The method of paragraph H20, wherein the external factor is from an aquifer as a driving force.

H22. The method of paragraph H20, further comprising identifying an injector well with the highest injection value.

H23. A computer implemented method of generating zonal split data, the method comprising: receiving first profile from either ILT (injection logging tools) or PLT (production logging tools) data for a first date; receiving a second ILT/PLT data for a second date; and interpolating between the first PLT data and the second PLT data to dynamically generate zonal split data between the first date and the second date.

H24. A computer implemented method of generating zonal split data, the method comprising: receiving first ILT data for a first date; receiving second ILT data for a second date; and interpolating between the first ILT data and the second ILT data to dynamically generate zonal split data between the first date and the second date.

H25. The method of paragraph H24, further comprising generating a continuous production profile based on inter-well connectivity model obtained using CRM at zonal level.

H26. A method performing flooding analysis, the method comprising using a combination of CRM, a zonal splits generator, and a streamgrid.

H27. A method performing flooding analysis, the method comprising: using interpreted seismic data (3D or 4D) to condition CRM connectivity model to the more likely scenario of the earth model and potential communicating well pairs indicating location of geological or pressure barriers.

H28. The method of paragraph H27, further comprising identifying interwell cumulative injected fluid agreement with saturation change from 4D seismic data during history matching.

H29. A method performing flooding analysis, the method comprising dynamically generating and redefining patterns for a plurality of injector wells and a plurality of producer wells.

H30. The method of paragraph H29, further comprising using at least one of Delaunay triangulation or Voronoi.

from second provisional patent application:

I1. A computer implemented method of analyzing a flooding operation for a subterranean hydrocarbon bearing reservoir, the method comprising: establishing a dataset of allowed well connections for a plurality of injection wells and production well of the subterranean reservoir; iteratively modifying the dataset of allowed well connections based on a distance category, a static features category, a dynamic features category, or any combination thereof, wherein the static features category uses static data of the subterranean reservoir and the dynamic features category uses dynamic data of the subterranean reservoir; and after iteratively modifying the dataset of allowed well connections, running capacitance resistive modeling (CRM) using the modified dataset of allowed well connections as an input.

I2. The method of paragraph I1, wherein iteratively modifying the dataset of allowed well connections according to a priority, wherein the priority includes using an order, wherein the order is the distance category first, the static features category second, and the dynamic features category third.

I3. The method of paragraph I1, wherein iteratively modifying the dataset of allowed well connections according to a priority, wherein the priority includes using an order, wherein the order is the dynamic features category first, the static features second, and the distance category third.

I4. The method of paragraph I1, wherein there is a priority within the distance category.

I5. The method of paragraph I1, wherein there is a priority within the static features category.

I6. The method of paragraph I1, wherein there is a priority within the dynamic features category.

I7. The method of paragraph I1, wherein the static data includes at least one of geological data, seismic data, three dimensional (3D) seismic data, faults, fractures, geobodies, or a processed version of any of these.

I8. The method of paragraph I1, wherein the dynamic data includes at least one of well production data, injection rate data, pressure data, location data, fluid production geochemistry data, tracer data, log data, production log data, well log data, well test data, time lapse seismic data, four dimensional (4D) seismic data, maps of change in pressure and saturation, maps of pressure and saturation, preliminary well connections, pressure transient, pulse test, a processed version of any of these, or any combination thereof.

I9. The method of paragraph I1, wherein running capacitance resistive modeling (CRM) is constrained by at least one geological data, seismic data, three dimensional (3D) seismic data, faults, fractures, geobodies, well production data, injection rate data, pressure data, location data, fluid production geochemistry data, tracer data, log data, production log data, well log data, well test data, time lapse seismic data, four dimensional (4D) seismic data, maps of change in pressure and saturation, maps of pressure and saturation, preliminary well connections, pressure transient, pulse test, a processed version of any of these, or any combination thereof.

I10. The method of paragraph I1, further comprising updating at least one application or component based on output from the running of CRM.

I11. The method of paragraph I1, wherein modifying the dataset of allowed well connections includes modifying a value of an allowed well connection in response to receiving user input indicating that the value should be changed.

I12. A computer system for analyzing a flooding operation for a subterranean hydrocarbon bearing reservoir, the system comprising: at least one processor; and at least one memory containing computer executable instructions, that when executed by the at least one processor, cause the computing system to perform the method of paragraph I1.

I13. A computer program product including a non-transitory computer-readable medium having computer-readable code on it, the computer readable code being configured to implement the method of paragraph I1.

I14. A computer implemented method of analyzing a flooding operation for a subterranean hydrocarbon bearing reservoir, the method comprising: determining a dataset of allowed well connections for a plurality of injection wells and production well of the subterranean reservoir based on a distance category; determining a dataset of allowed well connections for a plurality of injection wells and production well of the subterranean reservoir based on a static features category, wherein the static features category uses static data of the subterranean reservoir; determining a dataset of allowed well connections for a plurality of injection wells and production well of the subterranean reservoir based on a static features category, wherein the dynamic features category uses dynamic data of the subterranean reservoir; comparing the determined well connections; combining the determined well connections based on the comparisons and a priority to determine allowed well connections; and running capacitance resistive modeling (CRM) using the allowed well connections as an input.

I15. The method of paragraph I14, wherein the priority includes the dynamic features category having the highest priority, the static features category having the next highest priority, and the distance category having the next highest priority.

I16. The method of paragraph I14, wherein there is a priority within the distance category.

I17. The method of paragraph I14, wherein there is a priority within the static features category.

I18. The method of paragraph I14, wherein there is a priority within the dynamic features category.

I19. The method of paragraph I14, wherein the static data includes at least one of geological data, seismic data, three dimensional (3D) seismic data, faults, fractures, geobodies, or a processed version of any of these.

I20. The method of paragraph I14, wherein the dynamic data includes at least one of well production data, injection rate data, pressure data, location data, fluid production geochemistry data, tracer data, log data, production log data, well log data, well test data, time lapse seismic data, four dimensional (4D) seismic data, maps of change in pressure and saturation, maps of pressure and saturation, preliminary well connections, pressure transient, pulse test, a processed version of any of these, or any combination thereof.

I21. The method of paragraph I14, wherein running capacitance resistive modeling (CRM) is constrained by at least one geological data, seismic data, three dimensional (3D) seismic data, faults, fractures, geobodies, well production data, injection rate data, pressure data, location data, fluid production geochemistry data, tracer data, log data, production log data, well log data, well test data, time lapse seismic data, four dimensional (4D) seismic data, maps of change in pressure and saturation, maps of pressure and saturation, preliminary well connections, pressure transient, pulse test, a processed version of any of these, or any combination thereof.

I22. The method of paragraph I14, further comprising updating at least one application or component based on output from the running of CRM.

I23. The method of paragraph I14, further comprising modifying a value of an allowed well connection in response to receiving user input indicating that the value should be changed.

I24. A computer system for analyzing a flooding operation for a subterranean hydrocarbon bearing reservoir, the system comprising: at least one processor; and at least one memory containing computer executable instructions, that when executed by the at least one processor, cause the computing system to perform the method of paragraph I14.

I25. A computer program product including a non-transitory computer-readable medium having computer-readable code on it, the computer readable code being configured to implement the method of paragraph I14.

I26. A computer implemented method of analyzing a flooding operation for a subterranean hydrocarbon bearing reservoir, the method comprising: receiving field data for the subterranean reservoir; processing the field data for the subterranean reservoir; determining allowed well connections; and running capacitance resistive modeling (CRM) using the allowed well connections as an input.

I27. The method of paragraph I26, wherein determining allowed well connections includes using at least one of geological data, seismic data, three dimensional (3D) seismic data, faults, fractures, geobodies, well production data, injection rate data, pressure data, location data, fluid production geochemistry data, tracer data, log data, production log data, well log data, well test data, time lapse seismic data, four dimensional (4D) seismic data, maps of change in pressure and saturation, maps of pressure and saturation, preliminary well connections, pressure transient, pulse test, a processed version of any of these, or any combination thereof.

I28. The method of paragraph I26, wherein running capacitance resistive modeling (CRM) is constrained by at least one geological data, seismic data, three dimensional (3D) seismic data, faults, fractures, geobodies, well production data, injection rate data, pressure data, location data, fluid production geochemistry data, tracer data, log data, production log data, well log data, well test data, time lapse seismic data, four dimensional (4D) seismic data, maps of change in pressure and saturation, maps of pressure and saturation, preliminary well connections, pressure transient, pulse test, a processed version of any of these, or any combination thereof.

I29. The method of paragraph I26, further comprising updating at least one application or component based on output from the running of CRM.

I30. A computer system for analyzing a flooding operation for a subterranean hydrocarbon bearing reservoir, the system comprising: at least one processor; and at least one memory containing computer executable instructions, that when executed by the at least one processor, cause the computing system to perform the method of paragraph I26.

I31. A computer program product including a non-transitory computer-readable medium having computer-readable code on it, the computer readable code being configured to implement the method of paragraph I26.

I32. A method of analyzing a flooding operation for a subterranean hydrocarbon bearing reservoir, the method comprising: injecting material into the reservoir for the flooding operation; determining allowed well connections from data from the reservoir, wherein the allowed well connections are input to capacitance resistive modeling (CRM); and making at least one decision that is likely to improve the flooding operation based on the output of CRM.

I33. The method of paragraph I32, wherein the at least one decision is related to optimization, history matching, conformance control, changing a parameter of the flooding operation, or any combination thereof.

I34. The method of paragraph I32, wherein determining the allowed well connections includes using at least one of geological data, seismic data, three dimensional (3D) seismic data, faults, fractures, geobodies, well production data, injection rate data, pressure data, location data, fluid production geochemistry data, tracer data, log data, production log data, well log data, well test data, time lapse seismic data, four dimensional (4D) seismic data, maps of change in pressure and saturation, maps of pressure and saturation, preliminary well connections, pressure transient, pulse test, a processed version of any of these, or any combination thereof.

I35. The method of paragraph I32, wherein determining the allowed well connections includes: establishing a dataset of allowed well connections for a plurality of injection wells and production well of the subterranean reservoir; modifying the dataset of allowed well connections based on a distance category, a static features category, a dynamic features category, or any combination thereof, wherein the static features category uses static data of the subterranean reservoir and the dynamic features category uses dynamic data of the subterranean reservoir, wherein the modified dataset provides the allowed well connections that are input to capacitance resistive modeling (CRM).

I36. The method of paragraph I32, wherein determining the allowed well connections includes: determining a dataset of allowed well connections for a plurality of injection wells and production well of the subterranean reservoir based on a distance category; determining a dataset of allowed well connections for a plurality of injection wells and production well of the subterranean reservoir based on a static features category, wherein the static features category uses static data of the subterranean reservoir; determining a dataset of allowed well connections for a plurality of injection wells and production well of the subterranean reservoir based on a static features category, wherein the dynamic features category uses dynamic data of the subterranean reservoir; comparing the determined well connections; and combining the determined well connections based on the comparisons and a priority to determine allowed well connections.

What is claimed is:

1. A method of determining a value of injected fluid for a flood operation on a hydrocarbon reservoir, the method comprising:
for a first injection well of the hydrocarbon reservoir:
receiving injection rate data for the first injection well and production rate data for at least one production well communicating with the injection well;
running capacitance resistance modeling using the received data to generate an interwell connectivity for each injection well and production well pair;
determining a value of injected fluid for each injection well and production well pair using the generated interwell connectivity for the well pair and an oil-cut value for the production well of the pair, wherein the value of injected fluid for each injection well and production well pair represents an amount of hydrocarbon production for the pair; and
aggregating the generated values of injected fluid per pair in which the first injection well is part of the pair to determine a value of injected fluid for the first injection well that represents an amount of hydrocarbon production from all corresponding production wells; and
generating a value of injected fluid for at least one other injection well;
ranking the first injection well and the at least one other injection well based on the values of injected fluid of the injection well and the least one other injection well; and
adjusting a target injection rate for one or more injection wells based on the ranking and injecting fluid into the one or more injection wells based on the adjusted target injection rate.

2. The method of claim 1, further comprising generating a net value of injected fluid for each of the first injection well and the at least one other injection well, wherein the net value of injected fluid represents an amount of hydrocarbon production for an amount of injected fluid in that particular injection well.

3. The method of claim 2, further comprising re-ranking the first injection well and the at least one other injection well based on the net values of injected fluid.

4. The method of claim 1, wherein the value of injected fluid for the first injection well is determined at a steady state.

5. The method of claim 1, wherein the value of injected fluid for the first injection well is determined as transient.

6. The method of claim 1, wherein the value of injected fluid for the first injection well is determined using sensitivity analysis.

7. The method of claim 1, wherein the hydrocarbon reservoir may include a plurality of zones, and each zone is treated as an injection well.

8. The method of claim 1, further comprising recommending a conformance candidate or a stimulation candidate.

9. The method of claim 1, further comprising recommending a target injection rate.

10. A system for determining a value of injected fluid for a flood operation on a hydrocarbon reservoir, the system comprising:
at least one processor; and
at least one memory containing computer executable instructions, that when executed by the at least one processor, cause the computing system to perform a method comprising:
for a first injection well of the hydrocarbon reservoir:
receiving injection rate data for the first injection well and production rate data for at least one production well communicating with the injection well;
running capacitance resistance modeling using the received data to generate an interwell connectivity for each injection well and production well pair;
determining a value of injected fluid for each injection well and production well pair using the generated interwell connectivity for the well pair and an oil-cut value for the production well of the pair, wherein the value of injected fluid for each injection well and production well pair represents an amount of hydrocarbon production for the pair; and
aggregating the generated values of injected fluid per pair in which the first injection well is part of the pair to determine a value of injected fluid for the first injection well that represents an amount of hydrocarbon production from all corresponding production wells; and
generating a value of injected fluid for at least one other injection well; and
ranking the first injection well and the at least one other injection well based on the values of injected fluid of the injection well and the least one other injection well; and
a well control device for adjusting a target injection rate for one or more injection wells based on the ranking and injecting fluid into the one or more injection wells based on the adjusted target injection rate.

11. The system of claim 10, wherein the computer executable instructions are further configured to generate a net value of injected fluid for each of the first injection well and the at least one other injection well, wherein the net value of injected fluid represents an amount of hydrocarbon production for an amount of injected fluid in that particular injection well.

12. The system of claim 11, wherein the computer executable instructions are further configured to re-rank the first injection well and the at least one other injection well based on the net values of injected fluid.

13. The system of claim 10, wherein the value of injected fluid for the first injection well is determined at a steady state, as transient, using sensitivity analysis, or any combination thereof.

14. The system of claim 10, wherein the hydrocarbon reservoir may include a plurality of zones, and each zone is treated as an injection well.

15. The system of claim 10, further comprising recommending a conformance candidate, a stimulation candidate, a target injection rate, or any combination thereof.

16. The method of claim 1, wherein the value of injected fluid for the first injection well is based on 1 barrel of injection into the first injection well.

17. The system of claim 10, wherein the value of injected fluid for the first injection well is based on 1 barrel of injection into the first injection well.

18. A method of determining a value of injected fluid for a flood operation on a hydrocarbon reservoir, the method comprising:

for a first injection well of the hydrocarbon reservoir:
receiving injection rate data for the first injection well and production rate data for at least one production well communicating with the injection well;
running capacitance resistance modeling using the received data to generate an interwell connectivity for each injection well and production well pair;
determining a value of injected fluid for each injection well and production well pair using the generated interwell connectivity for the well pair and an oil-cut value for the production well of the pair, wherein the value of injected fluid for each injection well and production well pair represents an amount of hydrocarbon production for the pair; and
aggregating the generated values of injected fluid per pair in which the first injection well is part of the pair to determine a value of injected fluid for the first injection well that represents an amount of hydrocarbon production from all corresponding production wells; and generating a value of injected fluid for at least one other injection well;

ranking the first injection well and the at least one other injection well based on the values of injected fluid of the injection well and the least one other injection well; and injecting fluid into one or more injection wells based on the ranking.

19. The method of claim 18, further comprising generating a net value of injected fluid for each of the first injection well and the at least one other injection well, wherein the net value of injected fluid represents an amount of hydrocarbon production for an amount of injected fluid in that particular injection well; and re-ranking the first injection well and the at least one other injection well based on the net values of injected fluid.

20. The method of claim 18, wherein the value of injected fluid for the first injection well is based on 1 barrel of injection into the first injection well.

* * * * *